United States Patent
Hocek et al.

(10) Patent No.: US 8,093,226 B2
(45) Date of Patent: Jan. 10, 2012

(54) CYTOSTATIC 7-DEAZAPURINE NUCLEOSIDES

(75) Inventors: Michal Hocek, Prague (CZ); Petr Naus, Prague (CZ)

(73) Assignee: Institute of Organic Chemistry and Biochemistry of the ASCR, V.V.I., Prague (CZ)

( * ) Notice: Subject to any disclaimer, the term of this patent is extended or adjusted under 35 U.S.C. 154(b) by 371 days.

(21) Appl. No.: 12/354,432

(22) Filed: Jan. 15, 2009

(65) Prior Publication Data

US 2009/0203637 A1   Aug. 13, 2009

Related U.S. Application Data

(60) Provisional application No. 61/022,247, filed on Jan. 18, 2008.

(51) Int. Cl.
  *A01N 43/04* (2006.01)
  *A61K 31/70* (2006.01)

(52) U.S. Cl. ............. 514/45; 514/43; 514/46; 536/27.1; 536/27.13

(58) Field of Classification Search .................. None
See application file for complete search history.

(56) References Cited

FOREIGN PATENT DOCUMENTS

| WO | WO-94/17803 | 8/1994 |
|---|---|---|
| WO | WO-00/75158 A2 | 12/2000 |
| WO | WO-03/051899 | 6/2003 |
| WO | WO-2005/021568 | 3/2005 |
| WO | WO-2006/065335 | 6/2006 |

OTHER PUBLICATIONS

Pudlo et al. J. Med. Chem. (1988), vol. 31, pp. 2086-2092.*
Miles et al. JACS (1995), vol. 117, pp. 5951-5957.*
Hocek, M. et al. (2005) "Cytostatic 6-Arylpurine Nucleosides. 6. SAR in Anti-HCV and Cytostatic Activity of Extended Series of 6-Hetarylpurine Ribonucleosides" J. Med. Chem, 48(18):5869-5873.
Iltzsch M. H. et al. (1995) "Structure-Activity Relationship for the Binding of Nucleoside Ligands to Adenosine Kinase From *Toxoplasma gondii*" Biochem. Pharma. 49(10):1501-1512.
International Search Report for PCT/CZ2009/000004, International Filing Date Jan. 15, 2009.
Miles, Robert W. et al. (1995) "Nucleic Acid Related Compounds. 86. Nucleophilic Functionalization of Adenine, Adenosine, Tubercidin, and Formycin Derivitives via Elboration of the Heterocyclic Amino Group into a Readily Displaced 1,2,4-Triazol-4-yl Substituent" J. Am. Chem. Soc. 117(22): 5951-7.
Ramasamy K. et al. (1990) "Synthesis and Antitumor Evaluation in Mice of Certain 7-Deazapurine (Pyrrolo [2,3-d]pyrimidine) and 3-Deazapurine (Imidazo [4,5-c]pyridine) Nucleosides Structurally Related to Sulfinosine, and Sulfonosine" J. Med. Chem. 33(4):1220-1225.
Silhar, P. et al. (2004) "Facile and Efficient Synthesis of 6-(Hydroxymethyl)purines" Organic Letters 6(19):3225-3228.
Silhar, P. et al. (2008) "Synthesis, cytostatic and anti-HCV activity of 6-(N-Substituted aminomethyl)-, 6-(O-substituted hydroxymethyl)- and 6-(S-substituted sulfanylmethyl) purine nucleosides" Bioorg. and Med. Chem. 16(5):2329-2366.
Smith C.M. el al. (1976) "Inhibitors of Hypoxanthine Metabolism in Ehrlich Ascites Tumor Cells in Vitro" Cancer Treatment Rpt. 60(10):1567-1584.
Smith, C.M. et al. (1974) "Improved Methods Form the Study of Drug Effects on Purine Metabolism and Their Application to Nebularine and 7-Deazanebularine" Biochem. Pharma. 23(14):2023-2035.
Ugarkar B.G. et al. (2003) "Adenosine Kinase Inhibitors. 3. Synthesis, SAR, and Antiinflamatory Activity of a Series of L-Lyxofuranosyl Nucleosides" J. Med Chem. 46. 4750-4760.

* cited by examiner

*Primary Examiner* — Patrick Lewis
(74) *Attorney, Agent, or Firm* — J. Elin Hartrum

(57) ABSTRACT

The invention provides compounds of formula I:

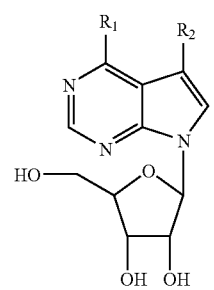

(I)

wherein $R_1$ and $R_2$ have any of the values defined in the specification and salts thereof, as well as compositions comprising such compounds and therapeutic methods that utilize such compounds.

11 Claims, No Drawings

CYTOSTATIC 7-DEAZAPURINE NUCLEOSIDES

CROSS-REFERENCE TO RELATED APPLICATIONS

This application claims priority to U.S. Provisional Application Ser. No. 61/022,247, entitled "Novel Cytostatic 7-Deazapurine Nucleosides", filed Jan. 18, 2008. The contents of this provisional application is herein incorporated by reference in its entirety for all purposes.

BACKGROUND OF THE INVENTION

Currently, there is a need for novel agents that are useful for treating cancer.

SUMMARY OF THE INVENTION

The present invention provides anti-cancer compounds. Accordingly, in one embodiment the invention provides a compound of the invention, which is a compound of formula I:

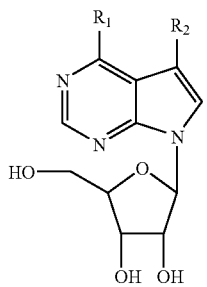

wherein:
R$_1$ is (C$_1$-C$_6$)alkyl, hydroxy(C$_1$-C$_6$)alkyl, aryl, alkyl(C$_1$-C$_6$)alkyl, heteroaryl, heteroaryl(C$_1$-C$_6$)alkyl, or halo, wherein each aryl or heteroaryl is optionally substituted with one or more groups selected from (C$_1$-C$_6$)alkyl, (C$_1$-C$_6$)alkoxy, (C$_1$-C$_6$)alkylthio, halo, amino, nitro, cyano, trifluoromethyl, or hydroxy; and
R$_2$ is hydrogen, heteroaryl, halo, or aryl that is optionally substituted with one or more groups selected from (C$_1$-C$_6$)alkyl, (C$_1$-C$_6$)alkoxy, (C$_1$-C$_6$)alkylthio, halo, amino, nitro, cyano, trifluoromethyl, or hydroxy;
or a salt thereof.

The invention also provides a pharmaceutical composition comprising a compound of formula I, or a pharmaceutically acceptable salt thereof, and a pharmaceutically acceptable excipient.

The invention also provides a method of inhibiting tumor growth or cell proliferation in tumor/cancer cells in vitro or in vivo comprising contacting a subject in need of such treatment with a compound of formula I, or a pharmaceutically acceptable salt thereof.

The invention also provides a method of treating cancer in an animal comprising administering to said animal a compound of formula I, or a pharmaceutically acceptable salt thereof.

The invention also provides a method of inhibiting a neoplastic disease in an animal comprising, administering to said animal a compound of formula I, or a pharmaceutically acceptable salt thereof.

The invention also provides the use of a compound of formula I, or a pharmaceutically acceptable salt thereof to prepare a medicament for inhibiting tumor/cancer cell growth or cell proliferation in tumor/cancer cells, slowing down cell cycle progression in tumor/cancer cells, and for treating cancer in an animal.

The invention also provides the use of a compound of formula I, or a pharmaceutically acceptable salt thereof to prepare a medicament for inhibiting a neoplastic disease in an animal.

The invention also provides synthetic processes and synthetic intermediated disclosed herein that are useful for preparing compounds of formula (I) or salts thereof.

DETAILED DESCRIPTION

For purposes of interpreting this specification, the following definitions will apply and whenever appropriate, terms used in the singular will also include the plural and vice versa.

As used herein, the term "alkyl." refers to a branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. When an alkyl group includes one or more unsaturated bonds, it may be referred to as an alkenyl (double bond) or an alkynyl (triple bond) group. Furthermore, when an alkyl group is linked to an aryl group (defined below), it may be referred to as an "arylalkyl" group.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. As used herein, the term "lower alkoxy" refers to the alkoxy groups having 1-7 carbons and preferably 1-4 carbons.

The term "aryl" refers to monocyclic or bicyclic aromatic hydrocarbon groups having 6-20 carbon atoms in the ring portion. Preferably, the aryl is a (C$_6$-C$_{10}$) aryl. Non-limiting examples include phenyl, biphenyl, naphthyl or tetrahydronaphthyl, each of which may optionally be substituted by 1-4 substituents, such as optionally substituted alkyl, trifluoromethyl, cycloalkyl, halo, hydroxy, alkoxy, acyl, alkyl-C(O)—O—, aryl-O—, heteroaryl-O—, optionally substituted amino, thiol, alkylthio, arylthio, nitro, cyano, carboxy, alkyl-O—C(O)—, carbamoyl, alkylthiono, sulfonyl, sulfonamido, heterocycloalkyl and the like.

Furthermore, the term "aryl" as used herein, also refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "heteroaryl" refers to a 5-14 membered monocyclic- or bicyclic- or fused polycyclic-ring system, having 1 to 8 heteroatoms selected from N, O, S or Se. Preferably, the heteroaryl is a 5-10 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocycloalkyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolinyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-1H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3c]-carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxazinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halo" or "halogen" refers to fluoro, chloro, bromo, and iodo.

As used herein, the term "isomers" refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S). The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto (e.g., phenol or hydroxamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences,* 20th ed., Mack Publishing Company, Easton, Pa., (1985), which is herein incorporated by reference.

As used herein, the term "pharmaceutically acceptable carrier/excipient" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except in so far as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces proliferation of cancer cells, or inhibiting or reducing tumor/cancer growth in vitro or in viva, or inhibiting or reducing a neoplastic disease in a subject such as a mammal. In another preferred embodiment, it also refers to the amount that reduces the primary tumor/cancer size, inhibits cancer cell infiltration into peripheral organs, slows or stops tumor metastasis, or relieves at least to some extent one or more symptoms associated with tumor or cancer, etc.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See *Dorland's Illustrated Medical Dictionary*, (W.B. Saunders Co. 27th ed. 1988).

As used herein, the term "inhibition" or "inhibiting" refers to the reduction or suppression of a given condition, symptom, or disease, or a significant decrease in the baseline activity of a biological activity or process. In one embodiment, it refers to ability to cause reduction of a tumor or cancer growth, or reduction of the tumor or cancer size.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

In one aspect, the present invention provides a compound of formula (I):

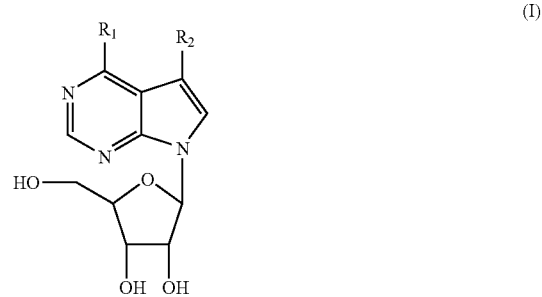

wherein:

$R_1$ is $(C_1-C_6)$alkyl, hydroxy$(C_1-C_6)$alkyl, aryl, aryl$(C_1-C_6)$alkyl, heteroaryl, heteroaryl$(C_1-C_6)$alkyl, or halo, wherein each aryl or heteroaryl is optionally substituted with one or more groups selected from $(C_1-C_6)$alkyl, $(C_1-C_6)$alkoxy, $(C_1-C_6)$alkylthio, halo, amino, nitro, cyano, trifluoromethyl, or hydroxy; and $R_2$ is hydrogen, heteroaryl, halo, or aryl that is optionally substituted with one or more groups selected from $(C_1-C_6)$alkyl, $(C_1-C_6)$alkoxy, $(C_1-C_6)$alkylthio, halo, amino, nitro, cyano, trifluoromethyl, or hydroxy; or a salt thereof.

In another embodiment, the present invention provides the compounds of formula (I), wherein $R_1$ is 5-membered heteroaryl, or hydroxyl-$(C_1-C_4)$alkyl, $R_2$ is hydrogen, or halo, or a salt thereof.

In another embodiment, the present invention provides the compounds of formula (I), wherein $R_1$ is furanyl, thienyl, pyrrolyl, thiazoyl, imidazolyl, pyridyl, selenophenyl, or pyrazolyl, R2 is hydrogen or halo, or a salt thereof.

The present invention provides for compounds of formula I, pharmaceutical compositions employing such compounds comprising a pharmaceutically acceptable salts thereof or a pharmaceutically acceptable carrier/excipient thereof and for methods of using such compounds.

Any asymmetric carbon atom on the compounds of the present invention can be present in the (R)-, (S)- or (R,S)-configuration, preferably in the (R)- or (S)-configuration.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the hydroxyamide or sulfonamide moiety may thus be employed to resolve the compounds of the present invention into their optical antipodes, e.g., by fractional crystallization of a metal (e.g., $Zn^{2+}$) complex formed with an optically active co-ligand, e.g., L- or D-histidine. Racemic products can also be resolved by chiral chromatography, e.g., high pressure liquid chromatography (HPLC) using a chiral adsorbent.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, iso-propoxy, butoxy, iso-butoxy, sec-butoxy, pentoxy, 3-pentoxy, or hexyloxy; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkylthio Can be methylthio, ethylthio, propylthio, isopropylthio, butylthio, isobutylthio, pentylthio, or hexylthio; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$ is $(C_1-C_6)$alkyl.

A specific value for $R_1$ is ethyl.

A specific value for $R_1$ is aryl optionally substituted with one or more $(C_1-C_6)$alkoxy.

A specific value for $R_1$ is phenyl, 4-fluorophenyl, or 4-methoxyphenyl.

A specific value for $R_1$ is aryl$(C_1-C_6)$alkyl.

A specific value for $R_1$ is benzyl.

A specific value for $R_1$ is heteroaryl.

A specific value for $R_1$ is furanyl, thienyl, pyrrolyl, thiazoyl, imidazolyl, pyridyl, selenophenyl, or pyrazolyl.

A specific value for $R_1$ is hydroxy$(C_1-C_6)$alkyl.

A specific value for $R_1$ is 2-hydroxymethyl.

A specific value for $R_2$ is halo.

A specific value for $R_2$ is chloro.

A specific value for $R_2$ is fluoro.

A specific value for $R_2$ is heteroaryl.

A specific value for $R_2$ is furanyl, or thienyl.

A specific value for $R_2$ is phenyl optionally substituted with one or more groups selected from $(C_1-C_6)$alkoxy and $(C_1-C_6)$alkylthio.

A specific value for $R_2$ is 4-methoxyphenyl or 4-methylthiophenyl.

A specific group of compounds of formula I are compounds wherein $R_1$ is heteroaryl and $R_2$ is chloro or fluoro.

A specific group of compounds of formula I are compounds wherein $R_1$ is furanyl, thienyl, pyrrolyl, thiazoyl, imidazolyl, pyridyl, selenophenyl, or pyrazolyl and $R_2$ is chloro or fluoro.

In one embodiment of the invention, the compound of formula I excludes compounds wherein $R_1$ is unsubstituted phenyl and $R_2$ is hydrogen.

The compounds of the present invention are useful in inhibiting tumor/cancer cell growth or cell proliferation in tumor/cancer cells, slowing down cell cycle progression in tumor/cancer cells. In addition, the compounds of the present invention are shown to induce apoptosis. Induction of apoptosis has been used as an important chemotherapy approach in treating cancer/tumor. Accordingly, the compounds of the present invention have valuable pharmaceutical properties, they can be useful as anti-proliferation and anti-tumor/anti-cancer agents.

Therefore, in one aspect, the compounds of the present invention can be used for inhibiting cell proliferation both in vitro and in vivo. In one embodiment, the compounds of the present invention can used to inhibit cell proliferation in a tumor/cancer cell by contacting the tumor/cancer cell with an effective amount of said compounds. In one embodiment, the compounds of the present invention can be used to treat cellular proliferation diseases or conditions. Said diseases can include, but are not limited to, cancer, autoimmune disease, fungal disorders, arthritis, graft rejection, inflammatory bowel disease, cellular proliferation induced after medical procedures, including, but not limited to, surgery, angioplasty, and the like.

In another aspect, the compounds of the present invention can be used for inhibiting tumor/cancer growth both in vitro and in vivo. In one embodiment, the compounds can be used for inhibiting tumor/cancer cell growth by contacting the tumor/cancer cell with an effective amount of said compounds. In one embodiment, the invention provides a method of using the compounds of the present invention for inhibiting tumor or cancer growth. Tumors or cancers that are treatable according to the methods include, for example, tumors or cancers located in the breast, lung, thyroid, lymph node, genitourinary system, kidney, ureter, bladder, ovary, testis, prostate, musculoskeletal system, bone, skeletal muscle, bone marrow, gastrointestinal tract, stomach, esophagus, small bowel, colon, rectum, pancreas, liver, smooth muscle, central or peripheral nervous system, brain, spinal cord, nerves, head, neck, ear, eye, nasopharynx, oropharynx, salivary gland, cardiovascular system, oral cavity, tongue, larynx, hypopharynx, soft tissues, skin, cervix, anus, retina, and/or heart of a mammal.

In one embodiment the invention provides a method of using the compounds of the present invention to treat a neoplastic disease, or a tumor/cancer. As used herein, the term "neoplastic disease" refers to any abnormal growth of cells or tissues being either benign (non-cancerous) or malignant (cancerous). Neoplastic diseases that are treatable according to the methods of the invention include, for example, neoplasms from acute myelogenous leukemia, chronic lymphocytic leukemia, chronic myelogenous leukemia, cutaneous T-cell lymphoma, hairy-cell leukemia and non-Hodgkin's lymphoma.

Additionally, the present invention provides:

a compound of the present invention for use as a medicament;

use of a compound of the present invention for the preparation of a medicament for inhibiting cell proliferation in tumor/cancer cells, or slowing down cell cycle progression in tumor/cancer cells;

use of a compound of the present invention for the preparation of a medicament for treating cellular proliferation diseases or conditions;

use of a compound of the present invention for the preparation of a medicament for inhibiting tumor/cancer growth both in vitro and in vivo;

use of a compound of the present invention for the preparation of a medicament for treating a neoplastic disease.

use of a compound of the present invention for the preparation of a medicament for treating a tumor or cancer.

Processes for preparing compounds of formula I are provided as further embodiments of the invention and are illustrated by the following procedures in which the meanings of the generic radicals are as given above unless otherwise qualified.

A compound of formula I can be prepared as follows.

Chemistry

Palladium catalyzed cross-coupling reactions of protected 6-chloro-7-deazapurine riboside I (Scheme 1, Table 1) with corresponding boronic acids, zinc, tin and aluminium reagents provide desired protected 6-substituted 7-deazapurines 2a-l, which are then deprotected by the treatment with 90% aqueous trifluoroacteic acid affording final free ribosides 3a-3l. It should be noted that under these acidic conditions are also removed N-protecting floc (entry 8) and trityl (entry 10) groups. In the case of 6-hydroxymethyl derivative (entry 12) the benzoyl group is quantitatively deprotected with sodium methoxide in methanol before final acidic deprotection.

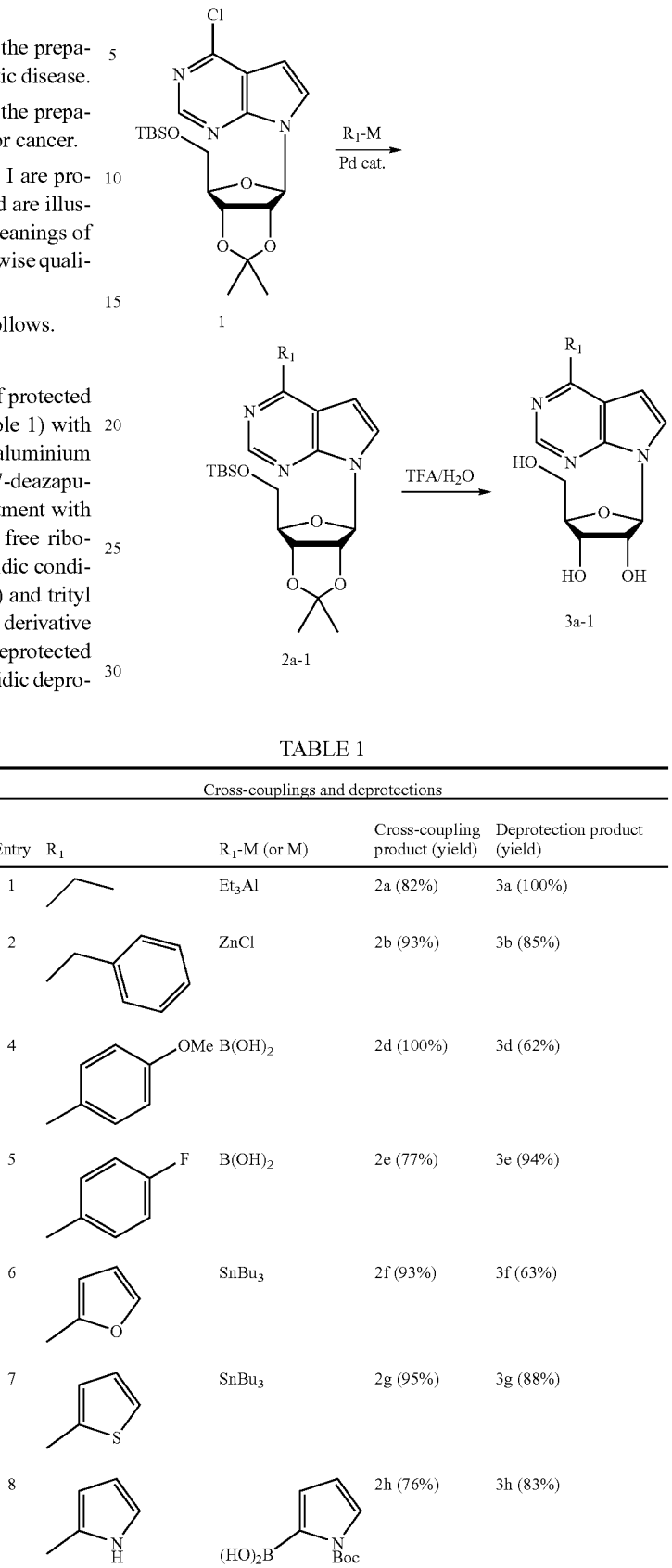

Scheme 1

TABLE 1

| | | Cross-couplings and deprotections | | |
|---|---|---|---|---|
| Entry | $R_1$ | $R_1$-M (or M) | Cross-coupling product (yield) | Deprotection product (yield) |
| 1 | ⟋⟍ | $Et_3Al$ | 2a (82%) | 3a (100%) |
| 2 | benzyl | ZnCl | 2b (93%) | 3b (85%) |
| 4 | 4-methoxyphenylmethyl | $B(OH)_2$ | 2d (100%) | 3d (62%) |
| 5 | 4-fluorophenylmethyl | $B(OH)_2$ | 2e (77%) | 3e (94%) |
| 6 | furyl | $SnBu_3$ | 2f (93%) | 3f (63%) |
| 7 | thienyl | $SnBu_3$ | 2g (95%) | 3g (88%) |
| 8 | pyrrolyl | $(HO)_2B$-pyrrolyl-Boc | 2h (76%) | 3h (83%) |

TABLE 1-continued

Cross-couplings and deprotections

| Entry | R₁ | R₁-M (or M) | Cross-coupling product (yield) | Deprotection product (yield) |
|---|---|---|---|---|
| 9 | 2-thiazolyl | SnBu₃ | 2i (90%) | 3i (85%) |
| 10 | 4-methyl-imidazolyl | BrZn-imidazole-NTr | 2j (66%) | 3j (93%) |
| 11 | 3-pyridyl | B(OH)₂ | 2k (95%) | 3k (83%) |
| 12 | —CH₂OH | IZn—CH₂—OBz | 2l (54%)[a] | 3l (92%) |

[a]In addition to 6-benzoyloxymethyl derivative 2l chromatography also afforded 6-hydroxymethyl 2l' derivative in 23% yield (thus total yield of hydroxymethyl introduction is 77%). This product comes from partial deprotection of benzoyl group during aqueous work-up.

Other 6-hetaryl-7-deazapurine ribosides 3m-3s (Scheme 2, Table 2) are prepared directly from unprotected 6-chloro-7-deazapurine riboside 4 mainly by aqueous Suzuki cross-coupling reaction performed under Shaughnessy conditions (entries 1-6) or by Stille reaction (entry 7). In the case of 3-pyrrolyl derivative N-protecting triisopropylsilyl moiety is deprotected under strongly basic conditions of aqueous coupling (Entry 3). It should be also noted that in the case of NH containing boronic acids (entries 3,5,6) we observe the formation of the product of arylation of this nitrogen atom by the substitution reaction with chloride 4. In the case of 4-pyrazolyl derivative (entry 6) the concomitant N-arylation and Suzuki reaction lead to cross-linked dimer 5 in 18% yield.

Scheme 2

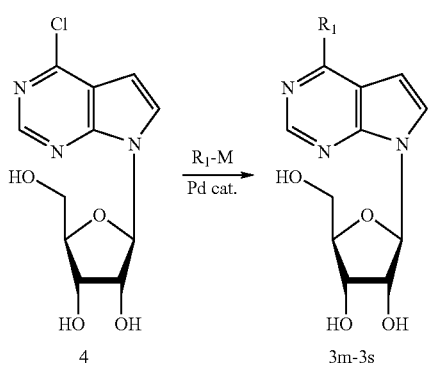

TABLE 2

Cross-couplings of free nucleoside 4

| Entry | R₁ | R₁-M (or M) | Cross-coupling prouct (yield) |
|---|---|---|---|
| 1 | 3-methyl-furyl | B(OH)₂ | 3m (67%) |
| 2 | 3-methyl-thienyl | B(OH)₂ | 3n (69%) |
| 3 | 3-methyl-pyrrolyl-NH | (HO)₂B-pyrrolyl-N-Si(iPr)₃ | 3o (55%) |
| 4 | 2-methyl-selenophene | B(OH)₂ | 3p (64%) |
| 5 | 3-methyl-pyrazolyl-NH | B(OH)₂ | 3q (64%) |
| 6 | 3-methyl-pyrazolyl-NH | B(OH)₂ | 3r (12%)[a] |

TABLE 2-continued

Cross-couplings of free nucleoside 4

| Entry | R$_1$ | R$_1$-M (or M) | Cross-coupling product (yield) |
|---|---|---|---|
| 7 | 2-methylpyridine | SnBu$_3$ | 3s (51%) |

$^a$Yield not optimized. Dimer 5 (18%), R$_f$ = β-D-ribofuranosyl

[Structure of dimer 5 shown]

For the preparation of analogous 6-hetaryl(aryl)-7-fluoro-7-deazapurine ribosides cross-coupling reactions of per-O-benzoylated 6-chloro-7-fluoro-7-deazapurine riboside 6 (Scheme 3, Table 3) are carried out affording products 7a-h which are then subsequently deprotected according to Ziemplén providing free 7-fluoro ribosides 8a-h.

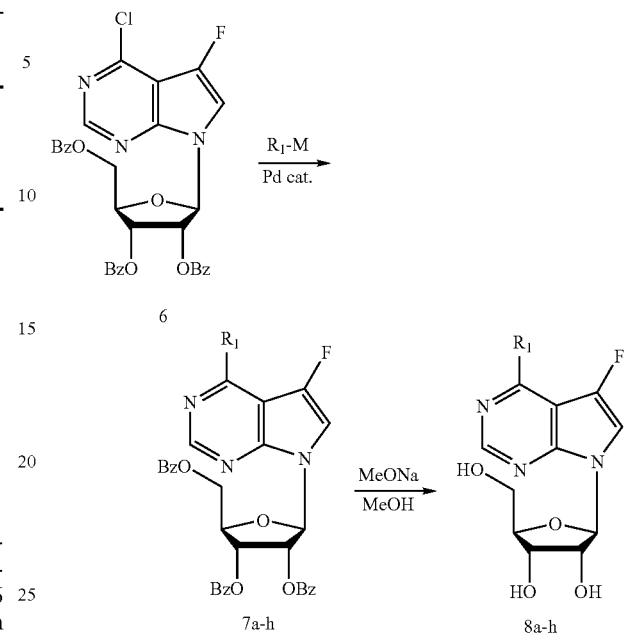

Scheme 3

TABLE 3

Cross-couplings and deprotections

| Entry | R$_1$ | R$_1$-M (or M) | Cross-coupling product (yield) | Deprotection product (yield) |
|---|---|---|---|---|
| 1 | phenyl | B(OH)$_2$ | 7a (93%) | 8a (79%) |
| 2 | 2-furyl | SnBu$_3$ | 7b (100%) | 8b (78%) |
| 3 | 2-thienyl | SnBu$_3$ | 7c (74%) | 8c (74%) |
| 4 | pyrrolyl | ZnCl | 7d (42%) | 8d (89%) |
| 5 | 3-furyl | B(OH)$_2$ | 7e (66%) | 8e (78%) |
| 6 | 3-thienyl | B(OH)$_2$ | 7f (67%) | 8f (81%) |
| 7 | 2-thiazolyl | SnBu$_3$ | 7g (86%) | 8g (68%) |

TABLE 3-continued

Cross-couplings and deprotections

| Entry | R₁ | R₁-M (or M) | Cross-coupling product (yield) | Deprotection product (yield) |
|---|---|---|---|---|
| 8 | 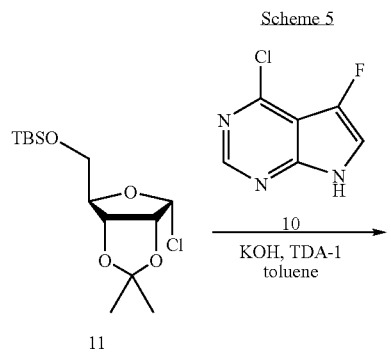 | | 7h (54%) | 8h (70%) |

3-Pyrrolyl derivative 8i is prepared by the aqueous Suzuki reaction of free 6-chloro-7-fluoro-7-deazapurine riboside 9 in 62% yield (Scheme 4).

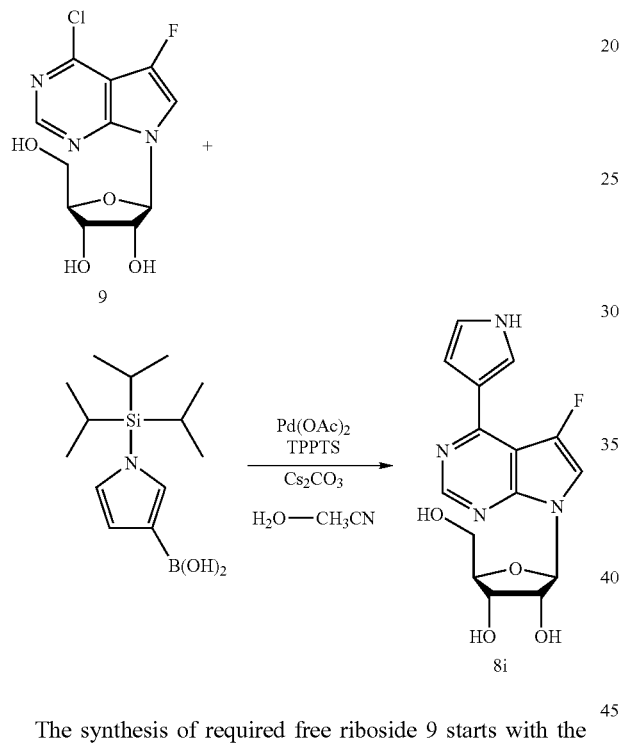

The synthesis of required free riboside 9 starts with the glycosylation of potassium salt of 4-chloro-5-fluoropyrrolo[2,3-d]pyrimidine 10 (Scheme 5) with halogenose 11 providing protected nucleoside 12 in 43% yield. Treatment of this nucleoside 12 with aqueous TFA easily affords free nucleoside 9 in 85% yields.

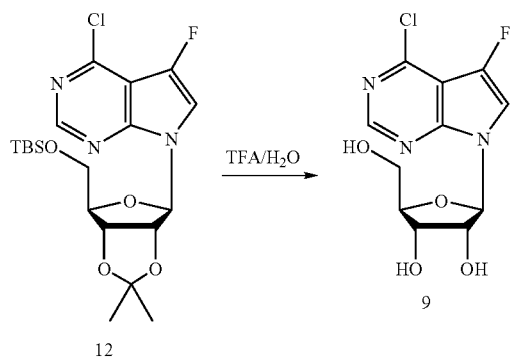

Synthesis of compounds in 7-chloro-7-deazapurine series consists in palladium catalyzed cross-coupling reactions of 6,7-dichloro-7-deazapurine riboside 13 (Scheme 6, Table 4) providing acylated 6-hetaryl(aryl) products 14a-e, which are then smoothly deprotected yielding free nucleosides 15a-e.

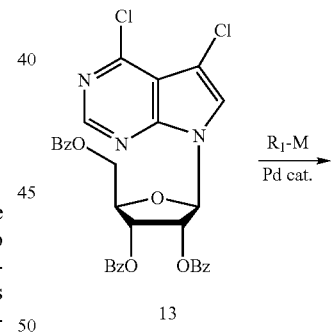

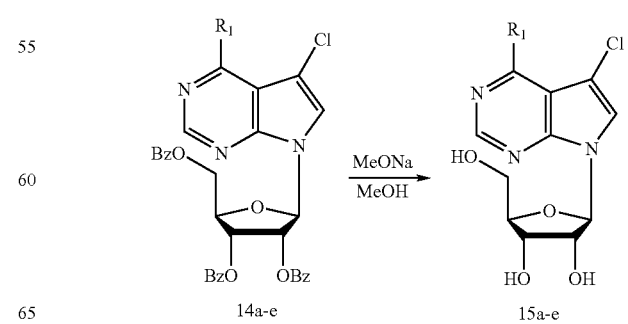

TABLE 4

Cross-couplings and deprotections

| Entry | $R_1$ | $R_1$-M (or M) | Cross-coupling product (yield) | Deprotection product (yield) |
|---|---|---|---|---|
| 1 | phenyl | B(OH)$_2$ | 14a (99%) | 15a (91%) |
| 2 | 2-furyl | SnBu$_3$ | 14b (99%) | 15b (86%) |
| 3 | 2-thienyl | SnBu$_3$ | 14c (89%) | 15c (94%) |
| 4 | 3-furyl | B(OH)$_2$ | 14d (86%) | 15d (80%) |
| 5 | 3-thienyl | B(OH)$_2$ | 14e (92%) | 15e (87%) |

Salts and Hydrates

The compositions of this invention optionally comprise salts of the compounds herein, especially pharmaceutically acceptable non-toxic salts containing, for example, Na$^+$, Li$^+$, K$^+$, Ca$^{+2}$ and Mg$^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired. Some salts may be useful as intermediates for purifying compounds of formula I or for preparing other salts.

Metal salts typically are prepared by reacting the metal hydroxide with a compound of this invention. Examples of metal salts which are prepared in this way are salts containing Li$^+$, Na$^+$, and K$^+$. A less soluble metal salt can be precipitated from the solution of a more soluble salt by addition of the suitable metal compound. In addition, salts may be formed from acid addition of certain organic and inorganic acids, e.g., HCl, HBr, H$_2$SO$_4$, H$_3$PO$_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Treating Cancer

Another aspect of the invention relates to methods of treating cancer. Compositions of the invention may treat cancer, may act intermediates for such treatment or have other utilities as described below. The anti-cancer compounds will bind to locations on the surface or in a cavity of a cancer cell having a geometry unique to the anti-cancer compound. Compositions binding the anti-cancer compound may bind with varying degrees of reversibility. Those compounds binding substantially irreversibly are ideal candidates for use in this method of the invention. Once labeled, the substantially irreversibly binding compositions are useful as probes for the detection of cancer. Accordingly, the invention relates to methods of detecting cancer in a sample suspected of containing cancer comprising the steps of: treating a sample suspected of containing cancer with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention samples suspected of containing cancer include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing cancer. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of cancer after application of the composition can be observed by any method including direct and indirect methods of detecting cancer activity. Quantitative, qualitative, and semiquantitative methods of determining cancer activity are all contemplated. Typically one of the screening methods described above are applied, however, any other method such as observation of the physiological properties of a living organism are also applicable.

Organisms that contain cancer include mammals such as humans. The compounds of this invention are useful in the treatment or prophylaxis of cancer in animals or in man.

However, in screening compounds capable of treating cancer it should be kept in mind that the results of enzyme assays may not correlate with cell culture assays. Thus, a cell based assay should be the primary screening tool.

Screens for Anti-Cancer Compounds

Compositions of the invention are screened for activity against cancer by any of the conventional techniques for evaluating enzyme activity. Within the context of the invention, typically compositions are first screened for activity against cancer in vitro and compositions showing activity are then screened for activity in vivo. Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a fi-ee-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents.

Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of cancerous infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses) or against an active cancerous infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention are also used in combination with other active ingredients. Such combinations are selected based on the condition to be treated, cross-reactivities of ingredients and pharmaco-properties of the combination. For example, when treating cancer, the compositions of the invention can be combined with other chemotherapeutic agents. The second chemotherapeutic agent can be any suitable compound that has biological activity against one or more forms of cancer.

It is also possible to combine any compound of the invention with one or more other active ingredients in a unitary dosage form for simultaneous or sequential administration to an cancer patient. The combination therapy may be administered as a simultaneous or sequential regimen. When administered sequentially, the combination may be administered in two or more administrations. Second and third active ingredients in the combination may have chemotherapeutic activity and include any of the additional chemotherapeutic agents described herein. Exemplary active ingredients to be administered in combination with compounds of the invention are described below.

Suitable additional chemotherapeutic agents include, e.g., antracyclines (e.g., doxorubicin, daunorubicin, epirubicin, idarubicin, and mitoxantrone); (b) other DNA intercalators (e.g., actinomycins C, D, B, etc.; podophyllotoxins, and epipodophyllatoxins (etoposide, teniposide, etoposide)); (c) alkylating agents (e.g., mechlorethamine, melphalan, cyclophosphamide, chlorambucil, ifosfamide, carmustine, lomustine, busulfan, dacarbazine, cisplatin, carboplatin, oxaliplatin, iproplatin, and tetraplatin); (d) hormonal agents (e.g., antiestrogens f estrogen antagonists (tamoxifen and other SERMs); LHRH agonists and antagonists (leuprolide acetate, goserelin, abarelix); aromatase inhibitors; and antiandrogens; (e) chemoprevention agents (e.g., NSAIDs and cis-retinoids); and (f) cell-cycle chemopreventative agents.

Alternatively, the additional chemotherapeutic agent can include, e.g., antineoplasts. Representative antineoplasts include, e.g., adjuncts (e.g., levamisole, gallium nitrate, granisetron, sargramostim strontium-89 chloride, filgrastim, pilocarpine, dexrazoxane, and ondansetron); androgen inhibitors (e.g., flutamide and leuprolide acetate); antibiotic derivatives (e.g., doxorubicin, bleomycin sulfate, daunorubicin, dactinomycin, and idarubicin); antiestrogens (e.g., tamoxifen citrate, analogs thereof, and nonsteroidal antiestrogens such as toremifene, droloxifene and roloxifene); antimetabolites (e.g., fludarabine phosphate, interferon alfa-2b recombinant, methiotrexate sodium, plicamycin, mercaptopurine, and thioguanine); cytotoxic agents (e.g., doxorubicin, carmustine [BCNU], lomustine [CCNU], cytarabine USP, cyclophosphamide, estramucine phosphate sodium, altretamine, hydroxyurea, ifosfamide, procarbazine, mitomycin, busulfan, cyclophosphamide, mitoxantrone, carboplati, cisplati, cisplatin, interferon alfa-2a recombinant, paclitaxel, teniposide, and streptozoci); hormones (e.g., medroxyprogesterone acetate, estradiol, megestrol acetate, octreotide acetate, diethylstilbestrol diphosphate, testolactone, and goserelin acetate); immunomodulators (e.g., aldesleukin); nitrogen mustard derivatives (e.g., melphalan, chlorambucil, mechlorethamine, and thiotepa) and steroids (betamethasone sodium phosphate and betamethasone acetate).

Suitable additional chemotherapeutic agents include, e.g., alkylating agents, antimitotic agents, plant alkaloids, biologicals, topoisomerase I inhibitors, topoisomerase II inhibitors, and synthetics.

Representative alkylating agents include, e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864.

Representative antimitotic agents include, e.g., allocolchicine, Halichondrin B, colchicine, colchicine derivatives, dolastatin 10, maytansine, rhizoxin, paclitaxel derivatives, paclitaxel, thiocolchicine, trityl cysteine, vinblastine sulfate, and vincristine sulfate.

Representative plant alkaloids include, e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere. Representative biologicals include, e.g., alpha interferon, BCG, G-CSF, GM-CSF, and interleukin-2.

Representative topoisomerase I inhibitors include, e.g., camptothecin, camptothecin derivatives, and morpholinodoxorubicin.

Representative topoisomerase II inhibitors include, e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16.

Representative synthetics include, e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium.

Alternatively, the additional chemotherapeutic agent can include tubulin-binding drugs and drugs that affect tubulin dynamics and function. This includes a variety of drugs that are chemically unrelated to vinca alkaloids and taxanes (e.g. CP-248 [a derivative of exisulind] and ILX-651). These drugs have distinctive effects on cells at G2M-phase and may have functionally independent effects on cells in G1 and/or S phase.

Alternatively, the additional chemotherapeutic agent can include selective apoptotic anti-cancer drugs (SAANDs), which include sulindac, aptosyn, CP-461, CP-248 and related sulindac derived compounds that inhibit one or more of the following isozymes of cyclic GMP phosphodiesterase (cGMP PDE): 1, 2, 5.

Alternatively, the additional chemotherapeutic agent can include drugs that inhibit proteosomes (bortezomib or Velcade). Proteosomes degrade many ubiquitinated proteins that have been marked for active destruction. Ubiquitinated proteins include many critical cell cycle regulatory molecules and molecules that regulate apoptosis at specific stages of the cell cycle. While proteosomes may degrade proteins throughout the cell cycle, the proteins that are degraded by proteosomes include some of the most critical cell cycle regulatory proteins. The so-called "cell cycle active rationale" may be applied to the treatment of diseases in various categories, including cancer, inflammatory/autoimmune diseases, and neurological diseases that involve disorderly cell cycle and/or apoptosis.

Alternatively, the additional chemotherapeutic agent can include drugs that inhibit heat shock protein 90 (HSP90), a 'chaperonin' that participates in the degradation of 'client' proteins in the ubiquitin mediated proteosome pathway. Several drugs seem to exert their antitumour effect by inhibiting the intrinsic ATPase activity of HSP90, resulting in degradation of HSP90 "client proteins" via the ubiquitin proteosome pathway. Examples include: geldanamycin, 17-allylamino geldanamycin, 17-demethoxygeldanamycin and radicicol.

Suitable cell-cycle dependent biological agents or schedule-dependent biological agents include drugs, proteins or other molecules that block, impede, or otherwise interfere with, cell cycle progression at the G1-phase, G1/S interface, S-phase, G2/M interface, or M-phase of the cell cycle. These drugs are cell cycle-dependent or schedule-dependent.

Specifically, suitable cell-cycle dependent biological agents or schedule-dependent biological agents include:

(1) Analogues of uridine nucleosides, analogues of thymidine nucleosides, and analogues of uridine and thymidine nucleosides. These compounds act at the S-phase in tumor cells, and possibly neovascular endothelial cells. These compounds include, e.g., 5-fluorodeoxyuridine (floxuridine, FUDR); 5-fluorouracil (5-FU); prodrugs of 5-FU (e.g. capecitabine, 5'-deoxy-5-fluorouridine, ftorafur, flucytosine); bromodeoxyuridine; and iododexoyuridine.

(2) Modulators of fluoropyrimidines. These compounds act at the S-phase in tumor cells, and possibly neovascular endothelial cells. These compounds include, e.g., leurovorin, methotrexate and other folates; levamisole; acivicin; phosphonacetyl-L-aspartic acid (PALA); brequinar; 5-ethynyluracil; and uracil.

(3) Cytidine analogues and cytidine nucleoside analogues. These compounds act at the S-phase in tumor cells, and possibly neovascular endothelial cells. These compounds include, e.g., cytarabine (Ara-C, cytosine arabinoside); gemcitabine (2',2'-difluorodeoxycytidine); and 5-azacytidine.

(4) Purine analogues and purine nucleoside analogues. These compounds act at the S-phase in tumor cells, and possibly neovascular endothelial cells. These compounds include, e.g., 6-thioguanine; 6-mereaptopurine; azathioprine; adenosine arabinoside (Ara-A); 2',2'-difluorodeoxyguanosine; deoxycoformycin (pentostatin); cladribine (2-chlorodeoxyadenosine); and inhibitors of adenosine deaminase.

(5) Antifolates. These compounds act at the S-phase in tumor cells, and possibly neovascular endothelial cells. These compounds include, e.g., methotrexate; aminopterin; trimetrexate; edatrexate; N10-propargyl-5,8-dideazafolic acid (CB3717); ZD1694, 5,8-dideazaisofolic acid (IAHQ); 5,10-dideazatetrahydrofolic acid (DDATHF); 5-deazafolic acid (efficient substrate for FPGS); PT523 (N alpha-(4-amino-4-deoxypteroyl)-N delta-hemiplitlhaloyl-L-ornithine); 10-ethyl-10-deazaminopterin (DDATHF, lomatrexol); piritrexim; 10-EDAM; ZD1694; GW1843; PDX (10-propargyl-10-deazaminopterin); multi-targeted folate (i.e. LY231514, permetrexed); any folate-based inhibitor of thymidylate synthase (TS); any folate-based inhibitor of dihydrofolate reductase (DHFR); any folate-based inhibitor of glycinamide ribonucleotide transformylase (GARTF); any inhibitor of folylpolyglutamate synthetase (FPGS); and any folate-based inhibitor of CAR formyl transferase (AICAR transformylase).

(6) Other antimetabolites. These compounds act at the S-phase in tumor cells, and possibly neovascular endothelial cells. These compounds include, e.g., hydroxyurea and polyamines.

(7) S-phase specific radiotoxins (deoxythymidine analogues). These compounds act at the S-phase in all cells undergoing DNA synthesis. The compounds are incorporated into chromosomal DNA during S-phase. These compounds include, e.g., [125I]-iododeoxyuridine; [123I]-iododeoxyuridine; [124I]-iododeoxyuridine; [80mBr]-iododeoxyuridine; [131I]-iododeoxyuridine; and [211At]-astatine-deoxyuridine.

(8) Inhibitors of enzymes involved in deoxynucleoside/deoxynucleotide metabolism. These compounds act at the S-phase in tumor cells, and possibly neovascular endothelial cells. These compounds include, e.g., inhibitors of thymidylate synthase (TS); inhibitors of dihydrofolate reductase (DHFR); inhibitors of glycinamide ribonucleotide transformylase (GARTF); inhibitors of folylpolyglutamate synthetase (FPGS); inhibitors of GAR formyl transferase (AICAR transformylase); inhibitors of DNA polymerases (DNA Pol; e.g. aphidocolin); inhibitors of ribonucleotide reductase (RNR); inhibitors of thymidine kinase (TK); and inhibitors of topoisomerase I enzymes (e.g. camptothecins, irinotecan [CPT-11, camptosar], topotecan, NX-211 [lurtotecan], rubitecan, etc.).

(9) DNA chain-terminating nucleoside analogues. These compounds act specifically on S-phase cells and are incorporated into chromosomal DNA during S-phase; terminate growing DNA strand. These compounds include, e.g., acyclovir; abacavir; valacyclovir; zidovudine (AZT); didanosine (ddI, dideoxycytidine); zalcitabine (ddC); stavudine (D4T); lamivudine (3TC); Any 2'3'-dideoxy nucleoside analogue; and any 2'3'-dideoxy nucleoside analogue that terminates DNA synthesis. These compounds include, e.g., inhibitors of growth factor receptor tyrosine kinases that regulate progression through the G1-phase, G1/S interface, or S-phase of the cell cycle (e.g. EGF receptors, HER-2 neu/c-erbB2 receptor, PDGF receptors, etc; [e.g. trastusumab, iressa, erbitux, tarceva]); inhibitors of non-receptor tyrosine kinases (e.g. c-src family of tyrosine kinases; [e.g. Gleevec]); inhibitors of serine-threonine kinases that regulate progression through the G1-phase, G1/S interface or S-phase of the cell cycle (e.g. G1 cyclin-dependent kinases, G1/S cyclin-dependent kinases, and S cyclin-dependent kinases [e.g. CDK2, CDK4, CDK5, CDK6]; mitogen-activated kinases; MAP kinase signaling pathway); inhibitors of G1-phase, G1/S interface or S-phase cyclins [e.g. cyclins D1, D2, D3, E, and A]); inhibitors of G-proteins and cGMP phosphodiesterases that positively regulate cell cycle progression at the G1-phase, G1/S interface or S-phase of the cell cycle; drugs that inhibit the induction of immediate early response transcription factors (e.g. N-terminal c-jun kinase, c-myc); and drugs that inhibit proteosomes that degrade 'negative' cell cycle regulatory molecules (e.g. p53, p27/Kip1; [e.g. bortezomib]).

(10) Cytokines, growth factors, anti-angiogenic factors and other proteins that inhibit cell cycle progression at the G1-phase or G1/S interface of the cell cycle. These compounds act at G1, G1/S or S-phase of the cell cycle in tumor cells, and in some cases, neovascular endothelial cells. These compounds include, e.g., interferons; interleukins; somatostatin and somatostatin analogues (octreotide, sandostatin LAR); and many anti-angiogenic factors inhibit cell proliferation of endothelial cells at the G1 or G1/S phases of the cell cycle.

(11) Drugs and compounds that inhibit cell cycle progression at the G2/M interface, or M-phase of the cell cycle. These compounds act at G2/M interface or M-phase of the cell cycle in tumor cells, and in some cases, neovascular endothelial cells. These compounds include, e.g., (a) microtubule-targeting drugs—taxanes (e.g., taxol, taxotere, epothilones, and other taxanes and derivatives); (b) microtubule-targeting drugs—vinca alkaloids (e.g., vinblastine, vincristine, vindesine; vinflunine, vinorelbine, vinzolidine, nocadazole, and colchicines); (c) microtubule-targeting drugs—others (e.g., estramustine, CP-248 and CP-461); (d) inhibitors of serine-threonine kinases that regulate progression through the G2/M interface or M-phase of the cell cycle (e.g., inhibitors of G2/M cyclin-dependent kinases (e.g. CDC2); inhibitors of M-phase cyclins (e.g. cyclin B) and any drug that blocks, impedes, or otherwise interferes with, cell cycle progression at the G2/M interface, or M-phase of the cell cycle).

(12) Radiopharmaceuticals useful in radiation therapy and/or diagnosis. A suitable class of radioisotopes decay by a nuclear disintegration process known as the "Auger Process" or "Auger Cascade". Auger emitting isotopes generate short acting electrons that efficiently cleave duplex DNA. Suitable Auger-emitting radionuclides include, e.g., 125-Iodine, 123-Iodine and 80m-Bromine. Suitable corresponding halogenated pryimidine and purine nucleosides include, e.g., 5-125Iodo-2'-deoxyuridine, 5-123Iodo-2'-deoxyuridine, 5-80mBromo-2'-deoxyuridine and 8-80mBromo-2'-guanidine.

Growth Factors

Many growth factors and cytokines have the capacity to stimulate malignant cells to traverse specific points in the cell cycle. For example, G-CSF or CM-CSF can stimulate leukemic blasts in acute myeloid leukemia to traverse the G1/S interface. This increases the cells' susceptibility to cell-cycle specific drugs, such as cytarabine. Similar strategies have been tested using EGF and cytotoxic drugs for solid tumors. In order to respond the growth factor, cells must be at a specific stage of the cell cycle, e.g., at the G1/S interface. The continuous presence of a growth factor could be beneficial, because at any given time, only a subset of the blasts are at G1/S. Thus, the growth factors act in a cell cycle specific fashion. Similar logic can be applied to the use of hematopoietic growth factors used to treat neutropenia, anemia and thrombocytopenia.

As such, peptide/protein growth factors can be employed in the present invention to promote survival of normal non-malignant cell lineages. One benefit in using such substances is the ability to protect proliferating cells in bone marrow, skin, oral and gastrointestinal mucosa, and hair follicles.

Examples of substances within this category include, e.g., hematopoietic growth factors: G-CSF, GM-CSF, erythropoietin, thrombopoietin and biologically active derivatives of these peptides; keratinocyte growth factor (KGF) for mucositis; B-lymphocyte stimulating peptide (BLys); platelet derived growth factor (PDGF), epithelial growth factor (EGF), TGF-alpha and related growth factors; interleukins (e.g. IL-2, IL-6); other cytokines, growth factors and peptides that stimulate proliferation of non-malignant cells that need to be protected.

Therapeutic Growth Factors/Cytokines

Some therapeutic growth factors/cytokines can inhibit cell proliferation of cancer cells and/or neovascular cells at specific stages of the cell cycle. For example, interferons, somatostatin, octreotide and analogues thereof, thrombospondin and troponin-I inhibit neovascular endothelial cell proliferation by reducing the rate at which the cells enter S-phase. As such, any one or more of these substances can be employed in the present invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/g) to an animal such as rat, mouse, guinea pig, monkey, or to man, allowing sufficient tibe for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-cancer activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

The anti-cancer activity of a compound may be determined using pharmacological models which are well known to the alt, or using Test A described below.

Test A: Cytostatic Cell Culture Assay ($GI_{50}$)

This assay is based on quantification of cell counts by a calorimetric detection of the cell associated proteins. The assay relies on the ability of sulforhodamine B (SRB) to bind to protein components of cells that have been fixed to tissue-culture plates by trichloroacetic acid (TCA). SRB is a bright-pink aminoxanthene dye with two sulfonic groups that bind to basic amino-acid residues under mild acidic conditions, and dissociate under basic conditions. As the binding of SRB is stoichiometric, the amount of dye extracted from stained cells is directly proportional to the cell mass.

Cell lines: All cell lines are obtained from ATCC (Manassas, Va.). Cultivation media containing Glutanax, and trypsin are purchased from Invitrogen (Carlsbad, Calif.). Doxorubicin, Clofarabine, TCA and SRB are from Sigma-Aldrich (St. Louis, Mo.). Gemcitabine is obtained from Moravek Biochemicals (Brea, Calif.)

Assay Protocol:
1. Maintain cell lines in the media listed in Table 1. Trypsinize the sub-confluent cells, count them, and adjust the cell concentrations according to the cell counts listed in Table 1.
2. Distribute the cells into the 96-well plates in 150 μL of media. Incubate the plates overnight in humidified $CO_2$ incubator at 37° C.
3. Fix one plate of each cell line with TCA. Discard the cultivation media from the plates by flicking them gently and add 100 μL cold 10% (vol/vol) TCA to each well. Incubate the plates at 4 degree refrigerator for 1 hour. Discard TCA from the plates by flicking them gently. Rinse plates four times in a washing basin containing tap water. Store the plates at room temperature. These plates represent cell counts on day zero.
4. Prepare a set of medium solutions containing various concentrations of tested compounds by making 5-fold serial dilutions in 96-well plate. Add 50 μL of the diluted compounds per well. Include controls with untreated cells and cells treated with doxorubicin, clofarabine and gemcitabine.
5. Incubate the plates for 5 days at 37° C.
6. Fix the plates with TCA. Discard the cultivation media from the plates by flicking them gently and add 100 μL cold 10% (vol/vol) TCA to each well. Incubate the plates at 4 degree refrigerator for 1 hour. Discard TCA from the plates by flicking them gently. Rinse plates four times in a washing basin containing tap water.
7. Remove excess water by tapping the plates face down, gently on a paper towel. Allow the plates to air-dry at room temperature.
8. Add 100 μL of 0.057% SRB solution in 1% (vol/vol) acetic acid to each well of the plates fixed with TCA on day zero and five. Leave at room temperature for 30 minutes.
9. Flick the plates gently to discard SRB. Rinse the plates four times with 1% (vol/vol) Acetic Acid.

10. Store the plates at 370 incubator to facilitate faster drying.
11. Once the plates are completely dry, add 200 μL of 10 mM Tris base solution (pH 10.5) to each well. Leave at room temperature for 30 minutes for SRB to solubilize.
12. Measure the OD at 500 nm in a microplate reader.
13. Calculate the percentage of cell-growth inhibition using the next formula:

% of control cell growth=100×($OD_{sample}$−mean $OD_{day0}$)/($OD_{neg\ control}$−mean $OD_{day0}$)

For $GI_{50}$ determination, plot a dose-response curves between the compound concentration and percent of growth inhibition. $GI_{50}$ values can be derived by fitting dose-response curves using sigmoidal dose response equation.

| CELL LINE | Medium | Seeding Density | Dissociation Agent |
|---|---|---|---|
| HCT 116 - Colon | RPMI, 10% FBS, 1X Pen/Strep | 800 cells/well | Trypsin |
| HCT 15 - Colon | RPMI, 10% FBS, 1X Pen/Strep | 1600 cells/well | Trypsin |
| BT549 | RPMI, 10% FBS, 1X Pen/Strep | 4000 cells/well | Tryple Express (Invitrogen) |
| HS 578 - Breast | RPMI, 10% FBS, 1X Pen/Strep | 4000 cells/well | Tryple Express (Invitrogen) |
| PC3 - Prostate | F12K, 10% FBS, 1X Pen/Strep | 2500 cells/well | Trypsin |
| DU145 - Prostate | MEM, 10% FBS, 1X Pen/Strep | 800 cells/well | Trypsin |
| H23 - Lung | RPMI, 10% FBS, 1X Pen/Strep | 6000 cells/well | Trypsin |
| A549- Lung | RPMI, 10% FBS, 1X Pen/Strep | 1500 cells/well | Trypsin |

Representative compounds of the invention typically have activity against one or more of the above cell lines with a $GI_{50}$ of less than about 2 μm. Some representative compounds of the invention have activity against one or more of the above cell lines with a $GI_{50}$ of less than about 1 μm. Still other representative compounds of the invention have activity against one or more of the above cell lines with a $GI_{50}$ of less than about 0.1 μm.

Data for representative compounds of the invention from Test A are shown in the following table.

TABLE 1

| | GI50 (μM) | | | | | | |
|---|---|---|---|---|---|---|---|
| | Lung | | Prostate | | Colon | | Breast |
| | A549 | NCIH23 | Du145 | PC3 | HCT116 | HCT15 | Hs578 |
| Example 1 | 4.404 | | 1.242 | | 2.560 | | 4.684 |
| Example 2 | >20 | | 15.708 | | >20 | | >20 |
| Example 3 | >20 | | 1.306 | | >20 | | >20 |
| Example 4 | >20 | | 0.729 | | >20 | | 2.522 |
| Example 5 | 0.088 | 4.198 | 0.007 | 0.091 | 0.078 | 0.020 | 0.049 |
| Example 6 | 0.045 | 4.100 | 0.009 | 0.067 | 0.049 | 0.078 | 0.101 |
| Example 7 | >20 | 2.505 | 0.630 | 1.275 | >20 | 2.436 | 1.275 |
| Example 8 | 0.409 | 4.389 | 0.019 | 0.104 | 0.484 | 0.208 | 0.294 |
| Example 9 | 2.594 | 2.490 | 0.094 | 0.194 | 3.690 | 0.224 | 1.942 |
| Example 10 | >20 | >20 | >20 | >20 | >20 | >20 | >20 |
| Example 11 | 0.252 | 0.028 | 0.030 | 0.052 | 0.447 | 0.030 | 0.053 |
| Example 12 | 0.073 | 0.697 | 0.036 | 0.150 | 0.092 | 0.086 | 0.264 |
| Example 13 | 0.627 | 4.240 | 0.032 | 0.092 | 0.216 | 0.098 | 0.711 |
| Example 14 | 0.365 | 2.319 | 0.030 | 0.384 | 0.500 | 0.163 | 0.442 |
| Example 15 | 0.230 | 2.518 | 0.028 | 0.012 | 0.342 | 0.005 | 0.290 |
| Example 16 | 3.251 | 3.226 | 0.409 | 0.560 | 7.314 | 1.061 | 3.937 |
| Example 17 | 6.233 | 5.226 | 0.075 | 0.427 | 5.685 | 0.674 | 3.056 |
| Example 18 | 4.858 | | 0.387 | | >20 | | >20 |
| Example 19 | 12.854 | | 0.581 | | >20 | | 19.150 |
| Example 20 | 0.109 | 4.302 | 0.005 | 0.075 | 0.039 | 0.057 | 0.175 |
| Example 21 | 0.061 | 4.700 | 0.009 | 0.083 | 0.009 | 0.018 | 0.132 |
| Example 22 | 0.195 | 2.607 | 0.009 | 0.176 | 0.453 | 0.111 | 0.315 |
| Example 23 | 0.060 | 4.637 | 0.005 | 0.087 | 0.018 | 0.039 | 0.177 |
| Example 24 | 0.379 | 2.950 | 0.066 | 0.105 | 0.145 | 0.179 | 0.813 |
| Example 25 | 0.902 | 4.983 | 0.024 | 0.175 | 1.265 | 0.361 | 0.566 |
| Example 26 | >20 | 7.620 | 0.887 | 2.113 | >20 | 3.591 | 2.113 |
| Example 27 | 0.126 | 1.597 | 0.010 | 0.060 | 0.255 | 0.065 | 0.356 |
| Example 28 | 2.468 | 5.016 | 0.138 | 0.263 | 1.417 | 0.290 | 13.175 |
| Example 29 | 15.190 | 13.230 | 10.000 | >20 | >20 | 8.146 | >20 |
| Example 30 | 0.375 | 2.016 | 0.013 | 0.035 | 0.275 | 0.081 | 1.643 |
| Example 31 | 1.052 | 5.259 | 0.054 | 1.203 | 1.961 | 0.632 | 1.582 |
| Example 32 | 0.378 | 4.538 | 0.018 | 0.118 | 0.101 | 0.148 | 0.109 |

Representative compounds of the invention are also found to inhibit adenosine kinase from Mycobacterium. Accordingly, in one embodiment, the invention also provides a method for inhibiting an adenosine kinase (e.g. an adenosine kinase from Mycobacterium) comprising contacting the adenosine kinase with a compound of formula I or a pharmaceutically acceptable salt thereof.

In another embodiment, the invention also provides a method for treating a disease associated with adenosine kinase activity in an animal comprising administering to an animal (e.g. a mammal such as a human) in need of such therapy, an effective adenosine kinase inhibiting amount of a compound of formula I or a pharmaceutically acceptable salt thereof. Diseases associated with adenosine kinase activity may include inflammation, sepsis, arthritis, rheumatoid arthritis, osteoarthritis, autoimmune diseases, burns, adult respiratory distress syndrome, inflammatory bowel syndrome, necrotizing enterocolitis, chronic obstructive pulmonary disease, psoriasis, conjunctivitis, iridocyclitis, ischemia, reperfusion injury, peripheral vascular disease, pancreatitis, atherosclerosis, meningitis, vasculitis, dermatitis, myositis, renal inflammation, sepsis, septicemia (e.g. endotoxemia), and septic shock (e.g. endotixic shock).

In another embodiment, the invention also provides a method for treating tuberculosis in an animal (e.g. a mammal such as a human) comprising administering a compound of formula I or a pharmaceutically acceptable salt thereof to the animal.

In another embodiment, the invention also provides the use of a compound of formula I or a pharmaceutically acceptable salt thereof to prepare a medicament for inhibiting an adenosine kinase in an animal (e.g. a mammal such as a human).

In another embodiment, the invention also provides the use of a compound of formula I or a pharmaceutically acceptable salt thereof to prepare a medicament for treating a disease associated with adenosine kinase activity in an animal (e.g. a mammal such as a human).

In another embodiment, the invention also provides the use of a compound of formula I or a pharmaceutically acceptable salt thereof to prepare a medicament for treating tuberculosis in an animal (e.g. a mammal such as a human).

| Abbreviations | |
|---|---|
| AcOEt | ethylacetate |
| Boc | tert-butoxycarbonyl |
| bd | broad doublet |
| bs | broad singlet |
| Bu | butyl |
| Bz | benzoyl |
| calcd | calculated |
| cat. | catalyst |
| d | doublet |
| dd | doublet of doublets |
| ddd | doublet of doublet of doublets |
| DMF | dimethylformamide |
| DMSO | dimethylsulfoxide |
| dt | doublet of triplets |
| Et | ethyl |
| EDTA | ethylenediaminetetraacetic acid |
| FAB | fast atom bombardment |
| gem | geminal |
| HR | high resolution |
| i | ipso |
| IR | infrared spectroscopy |
| m | multiplet |
| m | meta |
| Me | methyl |
| MeOH | methanol |
| MeONa | sodium methoxide |
| MS | mass spectrometry |
| v | wave number |
| NMR | nuclear magnetic resonance |
| o | ortho |
| p | para |
| Ph | phenyl |
| PPh$_3$ | triphenylphosphine |
| Py | pyridyl |
| pyrr | pyrrolyl |
| q | quartet |
| rel. | relative |
| RT | room temperature |
| s | singlet |
| sat. | saturated |
| sol. | solution |
| t | triplet |
| TBS | tert-butyldimethylsilyl |
| td | triplet of doublets |
| TDA-1 | tris[2-(2-methoxyethoxy)ethyl]amine |
| THF | tetrahydrofuran |
| TFA | trifluoroacetic acid |
| TPPTS | sodium triphenylphosphine trisulfonate |
| Tr | trityl, triphenylmethyl |
| vic | vicinal |

The invention will now be illustrated by the following non-limiting Examples.

EXAMPLES

Example 1

4-Ethyl-7-(β-D-ribofuranosyl)-7H-pyrrolo[2,3-d]pyrimidine (3a)

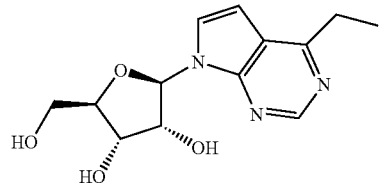

Compound 2a (149 mg, 0.34 mM) is treated with 90% aqueous TFA (0.5 mL) for 1 h at RT. The volatiles are removed in vacuo and the residue is several times co-evaporated with MeOH. Chromatography on silica (3.5%→4% MeOH in CHCl$_3$) affords nucleoside 3a (100 mg, quantitative) as colorless glassy solid. $^1$H NMR (600 MHz, DMSO-d$_6$): 1.30 (t, 3H, J$_{vic}$=7.6, CH$_3$CH$_2$); 2.99 (q, 2H, J$_{vic}$=7.6, CH$_2$CH$_3$); 3.54 (ddd, 1H, J$_{gem}$=11.9, J$_{5'b,OH}$=5.8, J$_{5'b,4'}$=4.0, H-5'b); 3.63 (ddd, 1H, J$_{gem}$=11.9, J$_{5'a,OH}$=5.3, J$_{5'a,4'}$=4.0, H-5'a); 3.91 (q, 1H, J$_{4',5'}$=4.0, J$_{4',3'}$=3.3, H-4'); 4.11 (td, 1H, J$_{3',2'}$=5.1, J$_{3',OH}$=4.8, J$_{3',4'}$=3.3, H-3'); 4.43 (td, 1H, J$_{2',OH}$=6.5, J$_{2',1'}$=6.3, J$_{2',3'}$=5.1, H-2'); 5.13 (t, 1H, J$_{OH,5'}$=5.8, 5.3, OH-5'); 5.19 (d, 1H, J$_{OH,3'}$=4.8, OH-3'); 5.35 (d, 1H, J$_{OH,2'}$=6.5, OH-2'); 6.18 (d, 1H, J$_{1',2'}$=6.3, H-1'); 6.77 (dd, 1H, J$_{5,6}$=3.7, J$_{5,2}$=0.4, H-5); 7.78 (d, 1H, J$_{6,5}$=3.7, H-6); 8.69 (s, 1H, H-2). $^{13}$C NMR (151 MHz, DMSO-d$_6$); 12.93 (CH$_3$CH$_2$); 27.97 (CH$_2$CH$_3$); 61.87 (CH$_2$-5'); 70.87 (CH-3'); 74.18 (CH-2'); 85.38 (CH-4'); 87.02 (CH-1'); 100.09 (CH-5); 117.38 (C-4a); 126.78 (CH-6); 150.73 (C-7a); 151.15 (CH-2); 163.77 (C-4). MS FAB, m/z (rel. %): 149 (45), 280 (100) [M+H], HR MS (FAB): calcd for C$_{13}$H$_{18}$N$_3$O$_4$ [M+H] 280.1297. found 280.1293.

The intermediate compound 2a is prepared as follows.

a. 4-Ethyl-7-{2,3-O-isopropylidene-5-O-(tert-butyldimethylsilyl)-β-D-ribofuranosyl}-7H-pyrrolo[2,3-d]pyrimidine (2a). An argon purged mixture of protected chlorodeazapurine riboside 1 (200 mg, 0.454 mM), triethylaluminiuum (1M sol. in THF, 910 μL 0.91 mM) and Pd(PPh$_3$)$_4$ (26 mg, 0.022 mM) in THF (5 mL) is stirred at 70° C. for 20 h. The mixture is diluted with hexane (30 ml) and washed with aqueous NH$_4$Cl (sat., 10 mL), aqueous phase is re-extracted with hexane (2×10 mL). Collected organic extracts are dried over MgSO$_4$, volatiles are removed in vacuo and the residue is chromatographed on silica (hexanes-AcOEt, 10:1→6:1) affording product 2a as colorless oil (162 mg, 82%). $^1$H NMR (600 MHz, CDCl$_3$): 0.046 and 0.053 (2×s, 2×3H, CH$_3$Si); 0.90 (s, 9H, (CH$_3$)$_3$C); 1.39 (q, 3H, J=0.6, (CH$_3$)$_2$C); 1.393 (t, 3H, J$_{vic}$=7.7, CH$_3$CH$_2$); 1.65 (q, 3H, J=0.6, (CH$_3$)$_2$C); 3.04 (q, 2H, J$_{vic}$=7.7, CH$_2$CH$_3$); 3.79 (dd, 1H, J$_{gem}$=11.2, J$_{5'b,4'}$=4.0, H-5'b); 3.87 (dd, 1H, J$_{gem}$=1.2, J$_{5'a,4'}$=3.8, H-5'a); 4.33 (m, 1H, J$_{4',5'}$=4.0, 3.8, J$_{4',3'}$=3.1, J$_{4',2'}$=0.4, H-4'); 4.98 (ddd, 1H, J$_{3',2'}$=6.3, J$_{3',4'}$=3.1, J$_{3',1'}$=0.5, H-3'); 5.13 (ddd, 1H, J$_{2',3'}$=6.3, J$_{2',1'}$=3.1, J$_{2',4'}$=0.4, H-2'); 6.41 (d, 1H, J$_{1',2'}$=3.1, H-1'); 6.58 (d, 1H, J$_{5,6}$=3.7, H-5); 7.43 (d, 1H, J$_{6,5}$=3.7, H-6); 8.81 (s, 1H, H-2). $^{13}$C NMR (151 MHz, CDCl$_3$): −5.50 and −5.40 (CH$_3$Si); 12.87 (CH$_3$CH$_2$); 18.37 (C(CH$_3$)$_3$); 25.47 ((CH$_3$)$_2$C); 25.90 ((CH$_3$)$_3$C); 27.34 ((CH$_3$)$_2$C); 28.61 (CH$_2$CH$_3$); 63.37 (CH$_2$-5'); 80.94 (CH-3'); 84.80 (CH-2'); 85.96 (CH-4'); 90.17 (CH-1'); 100.09 (CH-5); 114.11 (C(CH$_3$)$_2$); 117.70 (C-4a); 125.60 (CH-6); 150.39 (C-7a); 1551.64 (CH-2); 164.25 (C-4).

Example 2

4-Benzyl-7-(β-D-ribofuranosyl)-7H-pyrrolo[2,3-d]pyrimidine (3b)

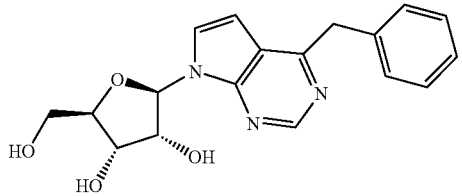

Compound 2b (183 mg, 0.37 mM) is treated with 90% aqueous TFA (0.5 mL) for 1 h at RT. The volatiles are removed in vacuo and the residue is several times co-evaporated with MeOH. Chromatography on silica (3% MeOH in CHCl$_3$) affords nucleoside 3b (107 mg, 85%) as colorless glassy solid. $^1$H NMR (400 MHz, DMSO-d$_6$): 3.55 and 3.63 (2×dd, 2H, J$_{gem}$=111.9, J$_{5',4'}$=3.9, H-5'); 3.93 (q, 1H, J$_{4',5'}$=3.9, J$_{4',3'}$=3.2, H-4'); 4.11 (dd, 1H, J$_{3',2'}$=5.0, J$_{3',4'}$=3.2, H-3'); 4.42 (dd, 1H, J$_{2',1'}$=6.1, J$_{2',3'}$=5.0, H-2'); 4.43 (s, 2H, CH$_2$Ph); 4.7-5.3 (bs, 3H, OH-2',3',5'); 6.21 (d, 1H, J$_{1',2'}$=6.1, H-1'); 6.90 (d, 1H, J$_{5,6}$=3.7, H-5); 7.22 (m, 1H, H-p-Ph); 7.29 (m, 2H, H-m-Ph); 7.38 (m, 2H, H-o-Ph); 7.94 (d, 1H, J$_{6,5}$=3.7, H-6); 8.87 (s, 1H, H-2). $^{13}$C NMR (100.6 MHz, DMSO-d$_6$): 39.91 (CH$_2$Ph); 61.67 (CH$_2$-5'); 70.78 (CH-3'); 74.32 (CH-2'); 85.60 (CH-4'); 87.11 (CH-1'); 101.30 (CH-5); 117.64 (C-4a); 126.92 (CH-p-Ph); 128.48 (CH-6); 128.76 (CH-m-Ph); 129.25 (CH-o-Ph); 137.66 (C-i-Ph); 149.22 (CH-2); 151.01 (C-7a); 159.30 (C-4). MS FAB, m/z (rel. %): 210 (100), 342 (85)[M+H]. HR MS (FAB): calcd for C$_{18}$H$_{20}$N$_3$O$_4$ [M+H] 342.1454. found 342.1467.

The intermediate compound 2b is prepared as follows.

a. 4-Benzyl-7-{2,3-O-isopropylidene-5-O-(tert-butyldimethylsilyl)-β-D-ribofuranosyl}-7H-pyrrolo[2,3-d]pyrimidine (2b). An argon purged mixture of protected chlorodeazapurine riboside 1 (191 mg, 0.43 mM), benzylzine bromide (0.5M sol. in THF, 1.75 mL, 0.875 mM) and Pd(PPh$_3$)$_4$ (25 mg, 0.022 mM) in THF (5 mL) is stirred at 70° C. for 24 h. The mixture is diluted with hexane (25 mL) and washed with aqueous NH$_4$Cl (sat., 10 mL), aqueous phase is re-extracted with hexane (2×10 mL). Collected organic extracts are dried over MgSO$_4$, volatiles are removed in vacuo and the residue is chromatographed on silica (hexanes-AcOEt, 6:1) affording product 2b as colorless oil (201 mg, 93%). $^1$H NMR (400 MHz, CDCl$_3$): 0.02 and 0.04 (2×s, 2×3H, CH$_3$Si); 0.88 (s, 9H, (CH$_3$)$_3$C); 1.38 (q, 3H, J=0.6, (CH$_3$)$_2$C); 1.64 (q, 3H, J=0.6, (CH$_3$)$_2$C); 3.77 (dd, 1H, J$_{gem}$=11.2, J$_{5'b,4'}$=4.0, H-5'b); 3.86 (dd, 1H, J$_{gem}$=11.2, J$_{5'a,4'}$=3.8, H-5'a); 4.31 (q, 1H, J$_{4',5'}$=4.0, 3.8, J$_{4',3'}$=3.1, H-4'); 4.35 (s, 2H, CH$_2$Ph); 4.96 (ddd, 1H, J$_{3',2'}$=6.3, J$_{3',4'}$=3.1, J$_{3',1'}$=0.4, H-3'); 5.10 (dd, 1H, J$_{2',3'}$=6.3, J$_{2',1'}$=3.1, H-2'); 6.39 (d, 1H, J$_{1',2'}$=3.1, H-1); 6.43 (d, 1H, J$_{5,6}$=3.7, H-5); 7.21 (m, 1H, H-p-Ph); 7.25-7.33 (m, 4H, H-o,m-Ph); 7.39 (d, 1H, J$_{6,5}$=3.7, H-6); 8.83 (s, 1H, H-2). $^{13}$C NMR (100.6 MHz, CDCl$_3$): −5.50 and −5.40 (CH$_3$Si); 18.37 (C(CH$_3$)$_3$); 25.47 ((CH$_3$)$_2$C); 25.90 ((CH$_3$)$_3$C); 27.34 ((CH$_3$)$_2$C); 42.27 (CH$_2$Ph); 63.38 (CH$_2$-5'); 80.96 (CH-3'); 84.79 (CH-2'); 85.99 (CH-4'); 90.21 (CH-1'); 100.37 (CH-5); 114.15 (C(CH$_3$)$_2$); 118.28 (C-4a); 126.00 (CH-6); 126.60 (CH-p-Ph); 128.57 and 129.07 (CH-o,m-Ph); 138.11 (C-i-Ph); 150.81 (C-7a); 151.65 (CH-2); 161.14 (C-4). MS FAB, m/z (rel. %): 73 (100), 210 (30), 292 (10), 496 (95)[M+H]. HR MS (FAB): calcd for C$_{27}$H$_{38}$N$_3$O$_4$Si [M+H] 496.2632. found 496.2636.

Example 3

4-(4-Methoxyphenyl)-7-(β-D-ribofuranosyl)-7H-pyrrolo[2,3-d]pyrimidine (3d)

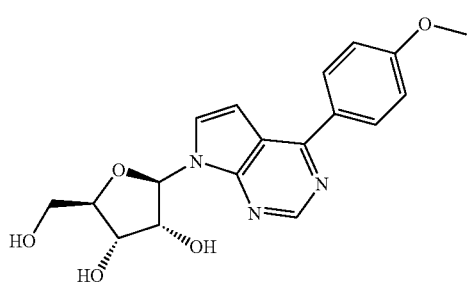

Compound 2d (463 mg, 0.90 mM) is treated with 90% aqueous TFA (1 mL) for 1 h at RT. The volatiles are removed in vacuo and the residue is several times co-evaporated with MeOH. Chromatography on silica (5%→6% MeOH in CHCl$_3$) affords crude nucleoside 3d (405 mg, 125%), which is re-purified by reverse phase chromatography providing desired product (200 mg, 62%) as colorless glassy solid. $^1$H NMR (500 MHz, DMSO-d$_6$); 3.57 and 3.66 (2×dd, 2H, J$_{gem}$=11.9, J$_{5',4'}$=4.0, H-5'); 3.87 (s, 3H, CH$_3$O); 3.94 (td, 1H, J$_{4',5'}$=4.0, J$_{4',3'}$=3.3, H-4'); 4.14 (dd, 1H, J$_{3',2'}$=5.1, J$_{3',4'}$=3.3, H-3'); 4.46 (dd, 1H, J$_{2',1'}$=6.2, J$_{2',3'}$=5.1, H-2'); 6.28 (d, 1H, J$_{1',2'}$=6.2, H-1'); 7.03 (d, 1H, J$_{5,6}$=3.8, H-5); 7.16 (m, 2H, H-M-C$_6$H$_4$OMe); 7.97 (d, 1H, J$_{6,5}$=3.8, H-6); 8.17 (m, 2H, H-o-C$_6$H$_4$OMe); 8.86 (s, 1H, H-2). $^{13}$C NMR (125.7 MHz, DMSO-d$_6$): 55.58 (CH$_3$O); 61.73 (CH$_2$-5'); 70.77 (CH-3'};

74.29 (CH-2'); 85.42 (CH-4'); 86.97 (CH-1'); 101.43 (CH-5); 114.59 (CH-m-$C_6H_4$OMe); 114.94 (C-4a); 128.16 (CH-6); 129.38 (C-i-$C_6H_4$OMe); 150.59 (CH-2); 152.00 (C-7a); 155.47 (C-4); 161.39 (C-p-$C_6H_4$OMe). MS FAB, m/z (rel. %): 226 (100), 240 (30), 268 (20), 358 (15)[M+H]. HR MS (FAB): calcd for $C_{18}H_{20}N_3O_5$ [M+H] 358.1403. found 358.1414.

The intermediate compound 2d is prepared as follows.

a. 7-{2,3-O-Isopropylidene-5-O-(tert-butyldimethylsilyl)-β-D-ribofuranosyl}-4-(4-methoxyphenyl)-7H-pyrrolo[2,3-d]pyrimidine (2d). An argon purged mixture of chlorodeazapurine riboside 1 (415 mg, 0.94 mM), 4-methoxyphenylboronic acid (215 mg, 1.41 mM), $K_2CO_3$ (195 mg, 1.4 mM) and Pd(PPh$_3$)$_4$ (55 mg, 0.047 mM) in toluene (5 mL) is stirred at 100° C. for 5 h. The mixture is diluted with chloroform (20 mL) and washed with aqueous NH$_4$Cl (sat., 20 mL), aqueous phase is re-extracted with chloroform (2×5 mL). Collected organic extracts are dried over MgSO$_4$, volatiles are removed in vacuo and the residue is chromatographed on silica (hexanes-AcOEt, 7:1) affording product 2d as yellowish oil (482 mg, 100%). $^1$H NMR (600 MHz, CDCl$_3$): 0.06 and 0.07 (2×s, 2×3H, CH$_3$Si); 0.90 (s, 9H, (CH$_3$)$_3$C); 1.40 and 1.67 (2×q, 2×3H, J=0.6, (CH$_3$)$_2$C); 3.81 (dd, 1H, $J_{gem}$=11.1, $J_{5'b,4'}$=0.9, H-5'b); 3.90 (dd, 1H, $J_{gem}$=11.1, $J_{5'a,4'}$=3.8, H-5'a); 3.90 (s, 3H, CH$_3$O); 4.35 (ddd, 1H, $J_{4,5}$=3.9, 3.8, $J_{4',3}$=3.2, H-4'); 5.00 (ddd, 1H, $J_{3',2'}$=6.3, $J_{3',4'}$=3.2, $J_{3',1'}$=0.4, H-3); 5.15 (dd, 1H, $J_{2',3'}$=66.3, $J_{2',1'}$=3.0, H-2'); 6.48 (d, 1H, $J_{1',2'}$=3.0, H-1); 6.83 (d, 1H, $J_{5,6}$=3.8, H-5); 7.07 (m, 2H, H-m-$C_6H_4$OMe); 7.53 (d, 1H, $J_{6,5}$=3.8, H-6); 8.09 (m, 2H, H-o-$C_6H_4$OMe); 8.93 (s, 1H, H-2). $^{13}$C NMR (151 MHz, CDCl$_3$): −5.48 and −5.37 (CH$_3$Si); 18.39 (C (CH$_3$)$_3$); 25.49 ((CH$_3$)$_2$C); 25.92 ((CH$_3$)$_3$C); 27.36 ((CH$_3$)$_2$C); 55.40 (CH$_3$O); 63.39 (CH$_2$-5'); 80.93 (CH-3'); 84.93 (CH-2'); 86.03 (CH-4'); 90.22 (CH-1'); 101.51 (CH-5); 114.13 (C(CH$_3$)$_2$); 114.18 (CH-m-$C_6H_4$OMe); 115.85 (C-4a); 126.38 (CH-6); 130.32 (CH-o-$C_6H_4$OMe); 130.65 (C-i-$C_6H_4$OMe); 151.59 (C-7a); 151.66 (CH-2); 157.21 (C-4); 161.23 (C-p-$C_6H_4$OMe). MS FAB, m/z (rel. %): 73 (100), 226 (25), 512 (45)[M+H]. HR MS (FAB): calcd for $C_{27}H_{38}N_3O_5Si$ [M+H] 512.2581. found 512.2575.

Example 4

4-(4-Fluorophenyl)-7-(β-D-ribofuranosyl)-7H-pyrrolo[2,3-d]pyrimidine (3e)

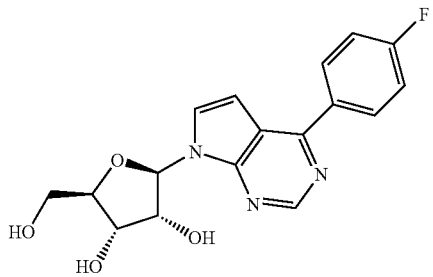

Compound 2e (328 mg, 0.66 mM) is treated with 90% aqueous TFA (0.5 mL) for 1 h at RT. The volatiles are removed in vacuo and the residue is several times co-evaporated with MeOH. Chromatography on silica (5%→6% MeOH in CHCl$_3$) affords nucleoside 3e (214 mg, 94%) as white solid. Compound is crystallized from MeOH/chloroform. H NMR (500 MHz, DMSO-d$_6$): 3.57 (ddd, 1H, $J_{gem}$=11.9, $J_{5'b,OH}$=5.6, $J_{5'b,4'}$=4.0, H-5'b); 3.66 (ddd, 1H, $J_{gem}$=11.9, $J_{5'a,OH}$=5.4, $J_{5'b,4'}$=4.0, H-5'a); 3.95 (td, 1H, $J_{4',5}$=4.0, $J_{4',3}$=3.3, H-4'); 4.14 (ddd, 1H, $J_{3',2'}$=5.1, $J_{3',OH}$=4.9, $J_{3',4'}$=3.3, H-3'); 4.46 (ddd, 1H, $J_{2',OH}$=6.4, $J_{2',1'}$=6.2, $J_{2',3}$=5.1, H-2'); 5.09 (dd, 1H, $J_{OH,5}$=5.6, 5.4, OH-5'); 5.19 (d, 1H, $J_{OH,3}$=4.9, OH-3'); 5.39 (d, 1H, $J_{OH,2'}$=6.3, OH-2'); 6.29 (d, 1H, $J_{1',2'}$=6.2, H-1'); 7.02 (d, 1H, $J_{5,6}$=3.8, H-5); 7.43 (m, 2H, H-m-$C_6H_4F$); 7.98 (d, H, $J_{6,5}$=3.8, H-6); 8.25 (m, 2H, H-o-$C_6H_4F$); 8.89 (s, 1H, H-2). $^{13}$C NMR (125.7 MHz, DMSO-d$_6$): 61.73 (CH$_2$-5'); 70.76 (CH-3'); 74.25 (CH-2'); 85.39 (CH-4'); 86.92 (CH-1'); 100.98 (CH-5); 115.38 (C-4a); 116.09 (d, $J_{C,F}$=22, CH-m-$C_6H_4F$); 128.33 (CH-6); 131.13 (d, $J_{C,F}$=9, CH-o-$C_6H_4F$); 134.15 (d, $J_{C,F}$=3, C-i-$C_6H_4F$); 151.13 (CH-2); 152.17 (C-7a); 155.10 (C-4); 163.55 (d, $J_{C,F}$=248, C-p-$C_6H_4F$). $^{19}$F NMR (470.3 MHz, DMSO-d$_6$): −111.14. IR (KBr): ν=1627, 1606, 1568, 1515, 1460, 1357, 1235, 1098, 1049 cm$^{-1}$. MS FAB, m/z (rel. %): 214 (100), 346 (35)[M+H]. HR MS (FAB): calcd for $C_{17}H_{17}FN_3O_4$ [M+H] 346.1203. found 346.1212.

The intermediate compound 2e is prepared as follows.

a. 4-(4-Fluorophenyl)-7-{2,3-O-isopropylidene-5-O-(tert-butyldimethylslyl)-β-D-ribofuranosyl}-7H-pyrrolo[2,3-d]pyrimidine (2e). An argon purged mixture of chlorodeazapurine riboside 1 (409 mg, 0.93 mM), 4-fluorophenylboronic acid (195 mg, 1.39 mM), $K_2CO_3$ (192 mg, 1.39 mM) and Pd(PPh$_3$)$_4$ (54 mg, 0.047 mM) in toluene (5 mL) is stirred at 100° C. for 5 h. The mixture is diluted with chloroform (20 mL) and washed with aqueous NH$_4$Cl (sat., 20 mL), aqueous phase is re-extracted with chloroform (2×5 mL). Collected organic extracts are dried over MgSO$_4$, volatiles are removed in vacuo and the residue is chromatographed on silica (hexanes-AcOEt, 10:1→7:1) affording product 2e as colorless oil (356 mg, 77%). $^1$H NMR (600 MHz, CDCl$_3$): 0.07 and 0.08 (2×s, 2×3H, CH$_3$Si); 0.91 (s, 9H, (CH$_3$)$_3$C); 1.41 (q, 311, J=0.7, (CH$_3$)$_2$C); 1.67 (q, 3H, J=0.7, (CH$_3$)$_2$C); 3.82 (dd, 1H, $J_{gem}$11.3, $J_{5'b,4'}$=3.8, H-5 b); 3.91 (dd, 1H, $J_{gem}$=11.3, $J_{5'a,4'}$=3.6, H-5'a); 4.37 (q, 1H, $J_{4',5'}$=3.8, 3.6, $J_{4',3'}$=3.1, H-4'); 5.00 (ddd, 1H, $J_{3',2'}$=6.2, $J_{3',4'}$=3.1, $J_{3',1'}$=0.4, H-3'); 5.13 (dd, 1H, $J_{2',3}$=6.2, $J_{2',1'}$=3.1, H-2'); 6.50 (d, 1H, $J_{1',2}$=3.1, H-1'); 6.80 (d, 1H, $J_{5,6}$=3.7, H-5); 7.25 (m, 2H, H-m-$C_6H_4F$); 7.59 (d, 1H, $J_{6,5}$=3.7, H-6); 8.11 (m, 2H, H-o-$C_6H_4F$); 8.96 (s, 1H, H-2). $^{13}$C NMR (151 MHz, CDCl$_3$): −5.51 and −5.38 (CH$_3$Si); 18.38 (C(CH$_3$)$_3$); 25.45 ((CH$_3$)$_2$C); 25.89 ((CH$_3$)$_3$C); 27.35 ((CH$_3$)$_2$C); 63.38 (CH$_2$-5'); 80.85 (CH-3'); 84.96 (CH-2'); 85.95 (CH-4'); 90.18 (CH-1'); 101.15 (CH-5); 114.16 (C(CH$_3$)$_2$); 115.85 (d, $J_{C,F}$=22, CH-m-$C_6H_4F$); 116.11 (C-4a); 126.84 (CH-6); 130.73 (d, $J_{C,F}$=9, CH-o-$C_6H_4F$); 134.17 (d, $J_{C,F}$=3, C-i-CH$_4$F); 151.60 (C-7a); 151.63 (CH-2); 156.42 (C-4); 163.93 (d, $J_{C,F}$=250, C-p-$C_6H_4F$). $^{19}$F NMR (470.3 MHz, CDCl$_3$): −111.16. MS FAB, m/z (rel. %): 73 (100), 214 (20), 500 (30)[M+H]. HR MS (FAB): calcd for $C_{26}H_{35}FN_3O_4Si$ [M+H] 500.2381. found 500.2366.

Example 5

4-(Furan-2-yl)-7-(β-D-ribofuranosyl)-7H-pyrrolo[2,3-d]pyrimidine (3l)

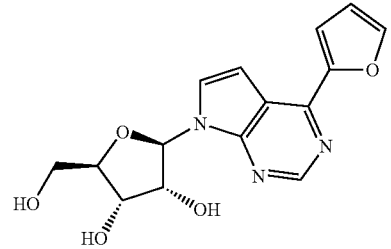

Compound 2f (276 mg, 0.58 mM) is treated with 90% aqueous TFA (0.5 mL) for 1 h at RT. The volatiles are removed in vacuo and the residue is several times co-evaporated with MeOH. Compound is crystallized from MeOH/AcOEt affording product 3f as beige powder (117 mg, 63%). $^1$H NMR (400 MHz, DMSO-$d_6$): 3.57 and 3.66 (2×dd, 2H, $J_{gem}$=11.9, $J_{5',4'}$=4.0, H-5'); 3.94 (q, 1H, $J_{4',5}$=4.0, $J_{4',3}$=3.3, H-4'); 4.13 (dd, 1H, $J_{3',2'}$=5.1, $J_{3',4'}$=3.3, H-3'); 4.45 (dd, 1H, $J_{2',1'}$=6.2, $J_{2',3'}$=5.1, H-2'); 6.25 (d, 1H, $J_{1',2'}$=6.2, H-1'); 6.80 (dd, 1H, $J_{4,3}$=3.5, $J_{4,5}$=1.7, H-4-furyl); 7.08 (d, 1H, $J_{5,6}$=3.7, H-5); 7.50 (dd, 1H, $J_{3,4}$=3.5, $J_{3,5}$=0.7, H-3-furyl); 7.95 (d, 1H, $J_{6,5}$=3.7, H-6); 8.07 (dd, 1H, $J_{5,4}$=1.7, $J_{5,3}$=0.7, H-5-furyl); 8.78 (s, 1H, H-2). $^{13}$C NMR (100.6 MHz, DMSO-$d_6$): 61.74 ($CH_2$-5'); 70.76 (CH-3'); 74.24 (CH-2'); 85.40 (CH-4'); 86.88 (CH-1'); 101.41 (CH-5); 112.79 (C-4a); 112.89 (CH-4-furyl); 113.62 (CH-3-furyl); 128.32 (CH-6); 146.36 (C-4); 146.60 (CH-5-furyl); 151.00 (CH-2); 152.24 (C-7a); 152.43 (C-2-furyl). IR (KBr): ν=1675, 1601, 1564, 1462, 1353, 1237, 1207, 1188, 1099, 1051, 1016 $cm^{-1}$. MS FAB, m/z (rel. %): 186 (100), 318 (10)[M+H]. HR MS (FAB): calcd for $C_{17}H_{17}N_3O_4$ [M+H] 318.1090. found 318.1089.

The intermediate compound 2f is prepared as follows.

f. 4-(Furan-2-yl)-7-{2,3-O-isopropylidene-5-O-(tert-butyldimethylsilyl)-β-D-ribofuranosyl}-7H-pyrrolo[2,3-d]pyrimidine (2f). An argon purged mixture of chlorodeazapurine riboside 1 (294 mg, 0.67 mM), 2-(tributylstannyl)furane (252 μL, 0.80 mM) and $PdCl_2(PPh_3)_2$ (24 mg, 0.03 mM) in DMF (3 mL) is stirred at 100° C. for 2 h. Volatiles are removed in vacuo and the residue is several times co-evaporated with toluene. Column chromatography on silica (hexanes-AcOEt, 20:1→10:1) affords product 2f as colorless foam (293 mg, 93%). $^1$H NMR (600 MHz, $CDCl_3$): 0.069 and 0.074 (2×s, 2×3H, $CH_3$Si); 0.91 (s, 9H, $(CH_3)_3$C); 1.40 and 1.67 (2×q, 2×3H, J=0.6, $(CH_3)_2$C); 3.81 (dd, 1H, $J_{gem}$=11.2, $J_{5'b,4'}$=3.7, H-5'b); 3.90 (dd, 1H, $J_{gem}$=11.2, $J_{5'a,4'}$=3.5, H-5'a); 4.36 (ddd, 1H, $J_{4',5}$=3.7, 3.5, $J_{4',3}$=3.1, H-4'); 4.99 (ddd, 1H, $J_{3',2}$=6.3, $J_{3',4'}$=3.1, $J_{3',1'}$=0.4, H-3'); 5.12 (dd, 1H, $J_{2',3}$=6.3, $J_{2',1}$=3.1, H-2'); 6.47 (d, 1H, $J_{1',2}$=3.1, H-1'); 6.64 (dd, 1H, $J_{4,3}$=3.5, $J_{4,5}$=1.7, H-4-furyl); 7.05 (d, 1H, $J_{5,6}$=3.7, H-5); 7.41 (dd, 1H, $J_{3,4}$=3.5, $J_{3,5}$=0.8, H-3-furyl); 7.56 (d, 1H, $J_{6,5}$=3.7, H-6); 7.72 (dd, 1H, $J_{3,5}$=1.7, $J_{5,3}$=0.8, H-5-furyl); 8.87 (s, 1H, H-2). $^{13}$C NMR (151 MHz, $CDCl_3$): −5.50 and −5.38 ($CH_3$Si); 18.38 (C($CH_3$)$_3$); 25.45 (($CH_3$)$_2$C); 25.90 (($CH_3$)$_3$C); 27.33 (($CH_3$)$_2$C); 63.36 ($CH_2$-5'); 80.85 (CH-3'); 84.92 (CH-2'); 85.94 (CH-4'); 90.04 (CH-1'); 102.11 (CH-5); 112.36 (CH-4-furyl); 112.97 (CH-3-furyl); 113.55 (C-4a); 114.13 (C($CH_3$)$_2$); 126.80 (CH-6); 145.11 (CH-5-furyl); 147.12 (C-4); 151.41 (CH-2); 151.82 (C-7a); 152.95 (C-2-furyl). MS FAB, m/z (rel. %): 73 (100), 186(20), 472 (45)[M+H]. HR MS (FAB): calcd for $C_{24}H_{34}N_3O_5Si$ [M+H] 472.2268. found 472.2274.

Example 6

7-(β-D-Ribofuranosyl)-4-(thiophen-2-yl)-7H-pyrrolo[2,3-d]pyrimidine (3g)

Compound 2g (200 mg, 0.41 mM) is treated with 90% aqueous TFA (0.5 mL) for 1 h at RT. The volatiles are removed in vacuo and the residue is several times co-evaporated with MeOH. The residue is crystallized from MeOH/AcOEt affording product 3g as yellow powder (85 mg, 62%). Reverse phase chromatography of mother liquors provided additional 36 mg (26%) of product. Total yield of product 3g is thus 88%. $^1$H NMR (400 MHz, DMSO-$d_6$): 3.57 and 3.66 (2×dd, 2H, $J_{gem}$=11.9, $J_{5',4'}$=4.0, H-5'); 3.94 (q, 1H, $J_{4',5}$=4.0, $J_{4',3}$=3.4, H-4'); 4.14 (dd, 1H, $J_{3',2}$=5.0, $J_{3',4}$=3.4, H-3'); 4.45 (dd, 1H, $J_{2',1}$=6.1, $J_{2',3}$=5.0, H-2'); 6.25 (d, 1H, $J_{1',2'}$=6.1, H-1'); 7.18 (d, 1H, $J_{5,6}$=3.8, H-5); 7.31 (dd, 1H, $J_{4,5}$=5.1, $J_{4,3}$=3.8, H-4-thienyl); 7.86 (dd, 1H, $J_{5,4}$=5.1, $J_{5,3}$=1.0, H-5-thienyl); 7.97 (d, 1H, $J_{6,5}$=3.8, H-6); 8.18 (dd, 1H, $J_{3,4}$=3.8, $J_{3,5}$=1.0, H-3-thienyl); 8.75 (s, 1H, H-2). $^{13}$C NMR (100.6 MHz, DMSO-$d_6$): 61.70 ($CH_2$-5'); 70.72 (CH-3'); 74.26 (CH-2'); 85.36 (CH-4'); 86.95 (CH-1'); 100.95 (CH-5); 113.12 (C-4a); 128.40 (CH-6); 129.23 (CH-4-thienyl); 129.72 (CH-3-thienyl); 130.88 (CH-5-thienyl); 142.56 (C-2-thienyl); 150.23 (C-4); 150.91 (CH-2); 152.18 (C-7a). IR (KBr): ν=1628, 1569, 1513, 1451, 1414, 1355, 1099, 1051 $cm^{-1}$. MS FAB, m/z (rel. %): 202 (45), 334 (100)[M+H]. HRMS (FAB): calcd for $C_{15}H_{16}N_3O_4S$ [M+H] 334.0862. found 334.0869.

The intermediate compound 2g is prepared as follows.

a. 7-[2,3-O-Isopropylidene-5-O-(tert-butyldimethylsilyl)-β-D-ribofuranosyl)-4-(thiophen-2-yl)-7H-pyrrolo[2,3-d]pyrimidine (2g). An argon purged mixture of chlorodeazapurine riboside 1 (208 mg, 0.47 mM), 2-(tributylstannyl)thiophene (165 μL, 0.52 mM) and $PdCl_2(PPh_3)_2$ (17 mg, 0.02 mM) in DMF (2 mL) is stirred at 100° C. for 2 h. Volatiles are removed in vacuo and the residue is several times co-evaporated with toluene. Column chromatography on silica (hexanes-AcOEt, 50:1->15:1) affords product 2g as colorless foam (219 mg, 95%). $^1$H NMR (600 MHz, $CDCl_3$): 0.070 and 0.074 (2×s, 2×3H, $CH_3$Si); 0.91 (s, 9H, $(CH_3)_3$C); 1.40 and 1.67 (2×q, 2×3H, J=0.6, $(CH_3)_2$C); 3.82 (dd, 1H, $J_{gem}$=11.2, $J_{5'b,4'}$=38, H-5'b); 3.91 (dd, 1H, $J_{gem}$=11.2, $J_{4'a,4'}$=3.6, H-5'a); 4.36 (ddd, 1H, $J_{4',5}$=3.8, 3.6, $J_{4',3}$=3.1, H-4'); 4.99 (ddd, 1H, $J_{3',2}$=6.3, $J_{3',4'}$=3.1, $J_{3',1'}$=0.4, H-3'); 5.13 (dd, 1H, $J_{2',3}$=6.3, $J_{2',1}$=3.0, H-2'); 6.47 (d, 1H, $J_{1',2'}$=3.0, H-1'); 6.91 (d, 1H, $J_{5,6}$=3.8, H-5); 7.24 (dd, 1H, $J_{4,5}$=5.0, $J_{4,3}$=3.8, H-4-thienyl); 7.57 (dd, 1H, $J_{5,4}$=5.0, $J_{5,3}$=1.1, H-5-thienyl); 7.59 (d, 1H, $J_{6,5}$=3.8, H-6); 7.97 (dd, 1H, $J_{3,4}$=3.8, $J_{3,5}$=1.1, H-3-thienyl); 8.87 (s, 1H, H-2). $^{13}$C NMR (151 MHz, $CDCl_3$): −5.50 and −5.37 ($CH_3$Si); 18.38 (C($CH_3$)$_3$); 25.45 (($CH_3$)$_2$C); 25.90 (($CH_3$)$_3$C); 27.34 (($CH_3$)$_2$C); 63.37 ($CH_2$-5'); 80.87 (CH-3'); 84.98 (CH-2'); 86.05 (CH-4'); 90.24 (CH-1'); 101.02 (CH-5); 114.00 (C-4a); 114.13 (C($CH_3$)$_2$); 126.92 (CH-6); 128.36 (CH-4-thienyl); 128.72 (CH-3-thienyl); 129.56 (CH-5-thienyl); 142.77 (C-2-thienyl); 151.04 (C-4); 151.40 (CH-2); 151.70 (C-7a). MS FAB, m/z (rel. %): 73 (100), 202 (25), 488 (43)[M+H]. HR MS (FAB): calcd for $C_{24}H_{34}N_3O_4SSi$ [M+H] 488.2039. found 488.2032.

Example 7

4-(1H-Pyrrol-2-yl)-7-(β-D-ribofuranosyl)-7H-pyrrolo[2,3-d]pyrimidine (3h)

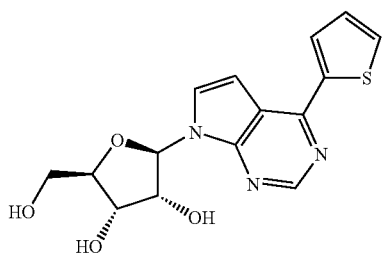

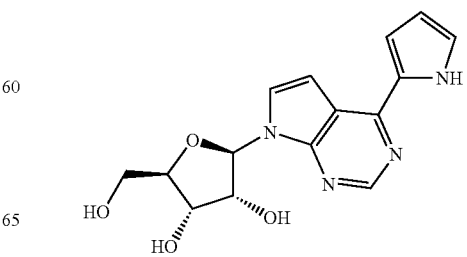

Compound 2h (385 mg, 0.67 mM) is treated with 90% aqueous TFA (0.5 mL) for 1 h at RT. The volatiles are removed in vacuo and the residue is several times co-evaporated with MeOH. The residue has crystallized after addition of little MeOH affording product 3h as yellow crystals (67 mg, 31%). Reverse phase chromatography of mother liquors provides additional product 3h (112 mg, 52%). Total yield is 83%. $^1$H NMR (500 MHz, DMSO-d$_6$): 3.57 (ddd, 1H, $J_{gem}$=11.8, $J_{5'b,OH}$=5.6, $J_{5'b,4'}$=4.0, H-5b); 3.66 (ddd, 1H, $J_{gem}$=11.8, $J_{5'a,OH}$=5.0 $J_{5'a,4'}$=4.2, H-5'a); 3.93 (ddd, 1H, $J_{4',5'}$=4.2, 4.0, $J_{4',3'}$=3.0, H-4'); 4.13 (bddd, 1H, $J_{3',2'}$=4.0, $J_{3',OH}$=3.7, $J_{3',4'}$=3.0, H-3'); 4.45 (bddd, 1H, $J_{2',1'}$=6.1, $J_{2',OH}$=4.9, $J_{2',3'}$,32 4.0, H-2'); 5.12 (dd, 1H, $J_{OH,5'}$=5.6, 5.0, OH-5r); 5.16 (bd, 1H, $J_{OH,3'}$=3.7, OH-3'); 5.35 (bd, 1H, $J_{OH,2'}$=4.9, OH-2'); 6.21 (d, 1H, $J_{1',2'}$=6.1, H-1'); 6.30 (dt, 1H, $J_{4,3}$=3.8, $J_{4,5}$=$J_{4,NH}$=2.4, H-4-pyrr); 7.037 (d, 1H, $J_{5,6}$=3.8, H-5); 7.041 (ddd, 1H, $J_{5,NH}$=2.8, $J_{5,4}$=2.4, $J_{5,3}$=1.3, H-5-pyrr); 7.18 (ddd, 1H, $J_{3,4}$=3.8, $J_{3,NH}$=2.5, $J_{3,5}$=$J_{H,F}$=1.3, H-3-pyrr); 7.82 (d, 1H, $J_{6,5}$=3.8, H-6); 8.68 (s, 1H, H-2); 11.80 (bs, 1H, NH). $^{13}$C NMR (125.7 MHz, DMSO-d$_6$): 61.82 (CH$_2$-5'); 70.79 (CH-3'); 74.15 (CH-2'); 85.30 (CH-4'); 87.01 (CH-1'); 101.04 (CH-5); 112.13 (C-4a); 112.19 (CH-4-pyrr); 113.20 (CH-3-pyrr); 122.86 (CH-5-pyrr); 127.02 (CH-6); 129.11 (C-2-pyrr); 148.99 (C-4); 150.85 (CH-2); 151.66 (C-7a). IR (KBr): v=1578,1560, 1515, 1458, 1271, 1132, 1110, 1058, 1017 cm$^{-1}$. MS FAB, m/z (rel. %): 317 (100)[M+H]. HR MS (FAB): calcd for C$_{15}$H$_{17}$N$_4$O$_4$ [M+H] 317.1250. found 317.1248. Anal. Calcd for C$_{15}$H$_{16}$N$_4$O$_4$: C, 56.96; H, 5.10; N, 17.71. Found: C, 56.54; H, 5.10; N, 17.60.

The intermediate compound 2h is prepared as follows.

a. 4-{1-(tert-Butoxycarbonyl)-1H-pyrrol-2-yl)-7-{2,3-O-isopropylidene-5-O-(tert-butyldimethylsilyl)-β-D-ribofuranosyl}-7H-pyrrolo[2,3-d]pyrimidine (2h). An argon purged mixture of chlorodeazapurine riboside 1 (403 mg, 0.92 mM), 1-N-(Boc)-pyrrole-2-boronic acid (289 mg, 1.37 mM), K$_2$CO$_3$ (253 mg, 1.83 mM) and Pd(PPh$_3$)$_4$ (53 mg, 0.05 mM) in dimethoxyethane (4 mL)/H$_2$O (1 mL) is stirred at 100° C. for 4 h. The mixture is diluted with chloroform (20 mL) and washed with aqueous NH$_4$Cl (sat., 20 mL), aqueous phase is re-extracted with chloroform (2×5 mL). Collected organic extracts are dried over MgSO$_4$, volatiles are removed in vacuo and the residue is chromatographed on silica (hexanes-AcOEt, 18:1→17:1) affording product 2h as redish foam (397 mg, 76%). $^1$H NMR (500 MHz, CDCl$_3$): 0.057 and 0.063 (2×s, 2×3H, CH$_3$Si); 0.90 (s, 9H, (CH$_3$)$_3$CSi); 1.28 (s, 9H, (CH$_3$)$_3$CO); 1.40 and 1.66 (2×q, 2×3H, J=0.6, (CH$_3$)$_2$C); 3.79 (dd, 1H, $J_{gem}$=11.2, $J_{5'b,4'}$=3.9, H-5S'b); 3.89 (dd, 1H, $J_{gem}$=11.2, $J_{5'a,4'}$=3.9, H-5'a); 4.33 (td, 1H, $J_{4',5'}$=3.9, $J_{4',3'}$=3.2, H-4'; 4.99 (ddd, 1H, $J_{3',2'}$=6.5, $J_{3',4'}$=3.2, $J_{3',1'}$=0.4, H-3'); 5.13 (dd, 1H, $J_{2',3'}$=6.5, $J_{2',1'}$=2.9, H-2'); 6.33 (dd, 1H, $J_{4,3}$=3.4, $J_{4,5}$=3.2, H-4-pyrrole); 6.44 (d, 1H, $J_{1',2'}$=2.9, H-1'); 6.56 (d, 1H, $J_{5,6}$=3.8, H-5); 6.67 (dd, 1M, $J_{3,4}$=3.4, $J_{3,5}$=1.7, H-3-pyrrole); 7.46 (dd, 1H, $J_{5,4}$=3.2, $J_{5,3}$=1.7, H-5-pyrrole); 7.49 (d, 1H, $J_{6,5}$=3.8, H-6); 8.88 (s, 1H, H-2). $^{13}$C NMR (125.7 MHz, CDCl$_3$): −5.47 and −5.37 (CH$_3$Si); 18.38 (SiC(CH$_3$)$_3$); 25.51 ((CH$_3$)$_2$C); 25.91 ((CH$_3$)$_3$CSi); 27.37 ((CH$_3$)$_2$C); 27.41 ((CH$_3$)$_3$CO); 63.37 (CH$_2$-5'); 80.94 (CH-3'); 84.07 (OC(CH$_3$)$_3$); 84.95 (CH-2'); 86.01 (CH-4'); 90.23 (CH-1'); 101.25 (CH-5); 110.94 (CH-4-pyrrole); 114.15 (C(CH$_3$)$_2$); 117.35 (C-4a); 117.80 (CH-3-pyrrole); 124.98 (CH-5-pyrrole); 126.39 (CH-6); 130.83 (C-2-pyrrole); 149.07 (CO); 150.93 (C-7a); 151.16 (CH-2); 152.05 (C-4). MS FAB, m/z (rel. %) −73 (100), 471 (15), 515 (25), 571 (30)[M+H]. HR MS (FAB); calcd for C$_{29}$H$_{43}$N$_4$O$_6$Si [M+H] 571.2952. found 571.2957.

Example 8

7-(β-D-Ribofuranosyl)-4-(thiazol-2-yl)-7H-pyrrolo[2,3-d]pyrimidine (3i)

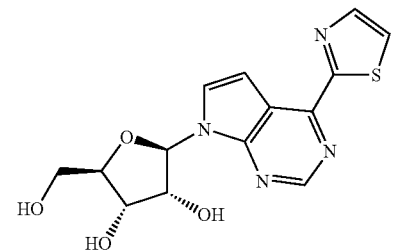

Compound 2i (459 mg, 0.94 mM) is treated with 90% aqueous TFA (1 mL) for 1 h at RT. The volatiles are removed in vacuo and the residue is several times co-evaporated with MeOH. Chromatography on silica (4% MeOH in CHCl$_3$) affords nucleoside 3i (268 mg, 85%) as yellow solid. Compound is crystallized from MeOH. $^1$H NMR (600 MHz, DMSO-d$_6$): 3.58 (ddd, 1H, $J_{gem}$=11.9, $J_{5'b,OH}$=5.6, $J_{5'b,4'}$=3.9, H-5'b); 3.66 (ddd, 1H, $J_{gem}$=1.9, $J_{5'a,OH}$=5.3, $J_{5'a,4'}$=3.9, H-5'a); 3.96 (td, 1H, $J_{4',5'}$=3.9 $J_{4',3'}$=3.3, H-4'); 4.14 (ddd, 1H, $J_{3',2'}$=5.0, $J_{3',OH}$=4.8, $J_{3',4'}$=3.3, H-3'); 4.46 (ddd, 1H, $J_{2',OH}$=6.3, $J_{2',1'}$=6.2, $J_{2',3'}$=5.0, H-2'); 5.12 (dd, 1H, $J_{OH,5'}$=5.6, 5.3, OH-5'); 5.24 (d, 1H, $J_{OH,3'}$=4.8, OH-3'); 5.44 (d, 1H, $J_{OH,2'}$=6.3, OH-5'); 6.28 (d, 1H, $J_{1',2'}$=6.2, H-1'); 7.30 (dd, 1H, $J_{5,6}$=3.7, $J_{5,2}$=0.4, H-5); 8.03 (d, 1H, $J_{6,5}$=3.7, H-6); 8.05 (d, 1H, $J_{5,4}$=3.1, H-5-thiazolyl); 8.21 (d, 1H, $J_{4,5}$=3.1, H-4-thiazolyl); 8.88 (s, 1H, H-2). $^{13}$C NMR (151 MHz, DMSO-d$_6$): 61.80 (CH$_2$-5'); 70.87 (CH-3'); 74.43 (CH-2'); 85.56 (CH-4'); 86.94 (CH-1'); 102.21 (CH-5); 113.87 (C-4a); 124.27 (CH-5-thiazolyl); 129.82 (CH-6); 145.80 (CH-4-thiazolyl); 148.24 (C-4); 151.10 (CH-2); 152.92 (C-7a); 167.50 (C-2-thiazolyl). IR (KBr): v=1631, 1574, 1510, 1453, 1403, 1121, 1088, 1034 cm$^{-1}$. MS FAB, m/z (rel. %): 203 (70), 335 (100)[M+H]. HR MS (FAB): calcd for C$_{14}$HN$_5$N$_4$O$_4$S [M+H] 335.0814. found 335.0824.

The intermediate compound 2l is prepared as follows.

a. 7-{2,3-O-Isopropylidene-5-O-(tert-butyldimethylsilyl)-β-D-ribofuranosyl}-4-(thiazol-2-yl)-7H-pyrrolo[2,3-d]pyrimidine (2i). An argon purged mixture of chlorodeazapurine riboside 1 (455 mg, 1.03 mM), 2-(tributylstannyl)thiazole (611 mg, 1.63 mM) and PdCl$_2$(PPh$_3$)$_2$ (36 mg, 0.05 mM) in DMF (3 mL) is stirred at 10000 for 16 h. Volatiles are removed in vacuo and the residue is several times co-evaporated with toluene. Column chromatography on silica (hexanes-AcOEt, 30:1→20:1) affords product 2l as colorless oil (454 mg, 90%). $^1$H NMR (600 MHz, CDCl$_3$): 0.07 and 0.08 (2×s, 2×3H, CH$_3$Si); 0.91 (s, 9H, (CH$_3$)$_3$C); 1.40 and 1.67 (2×q, 2×3H, J=0.5, (CH$_3$)$_2$C); 3.82 (dd, 1H, $J_{gem}$=11.2, $J_{5'b,4'}$=3.8, H-5'b); 3.90 (dd, 1H, $J_{gem}$=11.2, $J_{5'a,4'}$=3.6, H-5'a); 4.36 (ddd, 1H $J_{4',5'}$=3.8, 3.6, $J_{4',3'}$=3.0, H-4'); 4.99 (dd, 1H, $J_{3',2'}$=6.4, $J_{3',4'}$=3.0, H-3'); 5.11 (dd, 1H, $J_{2',3'}$=6.4 $J_{2',1'}$=3.1, H-2'); 6.50 (d, 1H, $J_{1',2'}$=3.1, H-1'); 7.41 (d, 1H, $J_{5,6}$=3.7, H-5); 7.31 (d, 1H, $J_{5,4}$=3.1, H-5-thiazolyl); 7.66 (d, 1H, $J_{6,5}$=3.7, H-6); 8.10 (d, 1H, $J_{4,5}$=3.1, H-4-thiazolyl); 8.92 (s, 1H, H-2). $^{13}$C NMR (151 MHz, CDCl$_3$): −5.49 and −5.37 (CH$_3$Si); 18.39 (C(CH$_3$)$_3$); 25.47 ((CH$_3$)$_2$C); 25.92 ((CH$_3$)$_3$C); 27.36 ((CH$_3$)$_2$C); 63.40 (CH$_2$-5'); 80.89 (CH-3'); 85.04 (CH-2'); 86.01 (CH-4'); 90.14 (CH-1'); 102.91 (CH-5); 114.17 (C(CH$_3$)$_2$); 114.69 (C-4a); 122.27 (CH-5-thiazolyl); 128.28 (CH-6); 145.11 (CH-4-thiazolyl); 148.89 (C-4); 151.18 (CH- 2); 152.45 (C-7a); 168.05 (C-2-thiazolyl). MS FAB, m/z (rel. %): 73 (100), 203 (45), 489 (80)[M+H]. HR MS (FAB): calcd for $C_{23}H_{33}N_4O_4SSi$ [M+H] 489.1992. found 489,1974.

Example 9

4-(1H-Imidazol-4-yl)-7-(β-D-ribofuranosyl)-7H-pyrrolo[2,3-d]pyrimidine (3j)

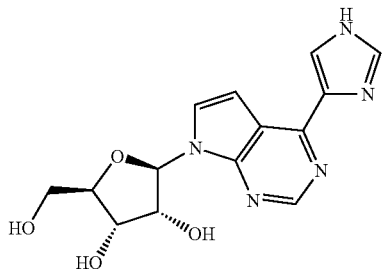

Compound 2j (448 mg, 0.63 mM) is treated with 90% aqueous TFA (1 mL) for 18 h at RT. The volatiles are removed in vacuo and the residue is several times co-evaporated with MeOH. Column chromatography on silica (1.7%→2% aq. $NH_3$ [25%], 9%→12% MeOH in $CHCl_3$) afforded nucleoside 3j (185 mg, 93%) as white hardly soluble solid. Compound is crystallized from water. $^1H$ NMR (600 MHz, DMSO-$d_6$): 3.56 (ddd, 1H, $J_{gem}$=11.8, $J_{5'b,OH}$=5.5, $J_{5'b,4'}$=4.1, H-5'b); 3.65 (ddd, 1H, $J_{gem}$=11.8, $J_{5'a,OH}$=5.5, $J_{5'a,4'}$=3.5, H-5'a); 3.93 (ddd, 1H, $J_{4',5'}$=4.1, 3.5, $J_{4',3'}$=3.4, H-4'); 4.12 (ddd, 1H, $J_{3',2'}$=5.3, $J_{3',OH}$=4.4, $J_{3',4'}$=3.4, H-3'); 4.45 (ddd, 1H, $J_2$,—F=6.2, $J_{2',OH}$=5.9, $J_{2',3'}$=5.3, H-2'); 5.13 (t, 1H, $J_{OH,5'}$=5.5, OH-5'); 5.18 (d, 1H, $J_{OH,3'}$=4.4, OH-3'); 5.37 (d, 1H, $J_{OH,2'}$=5.9, OH-2'); 6.22 (d, 1H, $J_{1',2'}$=6.2, H-1'); 7.33 (d, 1H, $J_{5,6}$=3.0, H-5); 7.77 (d, 1H, $J_{6,5}$=3.0, H-6); 7.91 (bs, 1H, H-2-imidazole); 8.03 (bs, 1H, H-5-imidazole); 8.68 (s, 1H, H-2); 12.60 (bs, 1H, NH). $^{13}C$ NMR (151 MHz, DMSO-$d_6$): 61.88 ($CH_2$-5'); 70.87 (CH-3'); 74.15 (CH-2'); 85.31 (CH-4'); 86.86 (CH-1'); 103.05 (CH-5); 113.88 (C-4a); 119.09 (CH-5-imidazole); 126.68 (CH-6); 137.37 (CH-2-imidazole); 140.45 (C-4-imidazole); 151.06 (CH-2); 152.14 and 152.19 (C-4,7a). IR (KBr). ν=1593, 1569, 1455, 1396, 1251, 1191, 1102, 1064, 1036 $cm^{-1}$. MS FAB, m/z (rel. %): 318 (100)[M+H]. HR MS (FAB): calcd for $C_{14}H_{16}N_5O_4$ [M+H] 318.1202. found 318.1191. Anal. Calcd for $C_{14}H_{15}N_5O_4 \cdot 0.35H_2O$: C, 51.96; H, 4.89; N, 21.64. Found: C, 51.74; H, 4.60; N, 21.78.

The intermediate compound 2j is prepared as follows.

a. 7-{2,3-O-Isopropylidene-5-O-(tert-butyldimethylsilyl)-β-D-ribofuranosyl}-4-(1-trityl-1H-imidazol-4-yl)-7H-pyrrolo[2,3-d]pyrimidine (2j). Ethylmagnesium bromide (1M sol. in THF, 2.3 mL, 2.3 mM) is added to an argon purged solution of 4-iodo-1-trityl-1H-imidazole (872 mg, 2 mM) in dry THF (6 mL) and the resulting solution is stirred for 10 min at ambient temperature, followed by the addition of solution of $ZnCl_2$ (1M sol. in THF, 4 mL, 4 mM). The mixture is stirred for 2 h at RT and the resulting thick white slurry is transferred to an argon purged flask with chlorodeazapurine 1 (440 mg, 1 mM) and Pd(PPh$_3$)$_4$ (58 mg, 0.05 mM) and stirred at 95° C. for 12 h. The mixture is diluted with chloroform (20 mL) and washed with aqueous EDTA (sat., 20 mL). Aqueous layer is re-extracted with chloroform (2×5 mL). Collected organic extracts are dried over $MgSO_4$, evaporated and chromatographed on silica (hexanes-AcOEt, 2.5:1) affording product 2j (474 mg, 66%) as redish foam. H NMR (500 MHz, $CDCl_3$): 0.053 and 0.056 (2×s, 2×3H, $CH_3Si$); 0.90 (s, 9H, $(CH_3)_3CSi$); 1.39 and 1.66 (2×bs, 2×34, $(CH_3)_2C$); 3.79 (dd, 14, $J_{gem}$=11.1, $J_{5'b,4'}$=3.9, H-5'b); 3.87 (dd, 1H, $J_{gem}$=11.1, $J_{5'a,4'}$=3.9, H-5'a); 4.32 (td, 1H, $J_{4',5'}$=3.9, $J_{4',3'}$=3.2, H-4'); 4.99 (dd, 1H, $J_{3',2'}$=6.4, $J_{3',4'}$=3.2, H-3'); 5.13 (dd, 1H, $J_{2',3'}$=6.4, $J_{2',1'}$=3.0, H-2'); 6.45 (d, 1H, $J_{1',2'}$=3.0, H-1'); 7.19-7.22 (m, 6H, H-o-Tr); 7.32-7.37 (m, 9H, H-m,p-Tr); 7.38 (d, 1H, $J_{5,6}$=3.8, H-5); 7.48 (d, 1H, $J_{6,5}$=3.8, H-6); 7.61 (d, 1H, $J_{2,5}$=1.4, H-2-imidazole); 7.90 (d, 1H, $J_{5,2}$=1.4, H-5-imidazole); 8.75 (s, 1H, H-2). $^{13}C$ NMR (125.7 MHz, $CDCl_3$): −5.48 and −5.36 ($CH_3Si$); 18.38 (SiC($CH_3$)$_3$); 25.50 (($CH_3$)$_2$C); 25.93 (($CH_3$)$_3$C); 27.35 (($CH_3$)$_2$C); 63.35 ($CH_2$-5'); 75.87 (C-Tr); 80.95 (CH-3'); 84.92 (CH-2'); 85.97 (CH-4'); 89.96 (CH-1'); 103.38 (CH-5); 114.06 (C(($CH_3$)$_2$); 114.81 (C-4a); 123.27 (CH-5-imidazole); 126.07 (CH-6); 128.19 (CH-m,p-Tr); 129.80 (CH-o-Tr); 140.17 (CH-2-imidazole); 140.51 (C-4-imidazole); 142.08 (C-i-Tr); 151.32 (CH-2); 151.83 (C-4); 151.92 (C-7a). MS FAB, m/z (rel. %): 243 (100), 434 (15), 714 (5)[M+H]. HR MS (FAB): calcd for $C_{42}H_{48}N_5O_4Si$ [M+H] 714.3476. found 714.3447.

Example 10

4-(Pyridin-3-yl)-7-β-D-ribofuranosyl)-7H-pyrrolo[2,3-d]pyrimidine (3k)

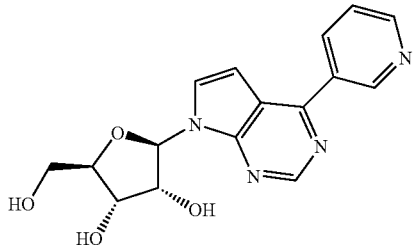

Compound 2k (359 mg, 0.74 mM) is treated with 90% aqueous TFA (0.5 mL) for 1 h at RT. The volatiles are removed in vacuo and the residue is several times co-evaporated with MeOH. Chromatography on silica (5%→6% MeOH in $CHCl_3$) afforded nucleoside 3k (270 mg, 10%) as colorless glassy solid. Crystallization from MeOH/AcOEt/hexane provided hygroscopic white powder (146 mg, 60%). Mother liquors are purified by reverse phase chromatography affording additional portion of compound 3k (57 mg, 23%) as white powder after lyophilization. Total yield of product 3k is 83%. $^1H$ NMR (600 MHz, DMSO-$d_6$): 3.58 (ddd, 1H, $J_{gem}$11.9, $J_{5'b,OH}$=5.5, $J_{5'b,4'}$=3.9, H-5'b); 3.66 (ddd, 1H, $J_{gem}$=11.9, $J_{5'a,OH}$=5.2, $J_{5'a,4'}$=3.9, H-5'a); 3.95 (td, 1H, $J_{4',5'}$=3.9, $J_{4',3'}$=3.3, H-4'); 4.15 (ddd, 1H, $J_{3,OH}$=4.7, $J_{3',2'}$=4.6, $J_{3',4'}$=3.3, H-3'); 4.47 (ddd, 1H, $J_{2',1'}$=6.2, $J_{2',OH}$=6.1, $J_{2',3'}$=4.6, H-2'); 5.13 (dd, 1H, $J_{OH,5'}$=5.5, 5.2, OH-5'); 5.25 (d, 1H, $J_{OH,3'}$=4.7, OH-3'); 5.44 (d, 1H, $J_{OH,2'}$=6.1, OH-2'); 6.30 (d, 1H, $J_{1',2'}$=6.2, H-1'); 7.08 (d, 1H, $J_{5,6}$=3.8, H-5); 7.63 (ddd, 1H, $J_{5,4}$=7.9, $J_{5,6}$=4.8, $J_{5,2}$=0.9, H-5-py); 8.02 (d, 1H, $J_{6,5}$=3.8, H-6); 8.53 (ddd, 1H, $J_{4,5}$=7.9, $J_{4,2}$=2.3, $J_{4,6}$=1.7, H-4-py); 8.76 (dd, 1H, $J_{6,5}$=4.8, $J_{6,4}$=1.7, H-6-py); 8.94 (s, 1H, H-2); 9.32 (dd, 1H, $J_{2,4}$=2.3, $J_{2,5}$=0.9, H-2-py). $^{13}C$ NMR (151 MHz, DMSO-$d_6$): 61.79 ($CH_2$-5'); 70.86 (CH-3'); 74.40 (CH-2'); 85.52 (CH-4'); 86.97 (CH-1'); 100.97 (CH-5); 115.98 (C-4a); 124.36 (CH-5-py); 128.84 (CH-6); 133.41 (C-3-py); 136.35 (CH-4-py); 149.49 (CH-2-py); 151.21 (CH-6-py); 151.36 (CH-2); 152.19 (C-7a); 153.89 (C-4). IR (KBr). ν=1679, 1566, 1517, 1457, 1420, 1206, 1132, 1087, 1045, 1030 cm$^{-1}$. MS FAB, m/z (rel. %): 329 (100)[M+H]; HR MS (FAB): calcd for $C_{16}H_{17}N_4O_4$ [M+H] 329.1250. found 329.1238.

The intermediate compound 2k is prepared as follows.

a. 7-{2,3-O-Isopylidene-5-O-(tert-butyldimethylsilyl)-β-D-ribofuranosyl}-4-pyridin-3-yl)-7H-pyrrolo[2,3-d]pyrimidine (2k). An argon purged mixture of chlorodeazapurine riboside 1 (306 mg, 0.695 mM), pyridine-3-boronic acid (128 mg, 1.04 mM), $K_2CO_3$ (192 mg, 1.39 mM) and $Pd(PPh_3)_4$ (40 mg, 0.03 mM) in dimethoxyethane (3 mL)/$H_2O$ (1 mL) is stirred at 100° C. for 3 h. The mixture is diluted with chloroform (20 mL) and washed with aqueous $NH_4Cl$ (sat., 20 mL), aqueous phase is re-extracted with chloroform (3×5 mL). Collected organic extracts are dried over $MgSO_4$, volatiles are removed in vacuo and the residue is chromatographed on silica (hexanes-AcOEt, 2:1) affording product 2k as yellowish oil (318 mg, 95%). $^1$H NMR (600 MHz, $CDCl_3$): 0.07 and 0.08 (2×s, 2×3H, $CH_3Si$); 0.91 (s, 9H, $(CH_3)_3C$); 1.41 and 1.67 (2×q, 2×3H, J=0.6, $(CH_3)_2C$); 3.82 (dd, 1H, $J_{gem}$=−11.3, $J_{5'b,4'}$=3.7, H-5'b); 3.92 (dd, 1H, $J_{gem}$=11.3, $J_{5'a,4'}$=3.6, H-5'a); 4.38 (ddd, 1H, $J_{4',5'}$=3.7, 3.6, $J_{4',3'}$=3.1, H-4'); 4.99 (ddd, 1H, $J_{3',2'}$=6.2, $J_{3',4'}$=3.1, $J_{3',1'}$=0.4, H-3'); 5.13 (dd, 1H, $J_{2',3'}$=6.2, $J_{2',1'}$=3.0, H-2'); 6.51 (d, 1H, $J_{1',2'}$=3.0, H-1'); 6.84 (d, 1H, $J_{5,6}$=3.8, H-5); 7.50 (ddd, 1H, $J_{5,4}$=7.9, $J_{5,6}$=4.6, $J_{5,2}$=0.9, H-5-py); 7.65 (d, 1H, $J_{6,5}$=3.8, H-6); 8.43 (ddd, 1H, $J_{4,5}$=7.9, $J_{4,2}$=2.2, $J_{4,6}$=1.7, H-4-py); 8.75 (dd, 1H, $J_{6,5}$=4.6, $J_{6,4}$=1.7, H-6-py); 9.01 (s, 1H, H-2); 9.33 (dd, 1H, $J_{2,4}$=2.2, $J_{2,5}$=0.9, H-2-py). $^{13}$C NMR (151 MHz, $CDCl_3$): −5.49 and −5.38 ($CH_3Si$); 18.38 ($C(CH_3)_3$); 25.47 (($CH_3)_2C$); 25.90 (($CH_3)_3C$); 27.37 (($CH_3)_2C$); 63.42 ($CH_2$-5'); 80.89 (CH-3'); 85.06 (CH-2'); 86.10 (CH-4'); 90.30 (CH-1'); 100.83 (CH-5); 114.20 ($C(CH_3)_2$); 116.54 (C-4a); 123.79 (CH-5-py); 127.48 (CH-6); 133.92 (C-3-py); 136.08 (CH-4-py); 149.81 (CH-2-py); 150.84 (CH-6-py); 151.65 (C-7a); 151.79 (CH-2); 154.63 (C-4). MS FAB, m/z (rel. %): 73 (45), 196 (35), 483 (100)[M+H]; HR MS (FAB): calcd for $C_{25}H_{35}N_4O_4Si$ [M+H] 483.2428. found 483.2433.

Example 11

4-Hydroxymethyl-7-(β-D-ribofuranosyl)-7H-pyrrolo[2,3-d]pyrimidine (3l)

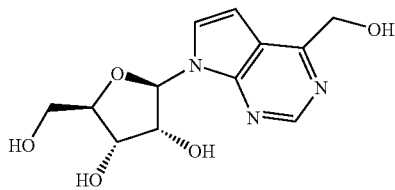

Compound 2l (326 mg, 0.75 mM) is treated with 90% aqueous TFA (1 mL) for 1 h at RT. The volatiles are removed in vacuo and the residue is several times co-evaporated with MeOH. Chromatography on silica (7%→10% MeOH in $CHCl_3$) affords free nucleoside 3l (194 mg, 92%) as yellowish glassy solid. After reverse phase chromatography the compound is crystallized from MeOH. $^1$H NMR (600 MHz, DMSO-$d_6$): 3.55 (ddd, 1H, $J_{gem}$=11.9, $J_{5'b,OH}$=5.7, $J_{5'b,4'}$=4.0, H-5'b); 3.63 (ddd, 1H, $J_{gem}$=11.9, $J_{5'a,OH}$=5.3, $J_{5'a,4'}$=4.0, H-5a); 3.92 (q, 1H, $J_{4',5'}$=4.0, $J_{4',3'}$=3.3, H-4'); 4.11 (td, 1H, $J_{3',2'}$=5.1, $J_{3,OH}$=4.8, $J_{3',4'}$=3.3, H-3'); 4.42 (td, 1H, $J_{2',OH}$=6.4, $J_{2',1'}$=6.2, $J_{2',3}$=5.1, H-2'); 4.82 (d, 2H, $J_{CH2,OH}$=5.8, $CH_2OH$); 5.08 (t, 1H, $J_{OH,5}$=5.7, 5.3, OH-5'); 5.18 (d, 1H, $J_{OH,3'}$=4.8, OH-3'); 5.35 (d, 1H, $J_{OH,2'}$=6.4, OH-2'); 5.61 (d, 2H, $J_{OH,CH2}$=5.8, HOCH$_2$); 6.21 (d, 1H, $J_{1',2'}$=6.2, H-1'); 6.88 (dd, 1H, $J_{5,6}$=3.7, $J_{5,2}$=0.4, H-5); 7.79 (d, 1H, $J_{6,5}$=3.7, H-6); 8.69 (s, 1H, H-2). $^{13}$C NMR (151 MHz, DMSO-$d_6$): 61.80 ($CH_2$-5'); 64.25 ($CH_2OH$); 70.80 (CH-3'); 74.20 (CH-2'); 85.30 (CH-4'); 86.84 (CH-1'); 101.24 (CH-5); 116.50 (C-4a); 126.71 (CH-6); 150.51 (CH-2); 151.49 (C-7a); 162.28 (C-4). IR (KBr): ν=1680, 1598, 1517, 1444, 1356, 1204, 1137, 1086 cm$^{-1}$. MS FAB, m/z (rel. %): 176 (90), 282 (100)[M+H]. HR MS (FAB): calcd for $C_{12}H_{16}N_3O_5$ [M+H] 282.1090. found 282.1083. Anal. Calcd for $C_{12}H_{15}N_3O_5$: C, 51.24; H, 5.38; N, 14.94. Found: C, 50.95; H, 5.40; N, 14.94.

The intermediate compound 2l is prepared as follows.

a. 4-(Benzoyloxymethyl)-7-[2,3-O-isopropylidene-5-O-tert-butyldimethylsily-β-D-ribofuranosyl]-7H-pyrrolo[2,3-d]pyrimidine (2l) and 4-hydroxymethyl-7-[2,3-O-isopropylidene-5-O-tert-butyldimethylsily-β-D-ribofuranosyl]-7H-pyrrolo[2,3-d]pyrimidine (2l'). To an argon purged mixture of chloro riboside 11 (440 mg, 1 mM) and $Pd(PPh_3)_4$ (58 mg, 0.05 mM) is added 0.9 M solution benzoyloxymethylzinc iodide in THF (3.33 ml, 3 mM). Mixture is stirred at ambient temperature for 15 h and then saturated $NH_4Cl$ (20 mL) is added followed by extraction with chloroform (25 mL, 2×5 mL). Organic extracts are washed with EDTA solution, dried over $MgSO_4$ and evaporated. Column chromatography of the residue on silica (hexanes-AcOt, 8:1→2:1) affords 296 mg of compound 2l (54%) and 103 mg of compound 2l' (23%). Compound 2l can be quantitatively converted to compound 2ll by treatment with 1M NaOMe/MeOH (10 mol %) for 2 h followed by neutralization with excess of Dowex 50 (pyridinium form) and evaporation. Compound 2l: Colorless oil. $^1$H NMR (600 MHz, $CDCl_3$): 0.03 and 0.04 (2×s, 2×3H, $CH_3Si$); 0.87 (s, 9H, $(CH_3)_3C$); 1.39 (q, 3H, J=0.6, $(CH_3)_2C$); 1.65 (q, 3H, J=0.6, $(CH_3)_2C$); 3.79 (dd, 1H, $J_{gem}$=11.2, $J_{5',4'}$=3.9, H-5'b); 3.87 (dd, 1H, $J_{gem}$=11.2, $J_{5a,4'}$=3.7, H-5'a); 4.34 (q, 1H, $J_{4',5'}$=3.9, 3.7, $J_{4',3}$=3.1, H-4'); 4.97 (ddd, 1H, $J_{3',2'}$=6.5, $J_{3',4'}$=3.1, $J_{3',1'}$=0.4, H-3); 5.11 (dd, 1H, $J_{2',3'}$=6.5, $J_{2',3'}$=3.0, H-2'); 5.71 (s, 2H, $CH_2O$); 6.44 (d, 1H, $J_{1',2'}$=3.0, H-1'); 6.68 (d, 1H, $J_{5,6=3.7}$, H-5); 7.46 (m, 2H, H-in-Ph); 7.50 (d, 1H, $J_{6,5}$=3.7, H-6); 7.59 (m, 1H, H-p-Ph); 8.12 (m, 2H, H-o-Ph); 8.90 (s, 1H, H-2). $^{13}$C NMR (151 MHz, $CDCl_3$): −5.52 and −5.41 ($CH_3Si$); 18.35 ($C(CH_3)_3$); 25.45 (($CH_3)_2$ C); 25.87 (($CH_3)_3C$); 27.33 (($CH_3)_2C$); 63.36 ($CH_2$-5'); 65.90 ($CH_2O$); 80.88 (CH-3'); 84.92 (CH-2'); 86.12 (CH-4'); 90.26 (CH-1'); 100.32 (CH-5); 114.17 ($C(CH_3)_2$); 117.21 (C-4a); 126.99 (CH-6); 128.50 (CH-m-Ph); 129.54 (C-i-Ph); 129.87 (CH-o-Ph); 133.31 (CH-p-Ph); 151.15 (C-7a); 151.26 (CH-2); 155.99 (C-4); 166.13 (CO). MS FAB, m/z (rel. %): 540 (100)[M+H]. HR MS (FAB): calcd for $C_{28}H_{35}N_3O_6Si$ [M+H] 540.2530. found 540.2545. Compound 2l': Yellowish oil. $^1$H NMR (600 MHz, $CDCl_3$): 0.05 and 0.06 (2×s, 2×3H, $CH_3Si$); 0.90 (s, 9H, $(CH_3)_3C$); 1.39 (q, 3H, J=0.6, $(CH_3)_2C$); 1.66 (q, 3H, J=0.6, $(CH_3)_2C$); 3.80 (dd, 1H, $J_{gem}$=11.2, $J_{5'b,4'}$=3.8, H-5b); 3.88 (dd, 1H, $J_{gem}$=1.2, $J_{5'a,4'}$=3.6, H-5'a); 4.35 (q, 1H, $J_{4',5'}$=3.8, 3.6, $J_{4',3}$=3.1, H-4'); 4.97 (ddd, 1H, $J_{3',2'}$=6.3, $J_{3',4'}$=3.1, $J_{3',1'}$=0.4, H-3'); 5.01 (s, 2H, $CH_2O$); 5.09 (dd, 1H, $J_{2',3'}$=6.3, $J_{2',1'}$=3.1, H-2'); 6.45 (d, 1H, $J_{1',2'}$=3.1, H-1); 6.57 (d, 1H, $J_{5,6}$=3.7, H-5); 7.53 (d, 1 in, $J_{6,5}$=3.7, H-6); 8.86 (s, 1H, H-2). $^{13}$C NMR (151 MHz, $CDCl_3$): −5.50 and −5.39 ($CH_3Si$); 18.38 ($C(CH_3)_3$); 25.47 (($CH_3)_2C$); 25.90 (($CH_3)_3C$); 27.36 (($CH_3)_2C$); 61.88 ($CH_2O$); 63.38 ($CH_2$-5'); 80.88 (CH-3'); 84.97 (CH-2'); 86.02 (CH-4'); 90.23 (CH-1'); 99.37 (CH-5); 114.20 ($C(CH_3)_2$); 115.41 (C-4a); 126.57 (CH-6); 150.27 (C-7a); 150.70 (CH-2); 159.27 (0-4).

Example 12

4-(Furan-3-yl)-7-(β-D-ribofuranosyl)-7H-pyrrolo[2,3-d]pyrimidine (3m)

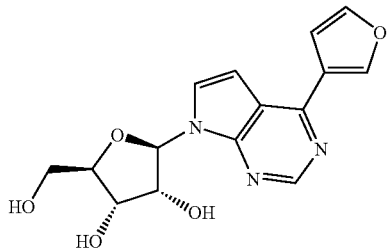

To an argon purged mixture of free riboside 4 (226 mg, 0.79 mM), furane-3-boronic acid (111 mg, 0.99 mM), $Cs_2(CO_3)_2$ (774 mg, 2.1 mM) is added a pre-prepared solution of $Pd(OAc)_2$ (9 mg, 0.04 mM) and TPPTS (56 mg, 0.099 mM) in water/$CH_3CN$ (2:1, 3 mL). The reaction mixture is stirred at 100° C. for 3 h. After cooling the mixture is neutralized by the addition of aqueous HCl (3M sol.), co-evaporated with silica and chromatographed on the column of silica (4.5% MeOH in $CHCl_3$) affording product 3m (172 mg, 69%) as yellowish solid. Compound is crystallized MeOH/$CHCl_3$/hexane as white powder. $^1H$ NMR (500 MHz, DMSO-$d_6$): 3.57 (ddd, 1H, $J_{gem}$=11.9, $J_{5'b,OH}$=5.8, $J_{5'b,4'}$=4.0, H-5'b); 3.66 (ddd, 1H, $J_{gem}$=119, $J_{5'a,OH}$=5.3, $J_{5'b,4'}$=4.0, H-5'a); 3.94 (td, 1H, $J_{4',5'}$=4.0 $J_{4',3'}$=3.4, H-4'); 4.14 (ddd, 1H, $J_{3',2'}$=5.1, $J_{3',OH}$=4.9, $J_{3',4'}$=3.4, H-3'); 4.45 (ddd, 1H, $J_{2',OH}$=6.3, $J_{2',1'}$=6.1, $J_{2',3'}$=5.1, H-2'); 5.09 (dd, 1H, $J_{OH,5'}$=5.8, 5.3, OH-5'); 5.18 (d, 1H, $J_{OH,3'}$=4.9, OH-3'); 5.37 (d, 1H, $J_{OH,2'}$=6.3, OH-2'); 6.24 (d, 1H, $J_{1',2'}$=6.1, H-1'); 7.10 (d, 1H, $J_{5,6}$=3.8, H-5); 7.26 (dd, 1H, $J_{4,5}$=1.9, $J_{4,2}$=0.8, H-4-furyl); 7.90 (dd, 1H, $J_{5,4}$=1.9, $J_{5,2}$=1.5, H-5-furyl); 7.92 (d, 1H, $J_{6,5}$=3.8, H-6); 8.74 (dd, 1H, $J_{2,5}$=1.5, $J_{2,4}$=0.8, H-2-furyl); 8.78 (s, 1H, H-2). $^{13}C$ NMR (125.7 MHz, DMSO-$d_6$): 61.73 ($CH_2$-5'); 70.73 (CH-3'); 74.20 (CH-2'); 85.32 (CH-4'); 86.92 (CH-1'); 100.86 (CH-5); 109.55 (CH-4-furyl); 114.65 (C-4a); 125.19 (C-3-furyl); 127.77 (CH-6); 144.74 (CH-5-furyl); 145.01 (CH-2-furyl); 150.15 (C-4); 151.12 (CH-2); 151.73 (C-7a). MS FAB, m/z (rel. %): 73 (100), 217 (45), 318 (55)[M+H]. HR MS (FAB): calcd for $C_{15}H_{16}N_3O_5$ [M+H] 318.1090. found 318.1086.

Example 13

7-(β-D-Ribofuranosyl)-4-(thiophen-3-yl)-7H-pyrrolo[2,3-d]pyrimidine (3n)

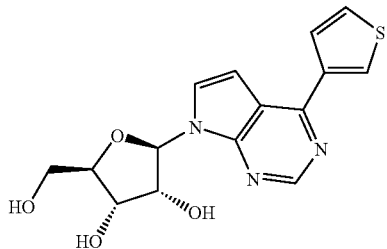

To an argon purged mixture of free riboside 4 (226 mg, 0.79 mM), thiophene-3-boronic acid (168 mg, 0.99 mM), $Cs_2(CO_3)_2$ (774 mg, 2.1 mM) is added a pre-prepared solution of $Pd(OAc)_2$ (9 mg, 0.04 mM) and TPPTS (56 mg, 0.099 mM) in water/$CH_3CN$ (2:1, 3 mL). The reaction mixture is stirred at 100° C. for 3 h. After cooling the mixture is neutralized by the addition of aqueous HCl (3M sol.), co-evaporated with silica and chromatographed on the column of silica (4.5% MeOH in $CHCl_3$) affording product 3n (176 mg, 67%) as white foam. Compound is crystallized from water as white fine needles. $^1H$ NMR (500 MHz, DMSO-$d_6$); 3.57 (ddd, 1H, $J_{gem}$11.9, $J_{5'b,OH}$=5.7, $J_{5'b,4'}$=4.0, H-5'b); 3.66 (ddd, 1H, $J_{gem}$=11.9, $J_{5'a,OH}$=5.4, $J_{5'b,4'}$=4.0, H-5'a); 3.94 (td, 1H, $J_{4',5'}$=4.0, $J_{4',3'}$=3.3, H-4'); 4.14 (ddd, 1H, $J_{3',2'}$=5.1, $J_{3,OH}$=4.8, $J_{3',4'}$=3.3, H-3'); 4.46 (ddd, 1H, $J_{2,OH}$=6.4, $J_{2',1}$=6.2, $J_{2',3}$=5.1, H-2'); 5.11 (dd, 1H, $J_{OH,5}$=5.7, 5.4, OH-5'); 5.20 (d, 1H, $J_{OH,3}$=4.8, OH-3'); 5.40 (d, 1H, $J_{OH,2}$=6.4, OH-2'); 6.26 (d, 1H, $J_{1',2'}$=6.2, H-1'); 7.16 (d, 1H, $J_{5,6}$=3.8, H-5); 7.75 (dd, 1H, $J_{5,4}$=5.0, $J_{5,2}$=2.9, H-5-thienyl); 7.95 (d, 1H, $J_{6,5}$=3.8, H-6); 7.96 (dd, 1H, $J_{4,5}$=5.0, $J_{4,2}$=1.3, H-4-thienyl); 8.55 (dd, 1H, $J_{2,5}$=2.9, $J_{2,4}$=1.3, H-2-thienyl); 8.81 (s, 1H, H-2). $^{13}C$ NMR (125.7 MHz, DMSO-$d_6$): 61.73 ($CH_2$-5'); 70.75 (CH-3'); 74.24 (CH-2'); 85.34 (CH-4'); 86.91 (CH-1'); 101.10 (CH-5); 114.68 (C-4a); 127.30 (CH-5-thienyl); 127.60 (CH-6); 128.07 (CH-4-thienyl); 128.70 (CH-2-thienyl); 140.06 (C-3-thienyl); 151.08 (CH-2); 151.59 (C-4); 152.19 (C-7a). IR (KBr): ν=1633, 1572, 1517, 1459, 1349, 1239, 1119, 1087, 1049 $cm^{-1}$. MS FAB, m/z (rel. %): 202 (55), 223 (40), 334 (100) [M+H]. HR MS (FAB): calcd for $C_{15}H_{16}N_3O_4S$ [M+H] 334.0862. found 334.0857. Anal. Calcd for $C_{15}H_{15}N_3O_4S.0.45H_2O$: C, 52.76; H, 4.69; N, 12.31. Found: C, 52.54; H, 4.43; N, 12.10.

Example 14

4-(1H-Pyrrol-3-yl)-7-(β-t-ribofuranosyl)-7H-pyrrolo[2,3-d]pyrimidine (3o)

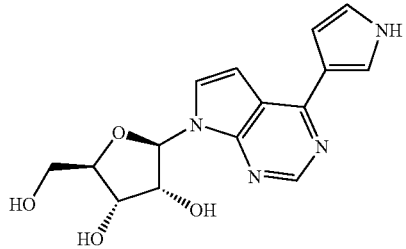

To an argon purged mixture of free riboside 4 (100 mg, 0.35 mM), 1-(triisopropylsilyl)-1H-pyrrole-3-boronic acid (112 mg, 0.42 mM), $Na_2(CO_3)_2$ (111 mg, 1.06 mM) is added a pre-prepared solution of $Pd(OAc)_2$ (4 mg, 0.018 mM) and TPPTS (25 mg, 0.044 mM) in water/$CH_3CN$ (2:1, 3 mL). The reaction mixture is stirred at 100° C. for 5 h. After cooling the mixture is neutralized by the addition of aqueous HCl (3M sol.) and purified by reverse phase chromatography affording product 3o (61 mg, 55%) as white solid. Compound is crystallized from water providing white fine needles. $^1H$ NMR (500 MHz, DMSO-$d_6$): 3.56 (ddd, 2H, $J_{gem}$=12.0, $J_{5'b,OH}$=5.9, $J_{5'b,4'}$=3.9, H-5'b); 3.65 (ddd, 2H, $J_{gem}$=12.0, $J_{5'a,OH}$=5.3, $J_{5'a,4'}$=3.9, H-5'a); 3.92 (td, 1H, $J_{4',5'}$=3.9, $J_{4',3'}$=3.4, H-4'); 4.09 (ddd, 1H, $J_{3',2'}$=5.1, $J_{3,OH}$=4.8, $J_{3',4'}$=3.4, H-3'); 4.45 (ddd, 1H, $J_{2',OH}$=6.4, $J_{2',1}$=6.2, $J_{2',3}$=5.1, H-2'); 5.13 (dd, 1H, $J_{OH,5}$=5.9, 5.3, OH-5'); 5.15 (d, 1H, $J_{OH,3}$=4.8, OH-3'); 5.34 (d, 1H, $J_{OH,2}$=6.4, OH-2'); 6.19 (d, 1H, $J_{1',2'}$=6.2, H-1'); 6.90 (td, 1H, $J_{4,5}$=$J_{4,NH}$=2.7, $J_{4,2}$=1.8, H-4- py); 6.92 (td, 1H, $J_{5,4}=J_{5,NH}=2.7$, $J_{5,2}=1.8$, H-5-pyrr); 7.01 (d, 1H, $J_{5,6}=3.8$, H-5); 7.76 (d, 1H, $J_{6,5}=3.8$, H-6); 7.77 (dt, 1H, $J_{2,NH}=2.9$, $J_{2,4}=J_{2,5}=1.8$, H-2-pyrr); 8.63 (s, 1H, H-2); 11.40 (bs, 1H, NH). $^{13}$C NMR (125.7 MHz, DMSO-$d_6$): 61.84 (CH$_2$-5'); 70.81 (CH-3'); 74.08 (CH-2'); 85.25 (CH-4'); 86.99 (CH-1'); 101.31 (CH-5); 108.11 (CH-4-pyrr); 113.47 (C-4a); 119.72 (CH-5-pyrr); 121.17 (CH-2-pyrr); 122.39 (C-3-pyrr); 126.48 (CH-6); 151.11 (CH-2); 151.57 (C-7a); 153.79 (C-4). IR (KBr): ν=1628, 1577, 1508, 1458, 1433, 1351, 1270, 1230, 1188, 1126, 1084, 1054, 1014 cm$^{-1}$. MS FAB, m/z (rel. %): 73 (100), 217 (45), 318 (55)[M+H]. HR MS (FAB): calcd for $C_{15}H_{16}N_3O_5$ [M+H] 318.1090. found 318.1086. Anal. Calcd for $C_{14}H_{15}N_5O_4 \cdot 1.45H_2O$: C, 52.61; H, 5.56; N, 16.36. Found: C, 52.79; H, 5.51; N, 16.21.

Example 15

7-(O-D-Ribofuranosyl)-4-(selenophen-2-yl)-7H-pyrrolo[2,3-d]pyrimidine (3p)

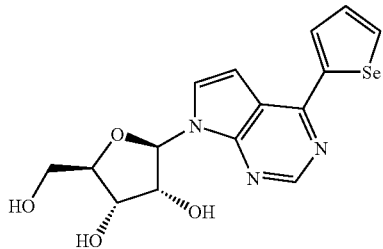

To an argon purged mixture of free riboside 4 (219 mg, 0.77 mM), selenophene-2-boronic acid (168 mg, 0.96 mM), $Cs_2(CO_3)_2$ (750 mg, 2.3 mM) is added a pre-prepared solution of Pd(OAc)$_2$ (9 mg, 0.04 mM) and TPPTS (54 mg, 0.095 mM) in water/CH$_3$CN (2:1, 3 mL). The reaction mixture is stirred at 100° C. for 3 μl. After cooling the mixture is neutralized by the addition of aqueous HCl (3M sol.), co-evaporated with silica and chromatographed on the column of silica (4.5% MeOH in CHCl$_3$) affording product 3p (188 mg, 64%) as yellow solid. Compound is crystallized from MeOH providing beige crystals. $^1$H NMR (600 MHz, DMSO-$d_6$): 3.57 (ddd, 1H, $J_{gem}=12.0$, $J_{5'b,OH}=5.8$, $J_{5'b,4'}=4.1$, H-5'b); 3.66 (ddd, 1H, $J_{gem}=12.0$, $J_{5',OH}=5.2$, $J_{5'b,4'}=4.1$, H-5'a); 3.94 (td, 1H, $J_{4',5'}=4.1$, $J_{4',3'}=3.3$, H-4'); 4.13 (td, 1H, $J_{3',2'}=J_{3',OH}=4.9$, $J_{3',4'}=3.3$, H-3'); 4.44 (ddd, 1H, $J_{2',OH}=6.3$, $J_{2',1'}=6.1$, $J_{2',3'}=4.9$, H-2'); 5.11 (dd, 1H, $J_{OH,5'}=5.8$, 5.2, OH-5'); 5.20 (d, 1H, $J_{OH,3'}=4.9$, OH-3'); 5.41 (d, 1H, $J_{OH,2'}=6.3$, OH-2'); 6.25 (d, 1H, $J_{1',2'}=6.1$, H-1'); 7.20 (d, 1H, $J_{5,6}=3.8$, H-5); 7.54 (dd, 1H, $J_{4,5}=5.6$, $J_{4,3}=4.1$, H-4-selenophenyl); 7.97 (d, 1H, $J_{6,5}=3.8$, H-6); 8.38 (dd, 1H, $J_{3,4}=4.1$, $J_{3,5}=1.0$, H-3-selenophenyl); 8.46 (dd, 1H, $J_{5,4}=5.6$, $J_{5,3}=1.0$, H-5-selenophenyl); 8.72 (s, 1H, H-2). $^{13}$C NMR (151 MHz, DMSO-$d_6$): 61.73 (CH$_2$-5'); 70.77 (CH-3'); 74.30 (CH-2'); 85.40 (CH-4'); 86.96 (CH-1'); 101.07 (CH-5); 112.44 (C-4a); 128.52 (CH-6); 131.81 (CH-3-selenophenyl); 131.99 (CH-4-selenophenyl); 136.73 (CH-5-selenophenyl); 149.41 (C-2-selenophenyl); 151.08 (CH-2); 151.57 (C-4); 152.31 (C-7a). IR (KBr): ν=1566, 1509, 1448, 1420, 1350, 1244, 1211, 1131, 1098, 1051 cm$^{-1}$. MS FAB, m/z (rel. %), 382 (100)[M+H]. HR MS (FAB): calcd for $C_{15}H_{16}N_3O_4Se$ [M+H] 382.0306. found 382.0299. Anal. Calcd for $C_{15}H_{15}N_3O_4Se$: C, 47.38; H, 3.98; N, 11.05. Found: C, 46.99; H, 3.99; N, 10.59.

Example 16

4-(1H-Pyrazol-5-yl)-7-W-D-ribofuranosyl)-7H-pyrrolo[2,3-d]pyrimidine (3q)

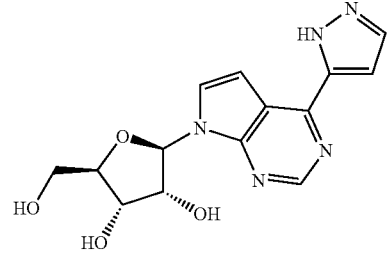

To an argon purged mixture of free riboside 4 (100 mg, 0.35 mM), 1H-pyrazole-5-boronic acid (47 mg, 0.42 mM), $Na_2(CO_3)_2$ (111 mg, 1.06 mM) is added a pre-prepared solution of Pd(OAc)$_2$ (4 mg, 0.018 mM) and TPPTS (25 mg, 0.044 mM) in water/CH$_3$CN (2:1, 3 mL). The reaction mixture is stirred at 100° C. for 5 h. After cooling the mixture is neutralized by the addition of aqueous HCl (3M sol.) and purified by reverse phase chromatography affording product 3q (71 mg, 64%) as amorphous glassy solid. Compound is lyophylized. 3H NMR (600 MHz, DMSO-$d_6$): 3.56 (ddd, 1H, $J_{gem}=11.9$, $J_{5'b,OH}=5.7$, $J_{5'b,4'}=4.0$, H-5'b); 3.63 (ddd, 1H, $J_{gem}=11.9$, $J_{5'a,OH}=5.1$, $J_{5'a,4'}=4.0$, H-5'a); 3.93 (td, 1H, $J_{4',5'}=4.0$, $J_{4',3'}=3.4$, H-4'); 4.13 (ddd, 1H, $J_{3',2'}=5.1$, $J_{3',OH}=4.9$, $J_{3',4'}=3.4$, H-3'); 4.45 (td, 1H, $J_{2',1'}=J_{2',OH}=6.2$, $J_{2',3'}=5.1$, H-2'); 5.11 (dd, 1H, $J_{OH,5'}=5.7$, 5.1, OH-5'); 5.19 (d, 1H, $J_{OH,3'}=4.9$, OH-3'); 5.39 (d, 1H, $J_{OH,2'}=6.2$, OH-2'); 6.24 (d, 1H, $J_{1',2'}=6.2$, H-1'); 7.07 (s, 1H, H-4-pyrazolyl); 7.21 (d, 1H, $J_{5,6}=3.5$, H-5); 7.86 (d, 1H, $J_{6,5}=3.5$, H-6); 7.93 (s, 1H, H-3-pyrazolyl); 8.79 (s, 1H, H-2); 13.40 (s, 1H, NH). $^{13}$C NMR (151 MHz, DMSO-$d_6$): 61.83 (CH$_2$-5'); 70.84 (CH-3'); 74.23 (CH-2'); 85.35 (CH-4'); 86.87 (CH-1'); 102.79 (CH-5); 105.17 (CH-4-pyrazolyl); 114.28 (C-4a); 127.58 (CH-6); 130.02 (CH-3-pyrazolyl); 150.70 (C-5-pyrazolyl); 150.92 (C-4); 151.15 (CH-2); 152.10 (C-7a). MS FAB, m/z (rel. %): 318 (100)[M+H]. HR MS (FAB): calcd for $C_{14}H_{16}N_5O_4$ [M+H] 318.1202. found 318.1200. Anal. Calcd for $C_{14}H_{15}N_5O_4$—$H_2O$: C, 50.15; H, 5.11; N, 20.89. Found: C, 50.04; H, 4.92; N, 20.55.

Example 17

4-(1H-Pyrazol-4-yl)-7-(β-D-ribofuranosyl)-7H-pyrrolo[2,3-d]pyrimidine (3r) and 1,4-Bis{7-(β-D-ribofuranosyl)-7H-pyrrolo[2,3-d]pyrimidin-4-yl}-1H-pyrazole (3r')

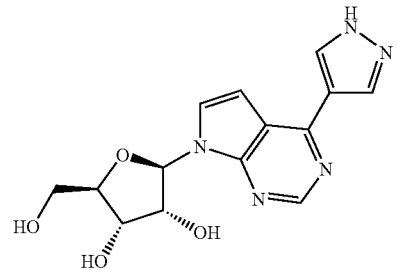

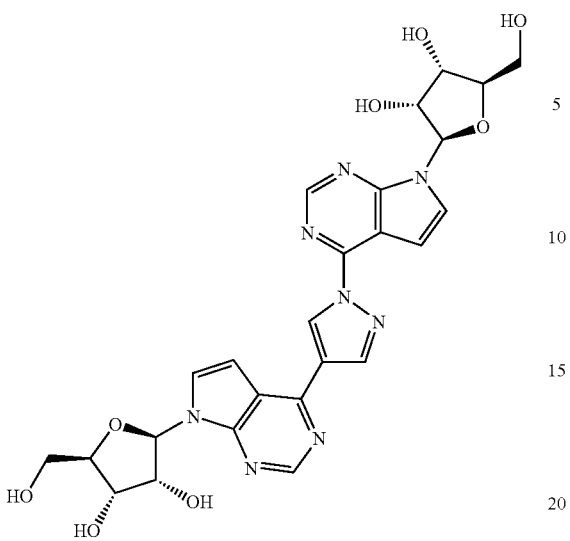

To an argon purged mixture of free riboside 4 (226 mg, 0.77 mM), pyrazole-4-boronic acid (107 mg, 0.96 mM), Cs$_2$(CO$_3$)$_2$ (753 mg, 2.3 mM) is added a pre-prepared solution of Pd(OAc)$_2$ (9 mg, 0.04 mM) and TPPTS (55 mg, 0.097 mM) in water/CH$_3$CN (2:1, 3 mL). The reaction mixture is stirred at 150° C. for 20 min in microwave oven. After cooling the mixture is neutralized by the addition of aqueous HCl (3M sol.) and purified by reverse phase chromatography providing desired 4-pyrazolyl product 3r (30 mg, 12%) as colorless glassy solid and dimer 3r'. (40 mg, 18%) as colorless solid. 3r: $^1$H NMR (600 MHz, DMSO-d$_6$): 3.56 (ddd, 1H, J$_{gem}$=11.9, J$_{5'b,OH}$=5.8, J$_{5'b,4'}$=4.0, H-5'b); 3.65 (ddd, 1H, J$_{gem}$=11.9, J$_{5'a,OH}$=5.3, J$_{5'a,4'}$=4.0, H-5'a); 3.92 (td, 1H, J$_{4',5'}$=4.0, J$_{4',3'}$=3.3, H-4'); 4.13 (ddd, 1H, J$_{3',2'}$=5.2, J$_{3',OH}$=4.9, J$_{3',4'}$=3.3, H-3'); 4.45 (ddd, 1H, J$_{2',OH}$=6.4, J$_{2',1'}$=6.2, J$_{2',3'}$=5.2, H-2'); 5.12 (dd, 1H, J$_{OH,5'}$=5.8, 5.3, OH-5'); 5.18 (d, 1H, J$_{OH,3'}$=4.9, OH-3'); 5.38 (d, 1H, J$_{OH,2'}$=6.4, OH-2'); 6.22 (d, 1H, J$_{1',2'}$=6.2, H-1'); 7.13 (dd, 1H, J$_{5,6}$=3.8, J$_{5,1}$=0.3, H-5); 7.86 (d, 1H, J$_{6,5}$=3.8, H-6); 8.35 and 8.67 (2×bs, 2×1H, H-pyrazole); 8.71 (s, 1H, H-2); 13.41 (bs, 1H, NH). $^{13}$C NMR (151 MHz, DMSO-d$_6$): 61.79 (CH$_2$-5'); 70.79 (CH-3'); 74.18 (CH-2'); 85.32 (CH-4'); 86.94 (CH-1'); 101.02 (CH-5); 113.93 (C-4a); 120.20 (C-2-pyrazole); 127.22 (CH-6); 129.80 and 139.26 (CH-3,5-pyrazole); 151.20 (CH-2); 151.21 (C-4); 151.65 (C-7a). MS FAB, m/z (rel. %): 318 (100)[M+H]. HR MS (FAB): calcd for C$_{14}$H$_6$N$_5$O$_4$ [M+H] 318.1202. found 318.1195. 3r': $^1$H NMR (600 MHz, DMSO-d$_6$): 3.58 and 3.67 (2×m, 2×2H, H-5'); 3.95 and 3.96 (2×td, 2×1H, J$_{4',5'}$=4.0, J$_{4',3'}$=3.7, H-4'); 4.15 (ddd, 2H, J$_{3',2'}$=5.0, J$_{3',OH}$=4.7, J$_{3',4'}$=3.7, H-3'); 4.46 and 4.47 (2×ddd, 2×1H, J$_{2',OH}$=6.3, J$_{2',1'}$=6.1, J$_{2',3'}$=5.0, H-2'); 5.11 and 5.12 (2×t, 2×1H, J$_{OH,5'}$=5.5, OH-5'); 5.21 and 5.24 (2×d, 2×1H, J$_{OH,3'}$=4.7, OH-3'); 5.42 and 5.45 (2×d, 2×1H, J$_{OH,2'}$=6.3, OH-2'); 6.27 and 6.31 (2×d, 2×H, J$_{1',2'}$=6.1, H-1'); 7.25 (d, 1H, J$_{5,6}$=3.8, H-5); 7.28 (dd, 1H, J$_{5,6}$=3.7, J$_{5,1}$=0.4, H-5); 7.98 (d, 1H, J$_{6,5}$=3.8, H-6); 8.00 (d, 1H, J$_{6,5}$=3.7, H-6); 8.81 and 8.84 (2×s, 2×1H, H-2); 8.88 and 9.53 (2×d, 2×1H, J=0.8, H-pyrazole). $^{13}$C NMR (151 MHz, DMSO-d$_6$): 61.72 and 61.77 (CH$_2$-5'); 70.81 (CH-3'); 74.29 and 74.46 (CH-2r); 85.42 and 85.53 (CH-4'); 86.90 and 87.05 (CH-1'); 100.85 and 102.71 (CH-5); 107.04 and 114.70 (C-4a); 123.33 (C-2-pyrazole); 128.18 and 128.23 (CH-6); 128.36 and 143.78 (CH-3,5-pyrazole); 148.36 and 149.24 (C-4); 150.58 and 151.29 (CH-2); 151.95 and 153.84 (C-7a). MS FAB, m/z (rel. %): 567 (100)[M+H]. HR MS (FAB): calcd for C$_{25}$H$_{27}$N$_8$O$_8$ [M+H] 567.1952. found 567.1958.

Example 18

4-(Pyridin-2-yl)-7-(β-D-ribofuranosyl)-7H-pyrrolo[2,3-d]pyrimidine (3s)

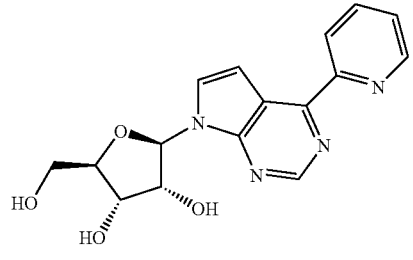

An argon purged mixture of 6-chloro-7-deazapurine riboside 4 (220 mg, 0.77 mM), 2-(tributylstannyl)pyridine (320 μL, 1.16 mM) and PdCl$_2$(PPh$_3$)$_2$ (27 mg, 0.038 mM) in DMF (3 mL) is stirred at 100° C. for 24 h. Volatiles are removed in vacuo and the residue is several times co-evaporated with MeOH and toluene. A suspension of the residue in MeOH/CH$_2$Cl$_2$ is co-evaporated with silica and spray-dried KF and subsequent chromatography on the column of silica (7% MeOH in CHCl$_3$) afforded product 3s (128 mg, 51%) as yellowish oil. Compound is crystallized from MeOH/AcOEt as white powder. $^1$H NMR (600 MHz, DMSO-d$_6$): 3.57 (ddd, 1H, J$_{gem}$=11.9, J$_{5'b,OH}$=5.5, J$_{5'b,4'}$=4.0, H-5'b); 3.66 (ddd, 1H, J$_{gem}$=11.9, J$_{5'a,OH}$=5.3, J$_{5'a,4'}$=4.1, H-5'a); 3.95 (ddd, 1H, J$_{4',5'}$=4.1, 4.0, J$_{4',3'}$=3.3, H-4'); 4.14 (td, 1H, J$_{3',2'}$=J$_{3',OH}$=4.7, J$_{3',4'}$=3.3, H-3'); 4.46 (ddd, 1H, J$_{2',1'}$=6.2, J$_{2',OH}$=6.1, J$_{2',3'}$=4.7, H-2'); 5.10 (dd, 1H, J$_{OH,5'}$=5.5, 5.3, OH-5'); 5.22 (d, 1H, J$_{OH,3'}$=4.7, OH-3'); 5.41 (d, 1H, J$_{OH,2'}$=6.1, OH-2'); 6.30 (d, 1H, J$_{1',2'}$=6.2, H-1'); 7.47 (d, 1H, J$_{5,6}$=3.7, H-5); 7.56 (ddd, 1H, J$_{5,4}$=7.5, J$_{5,6}$=4.7, J$_{5,3}$=1.2, H-5-py); 7.96 (d, 1H, J$_{6,5}$=3.7, H-6); 8.03 (ddd, 1H, J$_{4,3}$=7.9, J$_{4,5}$=7.5, J$_{4,6}$=1.8, H-4-py); 8.57 (ddd, 1H, J$_{3,4}$=7.9, J$_{3,5}$=1.2, J$_{3,6}$=0.9, H-3-py); 8.85 (ddd, 1H, J$_{6,5}$=4.7, J$_{6,4}$=1.8, J$_{6,3}$=0.9, H-6-py); 8.93 (s, 1H, H-2). $^{13}$C NMR (151 MHz, DMSO-d$_6$): 61.81 (CH$_2$-5); 70.82 (CH-3'); 74.28 (CH-2'); 85.39 (CH-4'); 86.83 (CH-1'); 103.63 (CH-5); 115.94 (C-4a); 122.66 (CH-3-py); 125.28 (CH-5-py); 128.57 (CH-6); 137.50 (CH-4-py); 149.89 (CH-6-py); 150.86 (CH-2); 153.07 (C-7a); 153.69 (C-4); 155.97 (C-2-py). IR (KBr): ν=1632, 1577, 1569, 1559, 1453, 1214, 1107, 1100 cm$^{-1}$. MS FAB, m/z (rel. %): 329 (100)[M+H]. HR MS (FAB): calcd for C$_{16}$H$_{17}$N$_4$O$_4$ [M+H] 329.1250. found 329.1243.

Example 19

5-Fluoro-4-phenyl-7-(β-D-ribofuranosyl)-7H-pyrrolo[2,3-d]pyrimidine (8a)

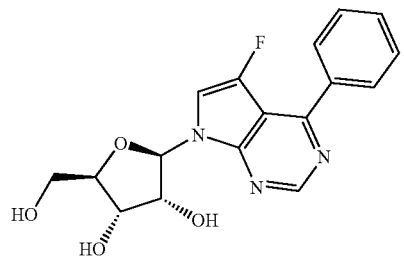

Compound 7a (296 mg, 0.45 mM) is treated with 1M NaOMe/MeOH (135 μL, 0.135 mM) in MeOH (5 mL) for 12 h at RT. The mixture is co-evaporated with silica and chromatographed on the column of silica (3% MeOH in CHCl$_3$)

affording product 8a as crystalline solid (122 mg, 79%). Compound is crystallized from MeOH/CHCl$_3$/hexane as honey-like leaves. $^1$H NMR (600 MHz, DMSO-d$_6$): 3.57 (ddd, 1H, J$_{gem}$=12.0, J$_{5'b,OH}$=5.5, J$_{5'b,4'}$=3.9, H-5b); 3.65 (ddd, 1H, J$_{gem}$=12.0, J$_{5'a,OH}$=5.5, J$_{5'a,4'}$=4.1, H-5'a); 3.94 (ddd, 1H, J$_{4',5'}$=4.1, 3.9, J$_{4',3'}$=3.2, H-4'); 4.12 (ddd, 1H, J$_{3',2'}$=5.1, J$_{3,OH}$=4.9, J$_{3',4'}$=3.2, H-3'); 4.39 (ddd, 1H, J$_{2',OH}$=6.3, J$_{2',1}$=6.1, J$_{2',3}$=5.1, H-2'); 5.10 (t, 1H, J$_{OH,5'}$=5.5, OH-5'); 5.23 (d, 1H, J$_{OH,3'}$=4.9, OH-3'); 5.44 (d, 1H, J$_{OH,2'}$=6.3, OH-2'); 6.35 (dd, 1H, J$_{1',2'}$=6.1, J$_{H,F}$=1.8, H-1'); 7.55-7.61 (m, 3H, H-m,p-Ph); 7.97 (m, 2H, H-o-Ph); 7.99 (d, 1H, J$_{H,F}$=1.9, H-6); 8.93 (s, 1H, H-2). $^{13}$C NMR (151 MHz, DMSO-d$_6$): 61.66 (CH$_2$-5'); 70.71 (CH-3'); 74.34 (CH-2'); 85.51 (CH-4'); 86.41 (CH-1'); 106.16 (d, J$_{C,F}$=15, C-4a); 110.57 (d, J$_{C,F}$=30, CH-6); 128.78 (CH-m-Ph); 129.42 (d, J$_{C,F}$=4, CH-o-Ph); 130.67 (CH-p-Ph); 136.98 (C-i-Ph); 141.58 (d, J$_{C,F}$=247, C-5); 147.60 (d, J$_{C,F}$=3, C-7a); 152.04 (CH-2); 157.00 (d, J$_{C,F}$=4, C-4). $^{19}$F NMR (470.3 MHz, DMSO-d$_6$, ref (C$_6$F$_6$)=−163 ppm): −161.30. IR (KBr): ν=1632, 1597, 1581, 1567, 1471, 1379, 1224, 1085, 1047 cm$^{-1}$. MS FAB, m/z (rel. %): 346 (100) [M+H], 368 (50) [M+Na]. HR MS (FAB): calcd for C$_{17}$H$_{17}$FN$_3$O$_4$ [M+H] 346.1203. found 346.1207.

The intermediate compound 7a is prepared as follows.

a. 5-Fluoro-4-phenyl-7-(2,3,5-tri-O-benzoyl-β-D-ribofuranosyl)-7H-pyrrolo[2,3-d]pyrimidine (7a). An argon purged mixture of protected 6-chloro-7-fluorodeazapurine riboside 6 (329 mg, 0.53 mM), phenylboronic acid (98 mg, 0.80 mM), K$_2$CO$_3$ (150 mg, 1.09 mM) and Pd(PPh$_3$)$_4$ (31 mg, 0.027 mM) in toluene (4 mL) is stirred at 100° C. for 4 h. The mixture is diluted with chloroform (20 mL) and washed with aqueous NH$_4$Cl (sat., 20 mL), aqueous phase is re-extracted with chloroform (2×5 mL). Collected organic extracts are dried over MgSO$_4$, volatiles are removed in vacuo and the residue is chromatographed on silica (hexanes-AcOEt, 6:1) affording product 7a as colorless foam (325 mg, 93%). $^1$H NMR (500 MHz, CDCl$_3$): 4.70 (dd, 1H, J$_{gem}$=12.2, J$_{5'b,4'}$=3.8, H-5'b); 4.80 (ddd, 1H, J$_{4',3'}$=4.3, J$_{4',5'}$=3.8, 3.2, H-4'); 4.88 (dd, 1H, J$_{gem}$=12.2, J$_{5'a,4'}$=3.2, H-5'a); 6.11 (dd, 1H, J$_{3',2'}$=5.9, J$_{3',4'}$=4.3, H-3'); 6.18 (t, 1H, J$_{2',1'}$=J$_{2',3'}$=5.9, H-2'); 6.86 (dd, 1H, J$_{1',2'}$=5.9, J$_{H,F}$=1.3, H-1'); 7.20 (d, 1H, J$_{H,F}$=2.4, H-6); 7.36 and 7.42 (2×m, 2×2H, H-m-Bz); 7.47-7.56 (m, 6H, H-m,p-Bz and H-m,p-Ph); 7.59 and 7.60 (2×m, 2×1H, H-p-Bz); 7.95 (m, 2H, H-o-Bz); 7.97 (m, 2H, H-o-Ph); 8.02 and 8.14 (2×m, 2×2H, CH-o-Bz); 8.93 (s, 1H, H-2). $^{13}$C NMR (125.7 MHz, CDCl$_3$): 63.75 (CH$_2$-5'); 71.46 (CH-3'); 73.76 (CH-2'); 80.30 (CH-4'); 85.69 (CH-1'); 106.53 (d, J$_{C,F}$=15, C-4-a); 108.46 (d, J$_{C,F}$=30, CH-6); 128.43 (C-i-Bz); 128.48, 128.50 and 128.54 (CH-m-Bz and CH-m-Ph); 128.72 and 129.33 (C-i-Bz); 129.42 (d, J$_{C,F}$=4, CH-o-Ph); 129.68, 129.82 and 129.84 (CH-o-Bz); 130.47 (CH-p-Ph); 133.52 and 133.73 (CH-p-Bz); 136.69 (C-i-Ph); 143.00 (d, J$_{C,F}$=253, C-5); 148.13 (d, J$_{C,F}$=3, C-7a); 152.39 (CH-2); 158.46 (d, J$_{C,F}$=4, C-4); 165.12, 165.41 and 166.13 (CO). $^{19}$F NMR (470.3 MHz, CDCl$_3$): −158.37. MS FAB, m/z (rel. %): 658 (100)[M+H]. HR MS (FAB): calcd for C$_{38}$H$_{29}$FN$_3$O$_7$ [M+H] 658.1990. found 658.1991.

Example 20

5-Fluoro-4-(furan-2-yl)-7-(β-D-ribofuranosyl)-7H-pyrrolo[2,3-d]pyrimidine (8b)

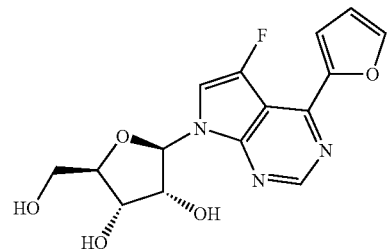

Compound 7b (395 mg, 0.61 mM) is treated with 1M NaOMe/MeOH (183 μL, 0.18 mM) in MeOH (5 mL) for 12 h at RT. The mixture is co-evaporated with silica and chromatographed on the column of silica (3% MeOH in CHCl$_3$) affording product 8b (160 mg, 78%) as white solid. Crystallization from MeOH provided beige powder. $^1$H NMR (600 MHz, DMSO-d$_6$): 3.56 (ddd, 1H, J$_{gem}$=11.9, J$_{5'b,OH}$=5.5, J$_{5'b,4'}$=3.9, H-5'b); 3.64 (ddd, 1H, J$_{gem}$=11.9, J$_{5'a,OH}$=5.5, J$_{5'a,4'}$=4.1, H-5'a); 3.92 (ddd, 1H, J$_{4',5'}$=4.1, 3.9, J$_{4',3'}$=3.3, H-4'); 4.11 (ddd, 1H, J$_{3',2'}$=5.1, J$_{3,OH}$=4.9, J$_{3',4'}$=3.3, H-3'); 4.36 (ddd, 1H, J$_{2,OH}$=6.3, J$_{2',1}$=6.1, J$_{2',3}$=5.1, H-2'); 5.10 (t, 1H, J$_{OH,5'}$=5.5, OH-5'); 5.22 (d, 1H, J$_{OH,3}$=4.9, OH-3'); 5.43 (d, 1H, J$_{OH,2'}$=6.3, OH-2'); 6.31 (dd, 1H, J$_{1',2'}$=6.1, J$_{H,F}$=1.8, H-1'); 6.80 (dd, 1H, J$_{4,3}$=3.5, J$_{4,5}$=1.7, H-4-furyl); 7.48 (dd, 1H, J$_{3,4}$=3.5, J$_{3,5}$=0.8, H-3-furyl); 7.96 (d, 1H, J$_{H,F}$=1.9, H-6); 8.08 (dd, 1H, J$_{5,4}$=1.7, J$_{5,3}$=0.8, H-5-furyl); 8.81 (s, 1H, H-2). $^{13}$C NMR (151 MHz, DMSO-d$_6$): 61.64 (CH$_2$-5'); 70.68 (CH-3'); 74.34 (CH-2'); 85.47 (CH-4'); 86.36 (CH-1'); 102.12 (d, J$_{C,F}$=16, C-4a); 110.75 (d, J$_{C,F}$=30, CH-6); 113.15 (CH-3-furyl); 114.93 (d, J$_{C,F}$=6, CH-4-furyl); 141.46 (d, J$_{C,F}$=249, C-5); 146.04 (4, J$_{C,F}$=4, C-4); 147.02 (CH-5-furyl); 147.80 (d, J$_{C,F}$=3, C-7a); 151.12 (C-2-furyl); 151.81 (CH-2). $^{19}$F NMR (470.3 MHz, DMSO-d$_6$, ref (C$_6$F$_6$)=−163 ppm): −161.79. IR (KBr): ν=1586, 1485, 1461, 1395, 1249, 1209, 1101, 1046, 1021 cm$^{-1}$ MS FAB, m/z (rel. %): 204 (90), 336 (100)[M+H]. HR MS (FAB): calcd for C$_{15}$H$_{15}$FN$_3$O$_5$ [M+H] 336.0996. found 336.1003.

The intermediate compound 7b is prepared as follows.

a. 5-Fluoro-4-(furan-2-yl)-7-(2,3,5-tri-O-benzoyl-β-D-ribofuranosyl)-7H-pyrrolo[2,3-d]pyrimidine (7b). An argon purged mixture of 6-chloro-7-fluorodeazapurine riboside 6 (377 mg, 0.61 mM), 2-(tributylstannyl)furane (270 μL, 0.85 mM) and PdCl$_2$(PPh$_3$)$_2$ (21 mg, 0.03 mM) in DMF (3 mL) is stirred at 100° C. for 12 h. Volatiles are removed in vacuo and the residue is several times co-evaporated with toluene. Column chromatography on silica (hexanes-AcOEt, 20:1→10:1) affords product 7b as yellowish foam (395 mg, 100%). $^1$H NMR (600 MHz, CDCl$_3$): 4.69 (dd, 1H, J$_{gem}$=12.2, J$_{5'b,4'}$=3.7, H-5'b); 4.80 (ddd, 1H, J$_{4',3'}$=4.1, J$_{4',5'}$=3.7, 3.1, H-4'); 4.88 (dd, 1H, J$_{gem}$12.2, J$_{5'a,4'}$=3.1, H-5'a); 6.09 (dd, 1H, J$_{3',2'}$=5.9, J$_{3',4'}$=4.1, H-3'); 6.14 (t, 1H, J$_{2',3'}$=J$_{2',1}$=5.9, H-2'); 6.63 (dd, 1H, J$_{4,3}$=3.5, J$_{4,5}$=1.7, H-4-furyl); 6.84 (dd, 1H, J$_{1',2'}$=5.9, J$_{H,F}$=1.3, H-1'); 7.199 (d, 1H, J$_{H,F}$=2.4H-6); 7.36 and 7.42 (2×m, 2×2H, H—-Bz); 7.50 (dd, 1H, J$_{3,4}$=3.5, J$_{3,5}$=0.7, H-3-furyl); 7.51 (m, 2H, H-m-Bz); 7.54, 7.60 and 7.62 (3×m, 3×1H, H-p-Bz); 7.71 (dd, 1H, $J_{5,4}$=1.7, $J_{5,3}$=0.7, H-5-furyl); 7.93, 8.02 and 8.15 (3×m, 3×2H, H-o-Bz); 8.85 (s, 1H, H-2). $^{13}$C NMR (151 MHz, CDCl$_3$): 63.73 (CH$_2$-5'); 71.40 (CH-3'); 73.69 (CH-2'); 80.26 (CH-4'); 85.41 (CH-1'); 103.47 (d, $J_{C,F}$=16, CH-4a); 108.46 (d, $J_{C,F}$=31, CH-6); 112.66 (CH-4-furyl); 115.68 (d, $J_{C,F}$=11, CH-3-furyl); 128.30 (C-i-Bz); 128.48 and 128.54 (CH-m-Bz); 128.60 (C-i-Bz); 128.72 (CH-m-Bz); 129.23 (C-i-Bz); 129.66, 129.81 and 129.82 (CH-o-Bz); 133.56 and 133.76 (CH-p-Bz); 142.79 (d, $J_{C,F}$=253, C-5); 145.84 (CH-5-furyl); 147.07 (d, $J_{C,F}$=4, C-4); 148.16 (d, $J_{C,F}$=3, C-7a); 150.45 (C-2-furyl); 152.25 (CH-2); 165.11, 165.42 and 166.15 (CO). $^{19}$F NMR (470.3 MHz, CDCl$_3$): −159.30. MS FAB, m/z (rel. %): 648 (100)[M+H]. HR MS (FAB): calcd for C$_{36}$H$_{27}$FN$_3$O$_8$ [M+H] 648.1782. found 648.1775.

Example 21

5-Fluoro-7-β-D-ribofuranosyl)-4-(thiophen-2-yl)-7H-pyrrolo[2,3-d]pyrimidine (8c)

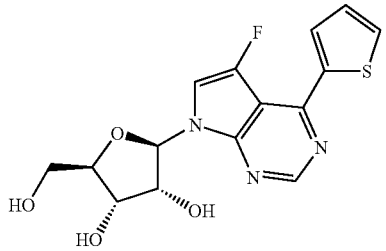

Compound 7c (145 mg, 0.22 mM) is treated with 1M NaOMe/MeOH (40 μL, 0.04 mM) in MeOH (4 mL) for 12 h at RT. The mixture is co-evaporated with silica and chromatographed on the column of silica (2.5% MeOH in CHCl$_3$) affording product 8c (57 mg, 74%) as lemon-like solid. Crystallization from MeOH/AcOEt/hexane provided yellowish powder. $^1$H NMR (600 MHz, DMSO-d$_6$): 3.56 (ddd, 1H, $J_{gem}$=11.9, $J_{5'b,OH}$=5.4, $J_{5'b,4'}$=4.0, H-5'b); 3.65 (ddd, 1H, $J_{gem}$=11.9, $J_{5'a,OH}$=5.4, $J_{5'a,4'}$=4.1, H-5'a); 3.93 (ddd, 1H, $J_{4',5'}$=4.1, 4.0, $J_{4',3'}$=3.1, H-4'); 4.11 (ddd, 1H, $J_{3,OH}$=4.9, $J_{3',2'}$=4.8, $J_{3',4'}$=3.1, H-3'); 4.36 (ddd, 1H, $J_{2',OH}$=6.3, $J_{2',1'}$=6.0, $J_{2',3'}$=4.8, H-2'); 5.10 (t, 1H, $J_{OH,5}$=5.4, OH-5'); 5.22 (d, 1H, $J_{OH,3}$=4.9, OH-3'); 5.44 (d, 1H, $J_{OH,2}$=6.3, OH-2'); 6.32 (dd, 1H, $J_{1',2'}$=6.0, $J_{H,F}$=1.9, H-1'); 7.31 (dd, 1H, $J_{4,5}$=5.0, $J_{4',3}$=3.8, H-4-thienyl); 7.90 (dd, 1H, $J_{5,4}$=5.0, $J_{5,3}$=1.1, H-5-thienyl); 8.01 (d, 1H, $J_{H,F}$=1.8, H-6); 8.07 (dd, 1H, $J_{3,4}$=3.8, $J_{3,5}$=1.1, H-3-thienyl); 8.78 (s, 1H, H-2). $^{13}$C NMR (151 MHz, DMSO-d$_6$): 61.61 (CH$_2$-5'); 70.64 (CH-3'); 74.37 (CH-2'); 85.48 (CH-4'); 86.46 (CH-1'); 102.44 (d, $J_{C,F}$=15, CH-4a); 110.70 (d, $J_{C,F}$=31, CH-6); 129.39 (d, $J_{C,F}$=2, CH-4-thienyl); 130.31 (d, $J_{C,F}$=16, CH-3-thienyl); 131.99 (CH-5-thienyl); 141.53 (d, $J_{C,F}$=246, C-5); 141.98 (C-2-thienyl); 147.73 (d, $J_{C,F}$=3, C-7a); 150.25 (d, $J_{C,F}$=4, C-4); 151.71 (CH-2). $^{19}$F NMR (470.3 MHz, DMSO-d$_6$, ref (C$_6$F$_6$)=−163 ppm): −160.86. IR (Kr): ν=1633, 1590, 1565, 1458, 1428, 1102, 1056 cm$^1$. MS FAB, m/z (rel. %): 220 (100), 352 (20)[M+H]. HR MS (FAB): calcd for C$_{15}$H$_{15}$FN$_3$O$_4$S [M+H] 352.0767. found 352.0754.

The intermediate compound 7c is prepared as follows.

a. 5-Fluoro-4-(thiophen-2-yl)-7-(2,3,5-tri-O-benzoyl-β-D-ribofuranosyl)-7H-pyrrolo[2,3-d]pyrimidine (7c). An argon purged mixture of 6-chloro-7-fluorodeazapurine riboside 6 (205 mg, 0.33 mM), 2-(tributylstannyl)thiophene (116 μL, 0.365 mM) and PdCl$_2$(PPh$_3$)$_2$ (12 mg, 0.017 mM) in DMF (3 mL) is stirred at 100° C. for 3 h. Volatiles are removed in vacuo and the residue is several times co-evaporated with toluene. Column chromatography on silica (hexanes-AcOEt, 20:1→10:1) affords product 7c as yellowish foam (164 mg, 74%). $^1$H NMR (600 MHz, CDCl$_3$): 4.69 (dd, 1H, $J_{gem}$=12.2, $J_{5'b,4'}$=3.7, H-5'b); 4.80 (ddd, 1H, $J_{4',3'}$=4.1, $J_{4',5'}$=3.7, 3.0, H-4'); 4.88 (dd, 1H, $J_{gem}$=12.2, $J_{5'a,4'}$=3.0, H-5'a); 6.09 (dd, 1H, $J_{3',2'}$=5.9, $J_{3',4'}$=4.1, H-3); 6.14 (dd, 1H, $J_{2',1'}$=6.1, $J_{2',3'}$=5.9, H-2'); 6.86 (dd, 1H, $J_{1',2'}$=6.1, $J_{H,F}$=1.4, H-1'); 7.199 (d, 1H, $J_{H,F}$=2.2, H-6); 7.202 (dd, 1H, $J_{4,5}$=5.0, $J_{4,3}$=3.8, H-4-thienyl); 7.36, 7.42 and 7.51 (3×m, 3×2W, H-m-Bz); 7.54 (m, 1H, H-p-Bz); 7.58 (dd, 1H, $J_{5,4}$=5.0, $J_{5,3}$=1.1, H-5-thienyl); 7.59 and 7.63 (2×m, 2×1H, H-p-Bz); 7.94 and 8.02 (2×m, 2×2H, H-o-Bz); 8.10 (dd, 1H, $J_{3,4}$=3.9, $J_{3,5}$=1.1, H-3-thienyl); 8.15 (m, 2H, H-o-Bz); 8.79 (s, 1H, H-2). $^{13}$C NMR (151 MHz, CDCl$_3$): 63.77 (CH$_2$-5'); 71.43 (CH-3'); 73.67 (CH-2'); 80.30 (CH-4'); 85.32 (CH-1'); 103.85 (d, $J_{C,F}$=15, C-4-a); 108.23 (d, $J_{C,F}$=32, CH-6); 128.30 (C-i-Bz); 128.40 and 128.54 (CH-m-Bz); 128.60 (C-i-Bz); 128.72 (CH-m-Bz); 128.82 (d, $J_{C,F}$=2, CH-4-thienyl); 129.23 (C-i-Bz); 129.66, 129.81 and 129.82 (CH-o-Bz); 130.63 (d, $J_{C,F}$=17, CH-3-thienyl); 130.84 (CH-5-thienyl); 133.57 and 133.75 (CH-p-Bz); 141.92 (C-2-thienyl); 142.93 (d, $J_{C,F}$=251, C-5); 148.96 (d, $J_{C,F}$=3, C-7a); 152.94 (d, $J_{C,F}$=4, C-4); 152.08 (CU-2); 165.10, 165.41 and 166.13 (CO). $^{19}$F NMR (470.3 MHz, CDCl$_3$): −158.00. MS FAB, m/z (rel. %): 664 (100)[M+H]. HR MS (FAB): calcd for C$_{36}$H$_{27}$FN$_3$O$_7$S [M+H] 664.1554. found 664.1542.

Example 22

5-Fluoro-4-pyrrol-2-yl)-7-(β-D-ribofuranosyl)-7H-pyrrolo[2,3-d]pyrimidine (8d)

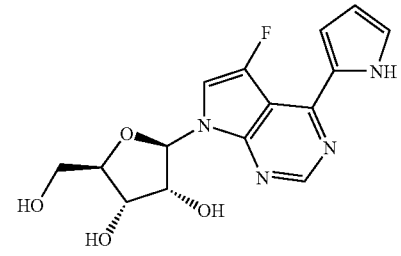

Compound 7d (166 mg, 0.257 mM) is treated with 1M NaOMe/MeOH (77 μL, 0.077 mM) in MeOH (4 mL) for 12 h at RT. The mixture is co-evaporated with silica and chromatographed on the column of silica (4% MeOH in CHCl$_3$) affording product 8d (76 mg, 89%) as beige solid. Compound is crystallized from MeOH. $^1$H NMR (500 MHz, DMSO-d$_6$): 3.56 (ddd, 1H, $J_{gem}$=12.0, $J_{5'b,OH}$=5.5, $J_{5'b,4'}$=4.0, H-5'b); 3.64 (ddd, 1H, $J_{gem}$=12.0, $J_{5'a,OH}$=5.4, $J_{5'a,4'}$=4.0, H-5'a); 3.91 (td, 1H, $J_{4',5'}$=4.0, $J_{4',3'}$=3.3, H-4'); 4.11 (ddd, 1H, $J_{3',2'}$=5.1, $J_{3,OH}$=4.9, $J_{3',4'}$=3.3, H-3'); 4.35 (ddd, 1H, $J_{2',OH}$=6.2, $J_{2',1'}$=6.1, $J_{2',3}$=5.1, H-2'); 5.08 (dd, 1H, $J_{OH,5}$=5.5, 5.4, OH-5'); 5.17 (d, 1H, $J_{OH,3}$=4.9, OH-3'); 5.38 (d, 1H, $J_{OH,2'}$=6.2, OH-2'); 6.27 (dd, 1H, $J_{1',2'}$=6.1, $J_{H,F}$=19, H-1'); 6.30 (ddd, 1H, $J_{4,3}$=3.7, $J_{4,5}$=2.5, $J_{4,NH}$=2.3, H-4-pyrr); 7.08 (ddd, 1H, $J_{5,NH}$=2.9, $J_{5,4}$=2.5, $J_{5,3}$=1.3, H-5-pyrr); 7.17 (ddt, 1H, $J_{3,4}$=3.7, $J_{3,NH}$=2.5, $J_{3,5}$=$J_{H,F}$=1.3, H-3-pyrr); 7.83 (d, 1H, $J_{H,F}$=1.9, H-6); 8.70 (s, 1H, H-2); 11.85 (bs, 1H, NH). $^{13}$C NMR (125.7 MHz, DMSO-d$_6$): 61.67 (CH$_2$-5'); 70.65 (CH-3'); 74.23 (CH-2'); 85.35 (CH-4'); 86.38 (CH-1'); 101.32 (d, $J_{C,F}$=15, C-4a); 109.18 (d, $J_{C,F}$=31, CH-6); 110.86 (d, $J_{C,F}$=2, CH-4-pyrr); 114.06 (d, $J_{C,F}$=18, CH-3-pyrr); 123.82 (CH-5-pyrr); 128.30 (C-2-pyrr); 141.81 (d, $J_{C,F}$=246, C-5); 147.42 (d, $J_{C,F}$=3, C-7a); 148.56 (d, $J_{C,F}$=4, C-4); 151.65 (CH-2). $^{19}$F NMR (470.3 MHz, DMSO-d$_6$, ref (C$_6$F$_6$)=−163 ppm): −161.47. MS FAB, m/z (rel. %): 335 (100)[M+H]. HRMS (FAB): calcd for C$_{15}$H$_{16}$FN$_4$O$_4$ [M+H] 335.1156. found 335.1161. Anal. Calcd for C$_{15}$H$_{15}$FN$_4$O$_4$.½H$_2$O: C, 52.48; H, 4.70; N, 16.32. Found: C, 52.66; H, 4.53; N, 16.05.

The intermediate compound 7d is prepared as follows.

a. 5-Fluoro-4-(pyrrol-2-yl)-7-(2,3,5-tri-O-benzoyl-β-D-ribofuranosyl)-7H-pyrrolo[2,3-d]pyrimidine (7d). Pyrrole (242 µL, 3.5 mM) is dropwise added to a suspension of NaH (55% in mineral oil, 153 mg, 3.5 mM) in THF (4 mL) and the mixture is stirred for 30 min at RT, followed by the addition of ZnCl$_2$ solution (1M sol. in THF, 3.8 mL, 3.8 mM). Resulting thick slurry is stirred for additional 2 h and then is transferred via cannula to an argon purged flask with 6-chloro-7-fluorodeazapurine riboside 6 (431 mg, 0.7 mM), Pd(PPh$_3$)$_4$ (40 mg, 0.035 mM) and the reaction mixture is stirred at 90° C. for 12 h. The mixture is diluted with chloroform (20 mL) and washed with aqueous EDTA (sat., 20 mL). Aqueous layer is re-extracted with chloroform (2×5 mL). Collected organic extracts are dried over MgSO$_4$, evaporated and chromatographed on silica (hexanes-AcOEt, 5:1) affording product 7d (188 mg, 42%) as yellowish foam. $^1$H NMR (500 MHz, CDCl$_3$): 4.68 (dd, 1H, J$_{gem}$=12.2, J$_{5'b,4'}$=3.8, H-5'b); 4.78 (ddd, 1H, J$_{4',3'}$=4.3, J$_{4,5}$=3.8, 3.2, H-4'); 4.86 (dd, $^1$H, J$_{gem}$=12.2, J$_{5'a,4'}$=3.2, H-5a); 6.09 (dd, 1H, J$_{3',2'}$=5.8, J$_{3',4'}$=4.3, H-3'); 6.15 (t, 1H, J$_{2',1'}$=J$_{2',3'}$=5.8, H-2'); 6.39 (dt, 1H, J$_{4,3}$=3.8, J$_{4,5}$=J$_{4,NH}$=2.6, H-4-pyrrole); 6.80 (dd, 1H, J$_{1',2'}$=5.8, J$_{H,F}$=1.5, H-1'); 7.04 (td, 1H, J$_{5,4}$=J$_{5,NH}$=2.6, J$_{5,3}$=1.3, H-5-pyrrole); 7.11 (d, 1H, J$_{H,F}$=2.4, H-6); 7.45 (ddd, 1H, J$_{3,4}$=3.8, J$_{3,NH}$=2.4, J$_{3,5}$=1.3, H-3-pyrrole); 7.35, 7.40 and 7.49 (3×m, 3×2H, H-m-Bz); 7.53, 7.59 and 7.60 (3×m, 3×1H, H-p-Bz); 7.94, 8.00 and 8.14 (3×m, 3×2H, H-o-Bz); 8.66 (s, 1H, H-2); 9.97 (bs, 1H NH). $^{13}$C NMR (125.7 MHz, CDCl$_3$): 63.79 (CH$_2$-5'); 71.47 (CH-3'); 73.74 (CH-2'); 80.19 (CH-4'); 85.51 (CH-1'); 102.76 (d, J$_{C,F}$=16, C-4a); 107.26 (d, J$_{C,F}$=31, CH-6); 1111.65 (J$_{C,F}$=3, CH-4-pyrrole); 114.64 (J$_{C,F}$=17, CH-3-pyrrole); 123.38 (CH-5-pyrrole); 128.50 (CH—Bz); 128.50 (C-2-pyrrole); 128.52 (CH-m-Bz); 128.65 (C-i-Bz); 128.69 (CH-m-Bz); 128.75 and 129.37 (C-i-Tol); 129.70, 129.83 and 129.85 (CH-o-Bz); 133.49 and 133.68 (CH-p-Tol); 143.24 (d, J$_{C,F}$=251, C-5); 148.05 (d, J$_{C,F}$=4, C-7a); 148.82 (d, J$_{C,F}$=4, C-4); 152.05 (CH-2); 165.11, 165.41 and 166.15 (CO). $^{19}$F NMR (470.3 MHz, CDCl$_3$, ref(C$_6$F$_6$)=−163 ppm): −158.88. MS FAB, m/z (rel. %): 203 (100), 279 (100), 647 (75)[M+H]. HR MS (FAB): calcd for C$_{36}$H$_{28}$FN$_4$O$_7$ [M+H] 647.1942. found 647.1915.

Example 23

5-Fluoro-4-(furan-3-yl)-7-(β-D-ribofuranosyl)-7H-pyrrolo[2,3-d]pyrimidine (8e)

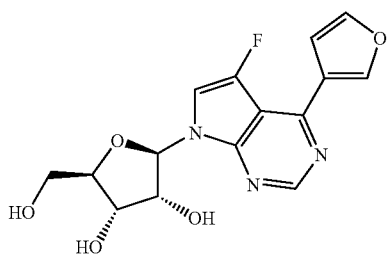

Compound 7e (132 mg, 0.20 mM) is treated with 1M NaOMe/MeOH (40 µL, 0.04 mM) in MeOH (4 mL) for 12 h at RT. The mixture is co-evaporated with silica and chromatographed on the column of silica (3% MeOH in CHCl$_3$) affording product 8e (53 mg, 78%) as colorless solid. Crystallization from MeOH/AcOEt/hexane provides white powder. $^1$H NMR (600 MHz, DMSO-d$_6$): 3.56 (ddd, 1H, J$_{gem}$=11.9, J$_{5'b,OH}$=5.5 J$_{5'b,4'}$=4.0, H-5'b); 3.64 (ddd, H, J$_{gem}$=11.9, J$_{5'a,OH}$=5.5, J$_{5'a,4'}$=4.2, H-5'a); 3.92 (ddd, in, J$_{4',5'}$=4.2, 4.0, J$_{4',3'}$=3.1, H-4'); 4.11 (ddd, 1H, J$_{3',2'}$=5.1, J$_{3,OH}$=4.9, J$_{3',4'}$=3.1, H-3'); 4.36 (ddd, 1H, J$_{2',OH}$=6.3, J$_{2',1'}$=6.1, J$_{2',3'}$=5.1, H-2'); 5.09 (t, 1H, J$_{OH,5'}$=5.5, OH-5'); 5.22 (d, 1H, J$_{OH,3'}$=4.9, OH-3'); 5.43 (d, 1H, J$_{OH,2'}$=6.3, OH-2'); 6.31 (dd, 1H, J$_{1',2'}$=6.1, J$_{H,F}$=1.9, H-1'); 7.17 (dd, 1H, J$_{4,5}$=1.8, J$_{4,2}$=0.7, H-4-furyl); 7.90 (dd, 1H, J$_{5,4}$=1.8, J$_{5,2}$=1.6, H-5-furyl); 7.96 (d, 1H, J$_{H,F}$=1.8, H-6); 8.48 (dt, 1H, J$_{2,5}$=1.6, J$_{2,4}$=J$_{H,F}$=0.7, H-2-furyl); 8.82 (s, 1H, H-2). $^{13}$C NMR (151 MHz, DMSO-d$_6$): 61.64 (CH$_2$-5'); 70.67 (CH-3'); 74.32 (CH-2'); 85.46 (CH-4'); 86.39 (CH-1'); 104.03 (d, J$_{C,F}$=15, C-4a); 109.97 (d, J$_{C,F}$=6, CH-4-furyl); 110.27 (d, J$_{C,F}$=30, CH-6); 124.52 (C-3-furyl); 141.53 (d, J$_{C,F}$=246, C-5); 144.91 (CH-5-furyl); 145.49 (d, J$_{C,F}$=13, CH-2-furyl); 147.43 (d, J$_{C,F}$=3, C-7a); 149.68 (d, J$_{C,F}$=4, C-4); 152.02 (CH-2). $^{19}$F NMR (470.3 MHz, DMSO-d$_6$, ref(C$_6$F$_6$)=−163 ppm): −163.20. IR (KBr): ν=1630, 1589, 1463, 1250, 1220, 1161, 1083, 1052 cm$^{-1}$. MS FAB, m/z (rel. %): 204 (100), 336 (25)[M+H]. HR MS (FAB): calcd for C$_{15}$H$_{15}$FN$_3$O$_5$ [M+H] 336.0996. found 336.0991.

The intermediate compound 7e is prepared as follows.

a. 5-Fluoro-4-(furan-3-yl)-7-(2,3,5-tri-O-benzoyl-β-D-ribofuranosyl)-7H-pyrrolo[2,3-d]pyrimidine (7e). An argon purged mixture of protected 6-chloro-7-fluorodeazapurine riboside 6 (216 mg, 0.35 mM), furane-3-boronic acid (49 mg, 0.44 mM), K$_2$CO$_3$ (72 mg, 0.52 mM) and Pd(PPh$_3$)$_4$ (20 mg, 0.017 mM) in toluene (2 mL) is stirred at 100° C. for 10 h. The mixture is diluted with chloroform (20 ml) and washed with aqueous NH$_4$Cl (sat., 20 mL), aqueous phase is re-extracted with chloroform (2×5 mL). Collected organic extracts are dried over MgSO$_4$, volatiles are removed in vacuo and the residue is chromatographed on silica (hexanes-AcOEt, 6:1) affording product 7e as colorless foam (151 mg, 66%). $^1$H NMR (600 MHz, CDCl$_3$): 4.68 (dd, 1H, J$_{gem}$=12.2, J$_{5'b,4'}$=3.7, H-5'b); 4.80 (ddd, 1H, J$_{4',3'}$=4.1, J$_{4',5'}$=3.7, 3.0 H-4'); 4.88 (dd, 1H, J$_{gem}$=12.1, J$_{5'a,4'}$=3.0, H-5'a); 6.09 (dd, 1H, J$_{3',2'}$=5.8, J$_{3',4'}$=4.1, H-3'); 6.14 (dd, 1H, J$_{2',1'}$=6.1, J$_{2',3'}$=5.8, H-2'); 6.84 (dd, 1H, J$_{1',2'}$=6.1, J$_{H,F}$=1.3, H-1'); 7.17 (d, 1H, J$_{H,F}$=2.2, H-6); 7.18 (dd, 1H, J$_{4,5}$=1.8, J$_{H,F}$=0.7, H-4-furyl); 7.36, 7.42 and 7.51 (3×m, 3×2H, H-m-Bz); 7.54 (dd, 1H, J$_{5,4}$=1.8, J$_{5,4}$=1.6, H-5-furyl); 7.54, 7.60 and 7.63 (3×m, 3×1H, H-p-Bz); 7.93, 8.02 and 8.15 (3×m, 3×2H, H-o-Bz); 8.32 (dd, 1H, J$_{2,5}$=1.6, J$_{H,F}$=0.7, H-2-furyl); 8.83 (s, 1H, H-2). $^{13}$C NMR (151 MHz, CDCl$_3$): 63.76 (CH$_2$-5'); 71.42 (CH-3'); 73.64 (CH-2'); 80.25 (CH-4'); 85.34 (CH-1'); 105.29 (d, J$_{C,F}$=15, C-4a); 108.01 (d, J$_{C,F}$=31, CH-6); 109.75 (d, J$_{C,F}$=6, CH-4-furyl); 124.39 (C-3-furyl); 128.30 (C-i-Bz); 128.47 and 128.54 (CH-in-Bz); 128.60 (C-i-Bz); 128.72 (CH-m-Bz); 129.23 (C-i-Bz); 129.66, 129.81 and 129.82 (CH-o-Bz); 133.57 and 133.76 (CH-p-Bz); 142.88 (d, J$_{C,F}$=251, C-5); 143.76 (CH-5-furyl); 145.53 (d, J$_{C,F}$=15, CH-2-furyl); 147.95 (d, J$_{C,F}$=3, C-7a); 150.99 (d, J$_{C,F}$=4, C-4); 152.38 (CH-2); 165.11, 165.42 and 166.14 (CO). $^{19}$F NMR (470.3 MHz, CDCl$_3$); −160.62. MS FAB, ml: (rel. %): 648 (100)[M+H]. HR MS (FAB): calcd for C$_{36}$H$_{27}$FN$_3$O$_8$ [M+H] 648.1782. found 648.1807.

Example 24

5-Fluoro-7-(β-D-ribofuranosyl)-4-(thiophen-3-yl)-7H-pyrrolo[2,3-d]pyrimidine (8f)

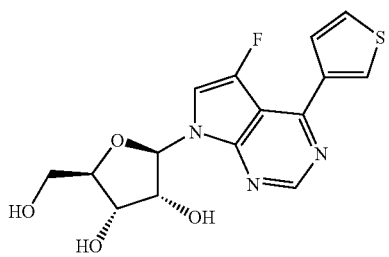

Compound 7f (136 mg, 0.20 mM) is treated with 1M NaOMe/MeOH (40 μL, 0.04 mM) in MeOH (4 mL) for 12 h at RT. The mixture is co-evaporated with silica and chromatographed on the column of silica (3% MeOH in CHCl$_3$) affording product 8f (58 mg, 81%) as colorless solid. Crystallization from MeOH/AcOEt/hexane provided white powder. $^1$H NMR (600 MHz, DMSO-d$_6$): 3.56 (ddd, 1H, $J_{gem}$=11.9, $J_{5'b,OH}$=5.5, $J_{5'b,4'}$=4.0, H-5'b); 3.64 (ddd, 1H, $J_{gem}$=11.9, $J_{5'a,OH}$=5.5, $J_{5'a,4'}$=4.1, H-5'a); 3.93 (ddd, 1H, $J_{4',5'}$=4.1, 4.0, $J_{4',3'}$=3.3, H-4'); 4.11 (ddd, 1H, $J_{3',2'}$=5.1, $J_{3,OH}$=4.9, $J_{3',4'}$=3.3, H-3'); 4.37 (ddd, 1H, $J_{2',OH}$=6.3, $J_{2',1'}$=6.1, $J_{2',3'}$=5.1, H-2'); 5.10 (t, 1H, $J_{OH,5'}$=5.5, OH-5'); 5.22 (d, 1H, $J_{OH,3}$=4.9, OH-3'); 5.43 (d, 1H, $J_{OH,2'}$=6.3, OH-2'); 6.33 (dd, 1H, $J_{1',2'}$=6.1, $J_{H,F}$=1.9, H-1'); 7.74 (dd, 1H, $J_{5,4}$=5.1, $J_{5,2}$=2.9, H-5-thienyl); 7.83 (ddd, 1H, $J_{4,5}$=5.0, $J_{4,2}$=1.4, $J_{H,F}$=0.8, H-4-thienyl); 7.98 (d, 1H, $J_{C,F}$=1.8, H-6); 8.36 (ddd, 1H, $J_{2,5}$=2.9, $J_{2,4}$=1.4, $J_{H,F}$=0.6, H-2-thienyl); 8.85 (s, 1H, H-2). $^{13}$C NMR (151 MHz, DMSO-d$_6$): 61.65 (CH$_2$-5'); 70.68 (CH-3'); 74.33 (CH-2'); 85.47 (CH-4'); 86.38 (CH-1'); 104.16 (d, $J_{C,F}$=15, C-4a); 110.43 (d, $J_{C,F}$=31, CH-6); 127.31 (CH-5-thienyl); 128.03 (d, $J_{C,F}$=6, CH-4-thienyl); 129.56 (d, $J_{C,F}$=1H, CH-2-thienyl); 139.09 (C-3-thienyl); 141.58 (d, $J_{C,F}$=247, C-5); 147.73 (d, $J_{C,F}$=3, C-7a); 151.74 (d, $J_{C,F}$=4, C-4); 151.94 (CH-2). $^{19}$F NMR (470.3 MHz, DMSO-d$_6$, ref (C$_6$F$_6$)=−163 ppm): −161.15. IR (KBr): ν=1631, 1571, 1462, 1110, 1079, 1049 cm$^{-1}$. MS FAB, m/z (rel. %): 220 (100), 352 (60) [M+H]. HR MS (FAB): calcd for C$_{15}$H$_{15}$FN$_3$O$_4$S [M+H] 352.0767. found 352.0770.

The intermediate compound 7f is prepared as follows.

a. 5-Fluoro-4-(thiophen-3-yl)-7-(2,3,5-tri-O-benzoyl-β-D-ribofuranosyl)-7H-pyrrolo[2,3-d]pyrimidine (7f). An argon purged mixture of protected 6-chloro-7-fluorodeazapurine riboside 6 (216 mg, 0.35 mM), thiophene-3-boronic acid (56 mg, 0.44 mM), K$_2$CO$_3$ (72 mg, 0.52 mM) and Pd(PPh$_3$)$_4$ (20 mg, 0.017 mM) in toluene (2 mL) is stirred at 100° C. for 16 h. The mixture is diluted with chloroform (20 mL) and washed with aqueous NH$_4$Cl (sat., 20 mL), aqueous phase is re-extracted with chloroform (2×5 mL). Collected organic extracts are dried over MgSO$_4$, volatiles are removed in vacuo and the residue is chromatographed on silica (hexanes-AcOEt, 6:1) affording product 7f as yellowish foam (155 mg, 67%). $^1$H NMR (500 MHz, CDCl$_3$): 4.69 (dd, 1H, $J_{gem}$=12.1, $J_{5'b,4'}$=3.7, H-5'b); 4.79 (ddd, 1H, $J_{4',3'}$=4.2, $J_{4',5'}$=3.7, 3.1, H-4'); 4.88 (dd, 1H, $J_{gem}$=12.1, $J_{5'a,4'}$=3.1, H-5'a); 6.10 (dd, 1H, $J_{3',2'}$=6.0, $J_{3',4'}$=4.2, H-3); 6.16 (dd, 1H, $J_{2',3'}$=6.0, $J_{2',1'}$=5.9, H-2'); 6.85 (dd, 1H, $J_{1',2'}$=5.9, $J_{H,F}$=1.4, H-1'); 7.19 (d, 1H, $J_{H,F}$=2.3, H-6); 7.36 (m, 24, H-m-Bz); 7.42 (dd, 1H, $J_{5,4}$=5.1, $J_{5,2}$=3.0, H-5-thienyl); 7.42 and 7.50 (2 x>m, 2×2H, H-m-Bz); 7.54, 7.59 and 7.62 (3×m, 3×1H, H-p-Bz); 7.87 (ddd, 14, $J_{4,5}$=5.1, $J_{4,2}$=1.2, $J_{H,F}$=0.8, H-4-thienyl); 7.94, 8.01 and 8.15 (3×m, 3×24, H-o-Bz); 8.23 (dd, 1H, $J_{2,5}$=3-0, $J_{2,4=1.2}$, H-2-thienyl); 8.86 (s, 1H, H-2). $^{13}$C NMR (125.7 MHz, CDCl$_3$): 63.77 (CH$_2$-5'); 71.47 (CH-3'); 73.74 (CH-2'); 80.30 (CH-4'); 85.53 (CH-1'); 105.49 (d, $J_{C,F}$=15, C-4a); 108.23 (d, $J_{C,F}$=31, CH-6); 125.89 (CH-5-thienyl); 128.08 (d, $J_{C,F}$=6, CH-4-thienyl); 128.41 (C-i-Bz); 128.47, 128.54 and 128.71 (CH-m-Bz); 129.13 (d, $J_{C,F}$=11, CH-2-thienyl); 129.33 (C-i-Bz); 129.69, 129.83 and 129.84 (CH-o-Bz); 133.53 and 133.73 (CH-p-Bz); 139.02 (C-3-thienyl); 142.97 (d, $J_{C,F}$=251, C-5); 148.31 (d, $J_{C,F}$=3, C-7a); 152.35 (CH-2); 152.94 (d, $J_{C,F}$=4, C-4); 165.11, 165.41 and 166.14 (CO). $^{19}$F NMR (470.3 MHz, CDCl$_3$): −154.62. MS FAB, m/z (rel. %): 664 (100)[M+H]. HR MS (FAB): calcd for C$_{36}$H$_{27}$FN$_3$O$_7$S [M+H] 664.1554. found 664.1552.

Example 25

5-Fluoro-7-(β-D-ribofuranosyl)-4-(thiazol-2-yl)-7H-pyrrolo[2,3-d]pyrimidine (8g)

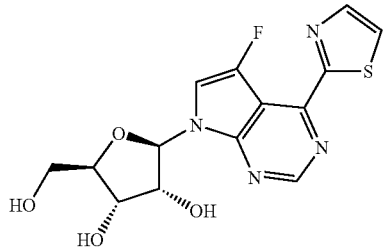

Compound 7g (317 mg, 0.48 mM) is treated with 1M NaOMe/MeOH (143 μL, 0.14 mM) in MeOH (5 mL) for 12 h at RT. The mixture is co-evaporated with silica and chromatographed on the column of silica (3% MeOH in CHCl$_3$) affording product 8g as yellow solid (115 mg, 68%). Compound has crystallized from MeOH as yellow crystals. $^1$H NMR (600 MHz, DMSO-d$_6$): 3.57 (ddd, 1H, $J_{gem}$=11.9, $J_{5'b,OH}$=5.4, $J_{5'b,4'}$=3.9, H-5'b); 3.65 (ddd, 1H, $J_{gem}$=11.9, $J_{5'b,OH}$=5.4, $J_{5'a,4'}$=4.0, H-5'a); 3.93 (ddd, 1H, $J_{4',5'}$=4.0, 3.9, $J_{4',3'}$=3.4, H-4'); 4.12 (td, 1H, $J_{3',2'}$=$J_{3,OH}$=4.9, $J_{3',4'}$=3.4, H-3); 4.37 (ddd, 1H, $J_{2',OH}$=6.2, $J_{2',1'}$=6.1, $J_{2',3'}$=4.9, H-2); 5.11 (t, 1H, $J_{OH,5'}$=5.4, OH-5'); 5.23 (d, 1H, $J_{OH,3}$=4.9, OH-3'); 5.46 (d, 1H, $J_{OH,2}$=6.2, OH-2'); 6.34 (dd, 1H, $J_{1',2'}$=6.1, $J_{H,F}$=1.7, H-1'); 8.05 (d, 1H, $J_{H,F}$=2.2, H-6); 8.08 (d, 1H, $J_{5,4}$=3.1, H-5-thiazolyl); 8.20 (d, 1H, $J_{4,5}$=3.1, H-4-thiazolyl); 8.90 (s, 1H, H-2). $^{13}$C NMR (151 MHz, DMSO-d$_6$): 61.58 (CH$_2$-5'); 70.65 (CH-3'); 74.43 (CH-2'); 85.54 (CH-4'); 86.49 (CH-1); 103.01 (d, $J_{C,F}$=16, C-4a); 112.27 (d, $J_{C,F}$=29, CH-6); 125.00 (CH-5-thiazolyl); 141.60 (d, $J_{C,F}$=252, C-5); 145.80 (CH-4-thiazolyl); 148.28 (d$_{C,F}$=3, C-7a); 148.87 (d, $J_{C,F}$=5 C-4); 151.49 (CH-2); 166.49 (d, $J_{C,F}$=3, C-2-thiazolyl). $^{19}$F NMR (470.3 MHz, DMSO-d$_6$, ref (C$_6$F$_6$)=−163 ppm): −157.84. IR (KBr): ν=1632, 1589, 1565, 1454, 1415, 1221, 1108, 1018 cm$^{-1}$. MS FAB, m/z (rel. %): 221 (60), 353 (100)[M+H]. HR MS (FAB): calcd for C$_{14}$H$_{14}$FN$_4$O$_4$S [M+H] 353.0720. found 353.0713.

The intermediate compound 7g is prepared as follows.

a. 5-Fluoro-4-(thiazol-2-yl)-7-(2,3,5-tri-O-benzoyl-β-D-ribofuranosyl)-7H-pyrrolo[2,3-d]pyrimidine (7g). An argon purged mixture of 6-chloro-7-fluorodeazapurine riboside 6 (376 mg, 0.61 mM), 2-(tributylstannyl)thiazole (361 mg, 0.96 mM) and PdCl$_2$(PPh$_3$)$_2$ (22 mg, 0.03 mM) in DMF (3 mL) is stirred at 100° C. for 2 h. Volatiles are removed in vacuo and the residue is several times co-evaporated with toluene. Column chromatography on silica (hexanes-AcOEt, 15.1→6:1) affords product 7g as yellow foam (347 mg, 86%). $^1$H NMR (600 MHz, CDCl$_3$): 4.70 (dd, 1H, J$_{gem}$=12.2, J$_{5'b,4'}$=3.7, H-5'b); 4.81 (ddd, 1H, J$_{4',3'}$=4.1, J$_{4',5'}$=3.7, 3.0, H-4'); 4.89 (dd, 1H, J$_{gem}$=12.2, J$_{5'a,4'}$=3.0, H-5'a); 6.10 (dd, 1H, J$_{3',2'}$=5.8, J$_{3',4'}$=4.1, H-3'); 6.16 (dd, 1H, J$_{2',1'}$=6.0, J$_{2',3'}$=5.8, H-2'); 6.86 (dd, 1H, J$_{1',2'}$=6.0, J$_{H,F}$=1.2, H-1'); 7.29 (d, 1H, J$_{H,F}$=2.7H-6); 7.36, 7.42 and 7.50 (3×m, 3×2H, H-m-Bz); 7.54 and 7.59 (2×m, 2×1H, H-p-Bz); 7.59 (d, 1H, J$_{5,4=3.1}$, H-5-thiazolyl); 7.61 (m, 1H, H-p-Bz); 7.93 and 8.02 (2×m, 2×2H, H-o-Bz); 8.13 (d, 1H, J$_{4,5}$=3.1, H-4-thiazolyl); 8.15 (m, 2H, H-o-Bz); 8.86 (s, 1H, H-2). $^{13}$C NMR (151 MHz, CDCl$_3$): 63.69 (CH$_2$-5'); 71.42 (CH-3'); 73.75 (CH-2'); 80.37 (CH-4'); 85.61 (CH-1'); 104.51 (d, J$_{C,F}$=16, C-4a); 110.17 (d, J$_{C,F}$=30, CH-6); 123.27 (CH-5-thiazolyl); 128.29 (C-i-Bz); 128.46 and 128.53 (CH-m-Bz); 128.59 (C-i-Bz); 128.73 (CH-n-Bz); 129.18 (C-i-Bz); 129.63, 129.79 and 129.80 (CH-o-Bz); 133.57 and 133.74 (CH-p-Bz); 142.94 (d, J$_{C,F}$=257, C-5); 145.48 (CH-4-thiazolyl); 148.71 (d, J$_{C,F}$=3, C-7a); 149.94 (d, J$_{C,F}$=5, C-4); 151.69 (CH-2); 165.03, 165.38 and 166.14 (CO); 166.65 (d, J$_{C,F}$=3, C-2-thiazolyl). $^{19}$F NMR (470.3 MHz, CDCl$_3$): −155.97. MS FAB, m/z (rel. %): 665 (100) [M+H]. HR MS (FAB): calcd for C$_{35}$H$_{26}$FN$_4$O$_7$S [M+H] 665.1506. found 665.1531.

Example 26

5-Fluoro-4-(1H-imidazol-4-yl)-7-(β-D-ribofuranosyl)-7H-pyrrolo[2,3-d]pyrimidine (8h)

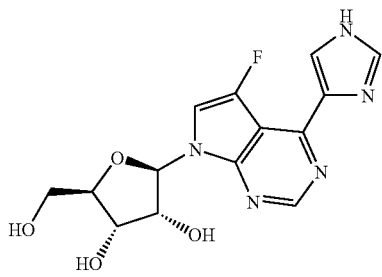

Compound 7h (230 mg, 0.26 mM) in pyridine (2 mL) is treated with 1M NaOMe/MeOH (800 µL, 0.8 mM) for 1 h at RT. Resulting solution is desalted by Dowex 50 (pyridinium form) and volatiles are evaporated in vacuo and the residue is several times co-evaporated with MeOH/toluene and then is treated with 90% aqueous TFA (1 mL) for 18 h at RT. The volatiles are removed in vacuo and the residue is several times co-evaporated with MeOH. Reverse phase chromatography affords nucleoside 8h (61 mg, 70%) as white hardly soluble solid. $^1$H NMR (500 MHz, DMSO-d$_6$+DCl): 3.54 (dd, 1H, J$_{gem}$=12.0, J$_{5'b,4'}$=3.9, H-5'b); 3.61 (dd, 1H, J$_{gem}$=12.0, J$_{5'a,4'}$=4.0, H-5'a); 3.93 (ddd, 1H, J$_{4',5'}$=4.0, 3.9, J$_{4',3'}$=3.2, H-4'); 4.11 (dd, 1H, J$_{3',2'}$=5.1, J$_{3',4'}$=3.2, H-3'); 4.35 (dd, 1H, J$_{2',1'}$=6.1, J$_{2',3'}$=5.1, H-2'); 6.30 (dd, 1H, J$_{1',2'}$=6.11, J$_{H,F}$=1.9, H-1'); 8.08 (d, 1H, J$_{H,F}$=1.9, H-6); 8.24 (d, 1H, J$_{5,2}$=1.2, H-5-imidazole); 8.94 (s, 1H, H-2); 9.30 (d, 1H, J$_{2,5}$=1.2, H-2-imidazole). $^{13}$C NMR (125.7 MHz, DMSO-d$_6$+DCl): 61.67 (CH$_2$-5'); 70.79 (CH-3'); 74.65 (CH-2'); 85.85 (CH-4'); 86.84 (CH-1'); 103.75 (d, J$_{C,F}$=16, CH-4a); 112.11 (d, J$_{C,F}$=30, CH-6); 121.87 (d, J$_{C,F}$=18, CH-5-imidazole); 129.59 (C-4-imidazole); 137.01 (CH-2-imidazole); 141.26 (d, J$_{C,F}$=247, C-5); 143.82 (d, J$_{C,F}$=4, C-4); 147.63 (d, J$_{C,F}$=3, CH-7a); 151.59 (CH-2). $^{19}$F NMR (470.3 MHz, DMSO-d$_6$+DCl): −163.29.

The intermediate compound 7h is prepared as follows.

a. 5-Fluoro-7-(2,3,5-tri-O-benzoyl-β-D-ribofuranosyl)-4-(1-trityl-1H-imidazol-4-yl)-7H-pyrrolo[2,3-d]pyrimidine (7h). Ethylmagnesium bromide (1M sol. in THF, 1.84 mL, 1.84 mM) is added to an argon purged solution of 4-iodo-1-trityl-1H-imidazole (696 mg, 1.6 mM) in dry THF (6 mL) and the resulting solution is stirred for 10 min at ambient temperature, followed by the addition of solution of ZnCl$_2$ (1M sol. in THF, 3.2 mL, 3.2 mM). The mixture is stirred for 2 h at RT and the resulting thick white slurry is transferred to an argon purged flask with 6-chloro-7-fluorodeazapurine riboside 6 (493 mg, 0.8 mM) and Pd(PPh$_3$)$_4$ (46 mg, 0.04 mM) and stirred at 95° C. for 12 h. The mixture is diluted with chloroform (20 mL) and washed with aqueous EDTA (sat., 20 mL). Aqueous layer is re-extracted with chloroform (2×5 mL). Collected organic extracts are dried over MgSO$_4$, evaporated and chromatographed on silica (hexanes-AcOEt, 2:1) affording product 7h (386 mg, 54%) as orange foam. $^1$H NMR (600 MHz, CDCl$_3$): 4.67 (dd, 1H, J$_{gem}$=12.2, J$_{5'b,4'}$=3.9, H-5'b); 4.77 (ddd, 1H, J$_{4',5'}$=3.9, 3.2, J$_{4',3'}$=3.7, H-4'); 4.84 (dd, 1H, J$_{gem}$=12.2, J$_{5'a,4'}$=3.2, H-5'a); 6.04 (dd, 1H, J$_{3',2'}$=5.8, J$_{3',4'}$=3.7, H-3); 6.07 (t, 1H, J$_{2',1'}$=J$_{2',3'}$=5.8, H-2'); 6.84 (dd, 1H, J$_{1',2'}$=5.8, J$_{H,F}$=1.0, H-1'); 7.13 (bs, 1H, H-6); 7.16-7.20 (m, 6H, H-o-Tr); 7.32-7.38 (m, 1H, H-m-Tr and H-m-Bz); 7.41 and 7.48 (2×m, 2×2H, H-m-Bz); 7.53, 7.58 and 7.59 (3×m, 3×1H, H-p-Bz); 7.69 (bs, 1H, H-2-imidazole); 7.84 (d, 1H, J$_{5,2}$=1.3, H-5-imidazole); 7.90, 8.01 and 8.12 (3×m, 3×2H, H-o-Bz); 8.83 (s, 1H, H-2). $^{13}$C NMR (151 MHz, CDCl$_3$): 63.81 (CH$_2$-5'); 71.46 (CH-3'); 73.71 (CH-2'); 76.42 (C-Tr); 80.36 (CH-4'); 85.25 (CH-1'); 104.39 (d, J$_{C,F}$=16, C-4a); 108.13 (b CH-6); 125.70 (d, J$_{C,F}$=16, CH-5-imidazole); 128.28, 128.46, 128.53 (CH-m-Bz and CH-m,p-Tr); 128.67 (C-i-Bz); 128.70 (CH-m-Bz); 129.27 (C-i-Bz); 129.65, 129.72 and 129.81 (CH-o-Bz and CH-o-Tr); 133.49 and 133.72 (CH-p-Bz); 137.17 (C-4-imidazole); 140.21 (CH-2-imidazole); 141.64 (C-i-Tr); 143.02 (d, J$_{C,F}$=251, C-5); 148.11 (C-4 and C-7a); 152.22 (CH-2); 165.09, 165.40 and 166.11 (CO). $^{19}$F NMR (470.3 MHz, CDCl$_3$): −158.87.

Example 27

5-Fluoro-7-(β-D-ribofuranosyl)-4-(pyrrol-3-yl)-7H-pyrrolo[2,3-d]pyrimidine (8l)

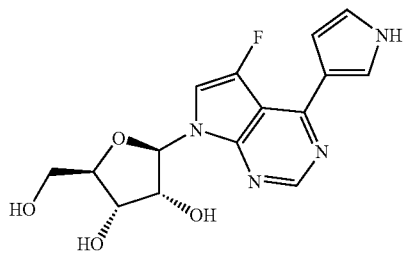

To an argon purged mixture of unprotected riboside 9 (177 mg, 0.58 mM), 1-(triisopropylsilyl)-1H-pyrrole-3-boronic acid (195 mg, 0.73 mM), Cs$_2$(CO$_3$)$_2$ (570 mg, 1.75 mM) is added a pre-prepared solution of Pd(OAc)$_2$ (6.5 mg, 0.029 mM) and TPPTS (41 mg, 0.07 mM) in water/CH$_3$CN (2:1, 3 mL). The reaction mixture is stirred at 100° C. for 3 h. After cooling the mixture is neutralized by the addition of aqueous HCl (3M sol.), co-evaporated with silica and chromatographed on the column of silica (5%→47% MeOH in CHCl$_3$) affording product 8i (141 mg, 73%) as white solid. Compound is crystallized from MeOH providing white powder. $^1$H NMR (600 MHz, DMSO-d$_6$): 3.55 (ddd, 1H, J$_{gem}$=12.0, J$_{5'b,OH}$=5.6, J$_{5'b,4'}$=4.0, H-5'b); 3.63 (ddd, 1H, J$_{gem}$=12.0, J$_{5'a,OH}$=5.4, J$_{5'a,4'}$=4.1, H-5'a); 3.90 (ddd, 1H, J$_{4',5'}$=4.1, 4.0, J$_{4',3'}$=3.4, H-4'); 4.09 (td, 1H, J$_{3',2'}$=J$_{3',OH}$=4.9, J$_{3',4'}$=3.4, H-3'); 4.35 (ddd, H, J$_{2',OH}$=6.4, J$_{2',1'}$=6.1, J$_{2',3'}$=4.9, H-2'); 5.09 (dd, 1H, J$_{OH,5'}$=5.6, 5.4, OH-5'); 5.19 (d, 1H, J$_{OH,3'}$=4.9, OH-3'); 5.40 (d, 1H, J$_{OH,2'}$=6.4, OH-2'); 6.27 (dd, 1H, J$_{1',2'}$=6.1, J$_{H,F}$=1.9, H-1'); 6.88 (ddd, 1H, J$_{4,5}$=2.9, J$_{4,NH}$=2.4, J$_{4,2}$=2.0, H-4-pyrr); 6.92 (ddd, 1H, J$_{5,4}$=2.9, J$_{5,NH}$=2.7, J$_{5,2}$=1.5, H-5-pyrr); 7.69 (ddd, 1H, J$_{2,NH}$=2.9, J$_{2,4}$=2.0, J$_{2,5}$=1.5, H-2-pyrr); 7.80 (d, 1H, J$_{H,F}$=1.7, H-6); 8.66 (s, 1H, H-2); 11.42 (bs, 1H, NH). $^{13}$C NMR (151 MHz, DMSO-d$_6$): 61.70 (CH$_2$-5'); 70.69 (CH-3'); 74.18 (CH-2'); 85.30 (CH-4'); 86.27 (CH-1'); 102.66 (d, J$_{C,F}$=16, C-4-a); 108.58 (d, J$_{C,F}$=8, CH-4-pyrr); 108.80 (d, J$_{C,F}$=31, CH-6); 119.85 (CH-5-pyrr); 121.51 (C-3-pyrr); 122.07 (d, J$_{C,F}$=13, CH-2-pyrr); 142.09 (d, J$_{C,F}$=246, C-5); 147.45 (d, J$_{C,F}$=3, C-7a); 151.94 (CH-2); 153.47 (d, J$_{C,F}$=4, C-4). $^{19}$F NMR (470.3 MHz, DMSO-d$_6$, ref (C$_6$F$_6$)=–163 ppm): –161.58. IR (KBr): ν=1572, 1547, 1465, 1427, 1062, 1024 cm$^{-1}$. MS FAB, m/z (rel. %): 203 (100), 335 (35)[M+H]. HR MS (FAB): calcd for C$_{15}$H$_{16}$FN$_4$O$_4$ [M+H] 335.1156. found 335.1156.

The intermediate compound 9 is prepared as follows.

a. 4-Chloro-5-fluoro-7-[2,3-O-isopropylidene-5-O-tert-butyldimethylsily-β-D-ribofuranosyl]-7H-pyrrolo[2,3-d]pyrimidine (12). Tris(dimethylamino)-phosphine (706 µL, 3.9 mM) is dropwise added to a stirred solution of 2,3-O-isopropylidene-5-O-tert-butyldimethylsily-β-D-ribofuranose (914 mg, 3 mM) and carbon tetrachloride (468 µL, 4.5 mM) in toluene (5 mL) during 35 min at –30° C. The temperature of reaction mixture is raised to 0° C. during 1 h. The mixture is washed with ice-cold brine (5 mL), dried over MgSO$_4$ and added to a stirred mixture of 4-chloro-5-fluoropyrrolo[2,3-d]pyrimidine 10 (343 mg, 2 mM), powdered KOH (253 mg, 4.5 mM) and TDA-1 (320 µL, 1 mM) in toluene (5 mL). The mixture is stirred for 24 hours and then saturated NH$_4$Cl (20 mL) is added and mixture is extracted with chloroform (30 mL, then 2×5 mL). Collected organic extracts are dried over MgSO$_4$, evaporated and chromatographed on silica (hexanes-AcOEt, 22:1) affording product 12 (390 mg, 43%) as colorless oil. $^1$H NMR (600 MHz, CDCl$_3$): 0.10 and 0.11 (2×s, 2×3H, CH$_3$Si); 0.92 (s, 9H, (CH$_3$)$_3$C); 1.38 (q, 3H, J=0.5, (CH$_3$)$_2$C); 1.65 (q, 3H, J=0.5, (CH$_3$)$_2$C); 3.81 (dd, 1H, J$_{gem}$=11.4, J$_{5'b,4'}$=3.2, H-5'b); 3.91 (dd, 1H, J$_{gem}$=11.4, J$_{5'a,4'}$=2.9, H-5'a); 4.38 (ddd, 1H, J$_{4',5'}$=3.2, 2.9, J$_{4',3'}$=2.4, H-4'); 4.91 (dd, 1H, J$_{3',2'}$=6.2, J$_{3',4'}$=2.4, H-3'); 4.93 (dd, 1H, J$_{2',3'}$=6.2, J$_{2',1'}$=2.6, H-2'); 6.47 (dd, 1H, J$_{1',2'}$=2.6, J$_{H,F}$=1.5, H-1'); 7.44 (d, 1H, J$_{H,F}$=2.5, H-6); 8.65 (s, 1H, H-2). $^{13}$C NMR (151 MHz, CDCl$_3$): –5.33 and –5.44 (CH$_3$Si); 18.38 (C(CH$_3$)$_3$); 25.41 ((CH$_3$)$_2$C); 25.87 ((CH$_3$)$_3$C); 27.33 ((CH$_3$)$_2$C); 63.53 (CH$_2$-5'); 80.73 (CH-3'); 85.32 (CH-2'); 86.19 (CH-4'); 90.16 (CH-1'); 107.56 (d, J$_{C,F}$=14, C-4a); 107.62 (d, J$_{C,F}$=27, CH-6); 114.24 (C(CH$_3$)$_2$); 141.49 (d, J$_{C,F}$=253, C-5); 146.50 (d, J$_{C,F}$=1, C-7a); 150.54 (d, J$_{C,F}$=4, C-4); 151.66 (CH-2). $^{19}$F NMR (470.3 MHz, CDCl$_3$, ref (C$_6$F$_6$)=–163 ppm): –168.82.

b. 4-Chloro-5-fluoro-7-β-D-ribofuranosyl-7H-pyrrolo[2,3-d]pyrimidine (9). Protected nucleoside 12 (350 mg, 0.76 mM) is treated with 90% aqueous TFA (1 mL) for 2 h. The volatiles are evaporated in vacuo and the residue is several times co-evaporated with MeOH. Chromatography on silica (4% MeOH in CHCl$_3$) affords free nucleoside 9 (198 mg, 85%) as white foam. $^1$H NMR (600 MHz, DMSO-d$_6$): 3.56 (ddd, 1H, J$_{gem}$=12.0, J$_{5'b,OH}$=5.4, J$_{5'b,4'}$=3.9, H-5'b); 3.64 (ddd, 1H, J$_{gem}$=12.0, J$_{5'a,OH}$=5.4, J$_{5'a,4'}$=4.0, H-5'a); 3.93 (ddd, 1H, J$_{4',5'}$=4.0, 3.9, J$_{4',3'}$=3.3, H-4'); 4.10 (td, 1H, J$_{3',2'}$=J$_{3',OH}$=5.0, J$_{3',4'}$=3.3, H-3'); 4.33 (ddd, 1H, J$_{2',OH}$=6.2, J$_{2',1'}$=5.9, J$_{2',3'}$=5.0, H-2'); 5.09 (t, 1H, J$_{OH,5'}$=5.4, OH-5'); 5.22 (d, 1H, J$_{OH,3'}$=5.0, OH-3'); 5.44 (d, 1H, J$_{OH,2'}$=6.2, OH-2'); 6.25 (dd, 1H, J$_{1',2'}$=5.9, J$_{H,F}$=1.9, H-1'); 8.02 (d, 1H, J$_{H,F}$=2.0, H-6); 8.70 (s, 1H, H-2). $^{13}$C NMR (151 MHz, DMSO-d$_6$): 61.48 (CH$_2$-5'); 70.55 (CH-3'); 74.53 (CH-2'); 85.66 (CH-4'); 86.98 (CH-1'); 106.55 (d, J$_{C,F}$=14, C-4a); 111.42 (4, J$_{C,F}$=27, CH-6); 140.45 (d, J$_{C,F}$=249, C-5); 146.97 (d, J$_{C,F}$=1, C-7a); 149.09 (d, J$_{C,F}$=4, C-4); 151.65 (CH-2). $^{19}$F NMR (470.3 MHz, DMSO-d$_6$, ref (C$_6$F$_6$)=–163 ppm): –169.72.

Example 28

5-Chloro-4-phenyl-7-(β-D-ribofuranosyl)-7H-pyrrolo[2,3-d]pyrimidine (15a)

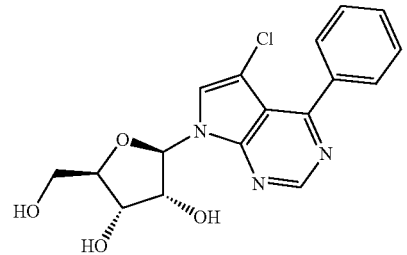

Compound 14a (409 mg, 0.61 mM) is treated with 1M NaOMe/MeOH (185 µL, 0.185 mM) in MeOH (5 mL) for 12 h at RT. The mixture is co-evaporated with silica and chromatographed on the column of silica (3% MeOH in CHCl$_3$) affording product 15a (200 mg, 91%) as colorless solid. Crystallization from MeOH/AcOEt/hexane provided white powder. $^1$H NMR (600 MHz, DMSO-d$_6$): 3.58 (ddd, 1H, J$_{gem}$=1.9, J$_{5'b,OH}$=5.4, J$_{5'b,4'}$=3.9, H-5'b); 3.66 (ddd, 1H, J$_{gem}$=11.9, J$_{5'a,OH}$=5.2, J$_{5'a,4'}$=4.1, H-5'a); 3.95 (ddd, 1H, J$_{4',5'}$=4.1, 3.9, J$_{4',3'}$=3.3, H-4'); 4.13 (td, 1H, J$_{3',2'}$=J$_{3',OH}$=4.9, J$_{3',4'}$=3.3, H-3'); 4.43 (ddd, 1H, J$_{2',OH}$=6.3, J$_{2',1'}$=6.1, J$_{2',3'}$=4.9, H-2'); 5.13 (dd, 1H, J$_{OH,5'}$=5.4, 5.2, OH-5'); 5.24 (d, 1H, J$_{OH,3'}$=4.9, OH-3'); 5.47 (d, 1H, J$_{OH,2'}$=6.3, OH-2'); 6.36 (d, 1H, J$_{1',2'}$=6.1, H-1'); 7.53-7.58 (m, 3H, H-m,p-Ph); 7.76 (m, 2H, H-o-Ph); 8.17 (s, 1H, H-6); 8.94 (s, 1H, H-2). $^{13}$C NMR (151 MHz, DMSO-d$_6$): 61.57 (CH$_2$-5'); 70.68 (CH-3'); 74.42 (CH-2'); 85.64 (CH-4'); 86.74 (CH-1'); 103.36 (C-5); 113.01 (C-4a); 125.46 (CH-6); 128.07 (CH-m-Ph); 130.04 (CH-p-Ph); 130.36 (CH-o-Ph); 136.54 (C-i-Ph); 150.71 (C-7a); 151.74 (CH-2); 158.81 (C-4). IR (KBr): ν=1560, 1460, 1441, 1343, 1199, 1124, 1103, 1084, 1075, 1044, 984 cm$^{-1}$. MS FAB, m/z (rel. %): 230 (100), 362 (15)[M+H]. HR MS (FAB): calcd for C$_{17}$H$_{17}$ClN$_3$O$_4$ [M–H] 362.0908. found 362.0922.

The intermediate compound 14a is prepared as follows.

a. 5-Chloro-4-phenyl-7-(2,3,5-tri-O-benzoyl-β-D-ribofuranosyl)-7H-pyrrolo[2,3-d]pyrimidine (14a). An argon purged mixture of protected 6,7-dichloro-7-deazapurine riboside 13 (394 mg, 0.62 mM), phenylboronic acid (91 mg, 0.75 mM), K$_2$CO$_3$ (172 mg, 1.25 mM) and Pd(PPh$_3$)$_4$ (36 mg, 0.031 mM) in toluene (3 mL) is stirred at 100° C. for 4 h. The mixture is diluted with chloroform (20 mL) and washed with aqueous NH$_4$Cl (sat., 20 mL), aqueous phase is re-extracted with chloroform (2×5 mL). Collected organic extracts are dried over MgSO$_4$, volatiles are removed in vacuo and the residue is chromatographed on silica (hexanes-AcOEt, 7:1) affording product 14a (398 mg, 95%) as yellowish foam. $^1$H NMR (600 MHz, CDCl$_3$): 4.71 (dd, 1H, J$_{gem}$=12.2, J$_{5'b,4'}$=3.7, H-5'b); 4.82 (ddd, 1H, J$_{4',3'}$=4.6, J$_{4',5'}$=3.7, 3.1, H-4'); 4.90 (dd, 1H, J$_{gem}$=12.2, J$_{5'a,4}$=3.1, H-5'a); 6.14 (dd, 1H, J$_{3',2'}$=5.9, J$_{3',4'}$=4.6, H-3'); 6.21 (dd, 1H, J$_{2',3}$=5.9, J$_{2',1'}$=5.5, H-2'); 6.81 (d, 1H, J$_{2',1}$=5.5, H-1'); 7.37 (m, 2H, H-m-Bz); 7.40 (s, 1H, H-6); 7.41 (m, 2H, H-m-Bz); 7.47-7.52 (m, 5H, H-m,p-Ph and H-m-Bz); 7.55, 7.59 and 7.60 (3×m, 3×1H, H-p-Bz); 7.77 (m, 2H, H-o-Ph); 7.96, 8.01 and 8.14 (3×m, 3×2H, H-o-Bz); 8.94 (s, 1H, H-2). $^{13}$C NMR (151 MHz, CDCl$_3$): 63.57 (CH$_2$-5'); 71.37 (CH-3'); 73.94 (CH-2'); 80.35 (CH-4'); 86.15 (CH-1'); 106.44 (C-5); 114.15 (C-4a); 123.36 (CH-6); 127.87 (CH-m-Ph); 128.41 (C-i-Bz); 128.50 and 128.53 (CH-m-Bz); 128.66 (C-i-Bz); 128.71 (CH-m-Bz); 129.30 (C-i-Bz); 129.69, 129.81 and 129.84 (CH-o-Bz); 129.88 (CH-p-Ph); 130.25 (CH-o-Ph); 133.51, 133.73 and 133.76 (CH-p-Bz); 136.22 (C-i-Ph); 150.88 (C-7a); 152.05 (CH-2); 160.10 (C-4); 165.11, 165.38 and 166.14 (CO). MS FAB, m/z (rel. %): 674 (100)[M+H]. HR MS (FAB): calcd for C$_{38}$H$_{29}$ClN$_3$O$_7$ [M+H] 674.1694. found 674.1695.

Example 29

5-Chloro-4-(furan-2-yl)-7-(β-D-ribofuranosyl)-7H-pyrrolo[2,3-d]pyrimidine (15b)

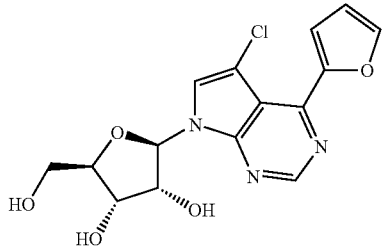

Compound 1.4b (197 mg, 0.30 mM) is treated with 1M NaOMe/MeOH (60 μL, 0.06 mM) in MeOH (5 mL) for 12 h at RT. The mixture is desalted with Dowex 50 in pyridinium form and crystallization of reside from MeOH/CHCl$_3$ provides yellowish powder and reverse phase chromatography of mother liquors provides additional portion of desired product. Total yield of product 15b is 91 mg (86%). $^1$H NMR (400 MHz, DMSO-d$_6$): 3.58 and 3.66 (2×ddd, 2H, J$_{gem}$=12.0, J$_{5',OH}$=5.4, J$_{5',4}$=3.9, H-5'); 3.94 (q, 1H, J$_{4',5}$=3.9, J$_{4',3}$=3.4, H-4'); 4.12 (td, 1H, J$_{3',2}$=5.0, J$_{3',OH}$=4.9, J$_{3',4}$=3.4, H-3'); 4.40 (td, 1H, J$_{2',OH}$=6.2, J$_{2',1}$=6.0, J$_{2',3}$=5.0, H-2'); 5.12 (t, 1H, J$_{OH,5}$=5.4, OH-5'); 5.21 (d, 1H, J$_{OH,3}$=4.9, OH-3'); 5.45 (d, 1H, J$_{OH,2}$=6.2, OH-2'); 6.29 (d, 1H, J$_{1',2}$=6.0, H-1'); 6.79 (dd, 1H, J$_{4,3}$=3.5, J$_{4,5}$=1.7, H-4-furyl); 7.43 (dd, 1H, J$_{3,4}$=3.5, J$_{3,5}$=0.8, H-3-furyl); 8.06 (dd, 1H, J$_{5,4}$=1.7, J$_{5,3}$=0.8, H-5-furyl); 8.17 (s, H, H-6); 8.84 (s, 1H, H-2). $^{13}$C NMR (100.6 MHz, DMSO-d$_6$): 61.48 (CH$_2$-5'); 70.57 (CH-3'); 74.38 (CH-2'); 85.55 (CH-4'); 86.67 (CH-1'); 103.40 (C-5); 110.67 (C-4a); 112.76 (CH-4-furyl); 115.42 (CH-3-furyl); 125.95 (CH-6); 146.47 (CH-5-furyl); 147.15 (C-4); 150.86 (C-2-furyl); 151.26 (C-7a); 151.41 (CH-2). IR (KBr): ν=1627, 1586, 1556, 1454, 1335, 1105, 1060, 984 cm$^{-1}$. MS FAB, m/z (rel. %): 220 (60), 352 (100)[M+H]. HR MS (FAB): calcd for C$_{15}$H$_{15}$ClN$_3$O$_5$ [M+H] 352.0700. found 352.0698.

The intermediate compound 14b is prepared as follows.

a. 5-Chloro-4-(furan-2-yl)-7-(2,3,5-tri-O-benzoyl-β-D-ribofuranosyl)-7H-pyrrolo[2,3-d]pyrimidine (14b). An argon purged mixture of protected 6,7-dichloro-7-deazapurine riboside 13 (207 mg, 0.327 mM), 2-(tributylstannyl)furane (125 μL, 0.40 mM) and PdCl$_2$(PPh$_3$)$_2$ (12 mg, 0.02 mM) in DMF (2 mL) is stirred at 100° C. for 2 h. Volatiles are removed in vacuo and the residue is several times co-evaporated with toluene. Column chromatography on silica (hexanes-AcOEt, 10:1→6:1) affords product 14b (215 mg, 99%) as yellow foam. $^1$H NMR (400 MHz, CDCl$_3$): 4.70 (dd, 1H, J$_{gem}$=12.2, J$_{5'b,4'}$=3.7, H-5'b); 4.80 (dt, 1H, J$_{4',3}$=4.4, J$_{4',5}$=3.7, 3.1, H-4'); 4.89 (dd, 1H, J$_{gem}$=12.2, J$_{5'a,4}$=3.1, H-5'a); 6.11 (dd, 1H, J$_{3',2}$=5.8, J$_{3',4}$=4.4, H-3'); 6.16 (t, 1H, J$_{2',3}$=5.8, J$_{2',1}$=5.5, H-2'); 6.62 (dd, 1H, J$_{4,3}$=3.5, J$_{4,5}$=1.8, H-4-furyl); 6.79 (d, 1H, J$_{1',2}$=5.6, H-1'); 7.36 and 7.41 (2×m, 2×2H, H-m-Bz); 7.42 (s, 1H, H-6); 7.47 (dd, 1H, J$_{3,4}$=3.5, J$_{3,5}$=0.8, H-3-furyl); 7.50 (m, 2H, H-m-Bz); 7.54, 7.58 and 7.61 (3×m, 3×TH, H-p-Bz); 7.71 (dd, 1H, J$_{5,4}$=1.8, J$_{5,3}$=0.8, H-5-furyl); 7.94, 8.00 and 8.14 (3×m, 3×2H, H-o-Bz); 8.85 (s, 1H, H-2). $^{13}$C NMR (100.6 MHz, CDCl$_3$): 63.60 (CH$_2$-5'); 71.42 (CH-3'); 73.99 (CH-2'); 80.40 (CH-4'); 86.01 (CH-1'); 106.28 (C-5); 111.89 (C-4a); 112.22 (CH-4-furyl); 116.15 (CH-3-furyl); 123.75 (CH-6); 128.45 (C-i-Bz); 128.48, 128.53 and 128.73 (CH-i-Hz); 129.34 (C-i-Bz); 129.70, 129.82 and 129.85 (CH-o-Bz); 133.49 and 133.71 (CH-p-Bz); 145.42 (CH-5-furyl); 148.41 (C-4); 150.54 (C-2-furyl); 151.49 (C-7a); 151.82 (CH-2); 165.08, 165.37 and 166.14 (CO). MS FAB, m/z (rel. %): 175 (100), 664 (65)[M+H]. HR MS (FAB), calcd for C$_{36}$H$_{27}$ClN$_3$O$_8$ [M+H] 664.1487. found 664.1495.

Example 30

5-Chloro-7-(β-D-ribofuranosyl)-4-(thiophen-2-yl)-7H-pyrrolo[2,3-d]pyrimidine (15c)

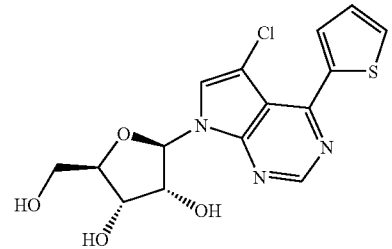

Compound 14c (183 mg, 0.27 mM) is treated with 1M NaOMe/MeOH (60 μL, 0.06 mM) in MeOH (5 mL) for 12 h at RT. The mixture is desalted with Dowex 50 in pyridinium form and crystallization of reside from MeOH/CHCl$_3$ provides white powder and reverse phase chromatography of mother liquors provides additional portion of desired product. Total yield of product 15c is 93 mg (94%). $^1$H NMR (400 MHz, DMSO-d$_6$): 3.58 and 3.67 (2×ddd, 2H, J$_{gem}$=12.0, J$_{5',OH}$=5.5, J$_{5',4}$=3.8, H-5'); 3.95 (q, 1H, J$_{4',5}$=3.8, J$_{4',3}$=3.4, H-4'); 4.13 (td, 1H, J$_{3',2}$=5.0, J$_{3',OH}$=4.9, J$_{3',4}$=3.4, H-3'); 4.41 (td, 1H, J$_{2',OH}$=6.2, J$_{2',1}$=6.0, J$_{2',3}$=5.0, H-2'); 5.12 (t, 1H, J$_{OH,5}$=5.5, OH-5'); 5.22 (d, 1H, J$_{OH,3}$=4.9, OH-3'); 5.46 (d, 1H, J$_{1',2}$=6.2, OH-2'); 6.30 (d, 1H, J$_{1',2}$=6.0, H-1); 7.29 (dd, 1H, J$_{4,5}$=5.0, J$_{4,3}$=3.8, H-4-thienyl); 7.89 (dd, 1H, J$_{5,4}$=5.0, J$_{5,3}$=1.1, H-5-thienyl); 8.06 (dd, 1H, J$_{3,4}$=3.8, J$_{3,5}$=1.1, H-3-thienyl); 8.19 (s, 1H, H-6); 8.83 (s, 1H, H-2). $^{13}$C NMR (100.6 MHz, DMSO-d$_6$): 61.48 (CH$_2$-5'); 70.56 (CH-3'); 74.41 (CH-2'); 85.57 (CH-4'); 86.79 (CH-1'); 102.94 (C-5);

111.24 (C-4a); 125.85 (CH-6); 128.46 (CH-4-thienyl); 131.30 (CH-5-thienyl); 132.36 (CH-3-thienyl); 140.54 (C-2-thienyl); 151.15 (C-7a); 151.31 (CH-2); 151.70 (C-4). %): 236 (75), 368 (100)[M+H]. IR (KBr): ν=1556, 1454, 1351, 1282, 1098, 1035, 975 cm$^{-1}$. HR MS (FAB): calcd for $C_{15}H_{15}ClN_3O_4S$: [M+H] 368.0472. found 368.0480. Anal. Calcd for $C_{15}H_{14}ClN_3O_4S$: C, 48.98; H, 3.84; N, 11.42. Found: C, 48.68; H, 3.76; N, 11.13.

The intermediate compound 14c is prepared as follows.

a. 5-Chloro-4-(thiophen-2-yl)-7-(2,3,5-tri-O-benzoyl-β-D-ribofuranosyl)-7H-pyrrolo[2,3-d]pyrimidine (14c). An argon purged mixture of protected 6,7-dichloro-7-deazapurine riboside 13 (207 mg, 0.327 mM), 2-(tributylstannyl)thiophene (127 μL, 0.40 mM) and $PdCl_2(PPh_3)_2$ (12 mg, 0.02 mM) in DMF (3 mL) is stirred at 100° C. for 2 h. Volatiles are removed in in vacuo and the residue is several times co-evaporated with toluene. Column chromatography on silica (hexanes-AcOEt, 20:1→6:1) affords product 14c (198 mg, 89%) as foam. $^1$H NMR (400 MHz, CDCl$_3$): 4.70 (dd, 1H, $J_{gem}$=12.2, $J_{5'b,4'}$=3.7, H-5b); 4.81 (dt, 1H, $J_{4',3'}$=4.4, $J_{4',5'}$=3.7, 3.1, H-4'); 4.89 (dd, 1H, $J_{gem}$=12.2, $J_{5'a,4'}$=3.1, H-5'a); 6.11 (dd, 1H, $J_{3',2'}$=5.8, $J_{3',4'}$=4.4, H-3'); 6.16 (t, 1H, $J_{2',3'}$=5.8, $J_{2',1'}$=5.6, H-2'); 6.80 (d, 1H, $J_{1',2'}$=5.6, H-1'); 7.18 (dd, 1H, $J_{4,5}$=5.1, $J_{4,3}$=3.8, H-4-thienyl); 7.36 and 7.41 (2×m, 2×2H, H-m-Hz); 7.42 (s, 1H, H-6); 7.50 (m, 2H, H-m-Bz); 7.54 (m, 1H, H-p-Bz); 7.57 (dd, 1H, $J_{5,4}$=5.1, $J_{5,3}$=1.1, H-5-thienyl); 7.58 and 7.61 (2×m, 2×1H, H-p-Hz); 7.94 and 8.11 (2×m, 2×2H, H-o-Bz); 8.03 (dd, 1H, $J_{3,4}$=3.8, $J_{3,5}$=1.1, H-3-thienyl); 8.14 (m, 2H, H-o-Bz); 8.83 (s, 1H, H-2). $^{13}$C NMR (100.6 MHz, CDCl$_3$): 63.63 (CH$_2$-5'); 71.45 (CH-3'); 73.99 (CH-2'); 80.46 (CH-4'); 86.02 (CH-1'); 106.00 (C-5); 112.57 (C-4a); 123.52 (CH-6); 127.88 (CH-4-thienyl); 128.45 (C-i-Bz); 128.49 and 128.54 (CH-m-Bz); 128.71 (C-i-Bz); 128.74 (CH-m-Bz); 129.34 (C-i-Bz); 129.70, 129.83 and 129.86 (CH-o-Bz); 130.27 (CH-5-thienyl); 132.47 (CH-3-thienyl); 133.51, 133.72 and 133.73 (CH-p-Bz); 140.50 (C-2-thienyl); 151.41 (C-7a); 151.72 (CH-2); 153.19 (C-4); 165.09, 165.38 and 166.14 (CO). MS FAB, m/z (rel. %): 680 (100)[M+H]. HR MS (FAB): calcd for $C_{36}H_{27}ClN_3O_7S$ [M+H] 680.1258. found 680.1264.

Example 31

5-Chloro-4-(furan-3-yl)-7-(β-D-ribofuranosyl)-7H-pyrrolo[2,3-d]pyrimidine (15d)

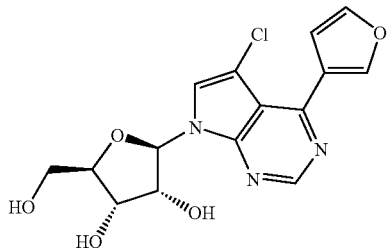

Compound 14d (366 mg, 0.55 mM) is treated with 1M NaOMe/MeOH (165 μL, 0.165 mM) in MeOH (5 mL) for 12 h at RT. The mixture is co-evaporated with silica and chromatographed on the column of silica (4% MeOH in CHCl$_3$) affording product 15d (155 mg, 80%) as white solid. Crystallization from MeOH/CHCl$_3$ gives white crystals. $^1$H NMR (600 MHz, DMSO-d$_6$): 3.57 (ddd, 1H, $J_{gem}$=12.0, $J_{5'b,OH}$=5.4, $J_{5'b,4'}$=3.9, H-5'b); 3.66 (ddd, 1H, $J_{gem}$=12.0, $J_{5'a,OH}$=5.3, $J_{5'a,4'}$=4.0, H-5'a); 3.94 (ddd, 1H, $J_{4',5'}$=4.0, 3.9 $J_{4',3'}$=3.2, H-4'); 4.12 (ddd, 1H, $J_{3',OH}$=4.8, $J_{3',2'}$=4.7, $J_{3',4'}$=3.2, H-3'); 4.40 (ddd, 1H, $J_{2',1'}$=6.1, $J_{2',OH}$=5.8, $J_{2',3'}$=4.7, H-2'); 5.14 (dd, 1H, $J_{OH,5'}$=5.4, 5.3, OH-5'); 5.24 (d, 1H, $J_{OH,3'}$=4.8, OH-3'); 5.47 (d, 1H, $J_{OH,2'}$=5.8, OH-5r); 6.29 (d, 1H, $J_{1',2'}$=6.1, H-11); 7.08 (dd, 1H, $J_{4,5}$=1.9, $J_{4,2}$=0.8, H-4-furyl); 7.86 (dd, 1H, $J_{5,4}$=1.9, $J_{5,2}$=1.6, H-5-furyl); 8.14 (s, 1H, H-6); 8.37 (dd, 1H, $J_{2,5}$=1.6, $J_{2,4}$=0.8, H-2-furyl); 8.86 (s, 1H, H-2). $^{13}$C NMR (151 MHz, DMSO-d$_6$): 61.59 (CH$_2$-5'); 70.68 (CH-3'); 74.46 (CH-2'); 85.63 (CH-4'); 86.72 (CH-1'); 103.11 (C-5); 111.71 (CH-4-furyl); 112.67 (C-4a); 123.30 (C-3-furyl); 125.38 (CH-6); 143.95 (CH-5-furyl); 145.67 (CH-2-furyl); 150.74 (C-7a); 151.39 (C-4); 151.75 (CH-2). IR (KBr): ν=1562, 1461, 1426, 1105, 1040, 984 cm$^{-1}$. MS FAB, m/z (rel. %): 352 (100)[M+H]. HR MS (FAB): calcd for $C_{15}H_{15}ClN_3O_5$ [M+H] 352.0700. found 3152.0715.

The intermediate compound 14d is prepared as follows.

a. 5-Chloro-4-(furan-3-yl)-7-(2,3,5-tri-O-benzoyl-β-D-ribofuranosyl)-7H-pyrrolo[2,3-d]pyrimidine (14d). An argon purged mixture of protected 6,7-dichloro-7-deazapurine riboside 13 (506 mg, 0.8 mM), furane-3-boronic acid (117 mg, 1.04mM), K$_2$CO$_3$ (221 mg, 1.60 mM) and Pd(PPh$_3$)$_4$ (46 mg, 0.04 mM) in toluene (5 mL) is stirred at 100° C. for 10 h. The mixture is diluted with chloroform (20 mL) and washed with aqueous NH$_4$Cl (sat., 20 mL), aqueous phase is re-extracted with chloroform (2×5 mL). Collected organic extracts are dried over MgSO$_4$, volatiles are removed in vacuo and the residue is chromatographed on silica (hexanes-AcOEt, 7:1) affording product 14d (457 mg, 86%) as yellowish foam. $^1$H NMR (600 MHz, CDCl$_3$): 4.70 (dd, 1H, $J_{gem}$=12.2, $J_{5'b,4'}$=3.7, H-5'b); 4.81 (ddd, 1H, $J_{4',3'}$=4.4, $J_{4',5'}$=3.7, 3.1, H-4'); 4.89 (dd, 1H, $J_{gem}$=12.2, $J_{5'a,4'}$=3.1, H-5'a); 6.12 (dd, in, $J_{3',2'}$=5.8, $J_{3',4'}$=4.4, H-3'); 6.17 (dd, 1H, $J_{2',3'}$=5.8, $J_{2',1'}$=5.6, H-2'); 6.79 (d, 1H, $J_{1',2'}$=5.6, H-1'); 7.06 (dd, 1H, $J_{4,5}$=1.9, $J_{4,2}$=0.8, H-4-furyl); 7.37 (m, 2H, H-m-Bz); 7.39 (s, 1H, H-6); 7.41 and 7.50 (2×m, 2×2H, H-m-Bz); 7.53 (dd, 1H, $J_{5,4}$=10.9, $J_{52}$=1.5, H-5-furyl); 7.54, 7.58 and 7.61 (3×m, 3×1H, H-p-Bz); 7.94, 8.00 and 8.14 (3×m, 3×2H, H-o-Bz); 8.18 (dd, 1H, $J_2$=−1.5, $J_{2,4}$=0.8, H-2-furyl); 8.86 (s, 1H, H-2). $^{13}$C NMR (151 MHz, CDCl$_3$): 63.60 (CH$_2$-5'); 71.40 (CH-3'); 73.93 (CH-2'); 80.38 (CH-4'); 85.97 (CH-1'); 105.89 (C-5); 111.32 (CH-4-furyl); 113.70 (C-4a); 123.13 (C-3-furyl); 123.25 (CH-6); 128.39 (C-i-Bz); 128.49 and 128.54 (CH-m-Bz); 128.65 (C-i-Bz); 128.73 (CH-m-Bz); 129.29 (C-i-Bz); 129.69, 129.82 and 129.84 (CH-o-Bz); 133.53, 133.74 and 133.75 (CH-p-Bz); 143.01 (CH-5-furyl); 145.42 (CH-2-furyl); 150.92 (C-7a); 152.02 (CH-2); 152.54 (C-4); 165.10, 165.39 and 166.14 (CO). MS FAB, ml: (rel. %): 445 (50), 664 (100)[M+H]. HR MS (FAB): calcd for $C_{36}H_{27}ClN_3O_8$ [M+H] 664.1487. found 664.1467.

Example 32

5-Chloro-7-(β-D-ribofuranosyl)-4-(thiophen-3-yl)-7H-pyrrolo[2,3-d]pyrimidine (15e)

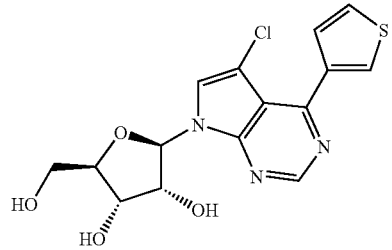

Compound 14e (480 mg, 0.71 mM) is treated with 1M NaOMe/MeOH (212 μL, 0.212 mM) in MeOH (5 mL) for 12 h at RT. The mixture is Co-evaporated with silica and chromatographed on the column of silica (4% MeOH in CHCl$_3$) affording product 15v (225 mg, 87%) as colorless solid. Crystallization from MeOH provides hard beige prisms. $^1$H NMR (600 MHz, DMSO-d$_6$): 3.57 (ddd, 1H, J$_{gem}$=12.0, J$_{5'b,OH}$=5.4, J$_{5'b,4'}$=4.0, H-5'b); 3.66 (ddd, 1H, J$_{gem}$=12.0, J$_{5'a,OH}$=5.3, J$_{5'a,4'}$=4.1, H-5'a); 3.94 (ddd, 1H, J$_{4,5}$=4.1, 4.0 J$_{4',3'}$=2.9, H-4'); 4.12 (ddd, 1H, J$_{3',OH}$=4.6, J$_{3',2'}$=4.3, J$_{3',4'}$=2.9, H-3'); 4.41 (ddd, 1H, J$_{2',1'}$=6.1, J$_{2',OH}$=5.4, J$_{2',3'}$=4.3, H-2'); 5.14 (dd, 1H, J$_{OH,5}$=5.4, 5.3, OH-5'); 5.24 (d, 1H, J$_{OH,3}$=4.6, OH-3'); 5.47 (d, 1H, J$_{OH,2}$=5.4, OH-5'); 6.30 (d, 1H, J$_{1',2'}$=6.1, H-1'); 7.61 (dd, 1H, J$_{4,5}$=5.07 J$_{4,2}$=1.3, H-4-thienyl); 7.69 (dd, 1H, J$_{5,4}$=5.0, J$_{5,2}$=2.9, H-5-thienyl); 8.12 (dd, 1H, J$_{2,5}$=2.9, J$_{2,4}$=1.3, H-2-thienyl); 8.15 (s, 1H, H-6); 8.88 (s, 1H, H-2). $^{13}$C NMR (151 MHz, DMSO-d$_6$): 61.60 (CH$_2$-5'); 70.70 (CH-3'); 74.46 (CH-2'); 85.65 (CH-4'); 86.73 (CH-1'); 103.33 (C-5); 112.74 (C-4a); 125.46 (CH-6); 126.26 (CH-5-thienyl); 129.35 (CH-4-thienyl); 129.94 (CH-2-thienyl); 138.02 (C-3-thienyl); 150.87 (C-7a); 151.69 (CH-2); 153.90 (C-4). IR (KBr): ν=1632, 1579, 1568, 1463, 1447, 1437, 1195, 1131, 1124, 1090, 1069, 1037, 1026, 996, 987 cm$^{-1}$. MS FAB, m/z (rel. %): 236 (80), 368 (100)[M+H]. HR MS (FAB): calcd for C$_{15}$H$_{15}$ClN$_3$O$_4$S [M+H] 368.0472. found 368.0471. Anal. Calcd for C$_{15}$H$_{14}$ClN$_3$O$_4$S.1.35CH$_3$OH: C, 47.77; H, 4.76; N, 10.22. Found: C, 47.74; H, 4.70; N, 10.28.

The intermediate compound 14e is prepared as follows.

a. 5-Chloro-4-(thiophen-3-yl)-7-(2,3,5-tri-O-benzoyl-β-D-ribofuranosyl)-7H-pyrrolo[2,3-d]pyrimidine (14e). An argon purged mixture of protected 6,7-dichloro-7-deazapurine riboside 13 (506 mg, 0.8 mM), thiophene-3-boronic acid (133 mg, 1.04 mM), K$_2$CO$_3$ (221 mg, 1.60 mM) and Pd(PPh$_3$)$_4$ (46 mg, 0.04 mM) in toluene (5 mL) is stirred at 100° C. for 10 h. The mixture is diluted with chloroform (20 mL) and washed with aqueous NH$_4$Cl (sat., 20 mL), aqueous phase is re-extracted with chloroform (2×5 mL). Collected organic extracts are dried over MgSO$_4$, volatiles are removed in vacuo and the residue is chromatographed on silica (hexanes-AcOEt, 6:1) affording product 14e (500 mg, 92%) as yellowish foam. $^1$H NMR (600 MHz, CDCl$_3$): 4.70 (dd, 1H, J$_{gem}$=12.2, J$_{5'b,4'}$=3.7, H-5'b); 4.81 (ddd, 1H, J$_{4',3'}$=4.5, J$_{4',5'}$=3.7, 3.1, H-4'); 4.90 (dd, 1H, J$_{gem}$=12.2, J$_{5'a,4'}$=3.1, H-5'a); 6.13 (dd, 1H, J$_{3',2'}$=6.0, J$_{3',4'}$=4.5, H-3'); 6.19 (dd, 1H, J$_{2',3'}$=6.0, J$_{2',1'}$=5.6, H-2'); 6.80 (d, 1H, J$_{1',2'}$=5.6, H-1'); 7.37 (m, 2H, H-m-Bz); 7.40 (s, 1H, H-6); 7.41 (dd, 1H, J$_{5,4}$=5.0, J$_{5,2}$=3.0, H-5-thienyl); 7.41 and 7.50 (2×m, 2×2H, H-m-Bz); 7.55, 7.57 and 7.61 (3×m, 3×1H, H-p-Bz); 7.64 (dd, 1H, J$_{4,5}$=5.0, J$_{4,2}$=1.3, H-4-thienyl); 7.95 (dd, 1H, J$_{2,5}$=3.0, J$_{2,4}$=1.3, H-2-thienyl); 7.95, 8.01 and 8.14 (3×m, 3×2H, H-o-Bz); 8.89 (s, 1H, H-2). $^{13}$C NMR. (151 MHz, CDCl$_3$): 63.59 (CH$_2$-5'); 71.39 (CH-3'); 73.95 (CH-2'); 80.38 (CH-4'); 86.05 (CH-1'); 106.20 (C-5); 113.79 (C-4a); 123.88 (CH-6); 125.23 (CH-5-thienyl); 128.40 (C-i-Bz); 128.50 and 128.54 (CH-m-Bz); 128.66 (C-i-Bz); 128.73 (CH-m-Bz); 129.10 (CH-4-thienyl); 129.30 (C-i-Bz); 129.40 (CH-2-thienyl); 129.69, 129.82 and 129.85 (CH-o-Bz); 133.53, 133.74 and 133.76 (CH-p-Bz); 137.71 (C-3-thienyl); 151.04 (C-7a); 151.94 (CH-2); 154.89 (C-4); 165.10, 165.39 and 166.14 (CO). MS FAB, m/z (rel. %): 680 (100)[M+H]. HR MS (FAB): calcd for C$_{36}$H$_{27}$ClN$_3$O$_7$S [M+H] 680.1258. found 680.1247.

Example 33

Effects of the Compounds on Cell Cycle Distribution in Human T-Lymphoid Cells

Human T-lymphoid cell line CCRF-CEM is treated with tested compounds for 72 hours at the concentration corresponding to the CC$_{50}$ value of each compound. At the end of incubation, cells are harvested by centrifugation, washed, and fixed in ethanol. Fixed cells are stained with propidium iodide in a buffer containing RNaseA and the cell cycle distribution analysis is performed by flow cytometry using BD FACSAria instrument. Data are processed using BD FACSDiva software v4.1 and presented as a percentage of analyzed cell population in Phase G1, S, and G2/M. Cell cycle distribution is determined in parallel for untreated and treated cells and relative change for each cell cycle phase is calculated.

Results from the representative compounds are summarized in Table 2. The data represent changes in the frequency of each cell cycle phase in treated cells relative to untreated control (the relative fraction of each analyzed cell cycle phase in untreated control has the value of 1).

Primary data are shown in Table 3, with values representing the percentage distribution of each cell cycle phase in the total cell population.

TABLE 2

| Compound | Structure | Relative change in cell cycle phase compared to untreated control* | | |
|---|---|---|---|---|
| | | G1 | S | G2/M |
| Example 5 | 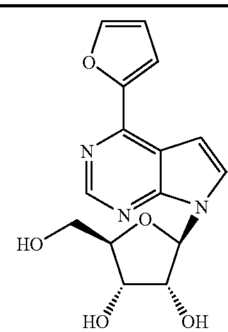 | 0.57 | 1.38 | 1.19 |

TABLE 2-continued

| Compound | Structure | Relative change in cell cycle phase compared to untreated control* | | |
|---|---|---|---|---|
| | | G1 | S | G2/M |
| Example 6 | 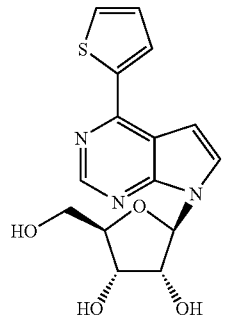 | 0.52 | 1.34 | 1.54 |
| Example 21 | 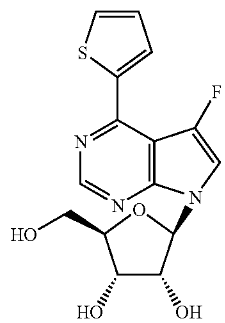 | 0.74 | 1.12 | 1.38 |
| Example 20 | 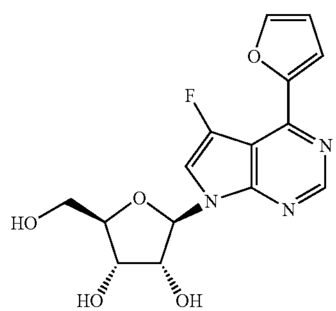 | 0.61 | 1.06 | 2.00 |

TABLE 3

| | G1 % | S % | G2/M % |
|---|---|---|---|
| Example 5 | | | |
| Control 1 | 42.93 | 44.94 | 12.14 |
| Control 2 | 45.11 | 43.26 | 11.62 |
| 0.3 μM 1 | 26.14 | 61.98 | 11.89 |
| 0.3 μM 2 | 23.61 | 59.99 | 16.41 |
| Example 6 | | | |
| Control 1 | 42.93 | 44.94 | 12.14 |
| Control 2 | 45.11 | 43.26 | 11.62 |
| 0.3 μM 1 | 30.82 | 54.65 | 14.53 |
| 0.3 μM 2 | 14.66 | 63.29 | 22.05 |
| Example 21 | | | |
| Control 1 | 43.11 | 41.14 | 15.74 |
| Control 2 | 43.06 | 39.19 | 17.75 |
| 0.3 μM 1 | 30.83 | 46.37 | 22.80 |
| 0.3 μM 2 | 32.73 | 43.74 | 23.53 |
| Example 20 | | | |
| Control 1 | 42.72 | 43.77 | 13.51 |
| Control 2 | 41.49 | 44.36 | 14.15 |
| 1.5 μM 1 | 22.32 | 47.49 | 30.19 |
| 1.5 μM 2 | 28.81 | 45.95 | 25.24 |

Treatment with each of the tested compounds affects the distribution of cell cycle in human T-lymphoid cells. The representative compounds decrease the fraction of cells in G1 phase and correspondingly increase the fraction of cells in S and G2/M phases, indicating that the compounds could block the cell proliferation progression and/or inhibit tumor cell growth through multiple phases of the cell cycle.

Example 34

Induction of Apoptosis by the Compounds of the Present Invention

Human T-lymphoid cell line CCRF-CEM is treated with tested compounds for 72 hours at several concentrations based on the $CC_{50}$ value of each compound. At the end of incubation, cells are harvested by centrifugation, washed and resuspended in the calcium-containing buffer supplemented with annexin V-FITC conjugate and propidium iodide (PI). After the end of incubation cells are washed again and immediately analysed by flow cytometry using BD FACSAria instrument. Data are processed using FlowJo software v7.2.5 and presented as a percentage of analyzed cell population that is considered as healthy (double negative), early apoptotic (annexin V positive, PI negative), late apoptotic/necrotic (double positive) or purely necrotic (PI positive, annexin V negative). Untreated cells serve as a negative control that refers to the naturally ongoing apoptosis in the cell culture.

Results from the representative compounds are summarized in Table 4, with values representing the percentage distribution of differentially stained subpopulations as mentioned above.

TABLE 4

| | Concentration (μM) | Cell Distribution (%) | | | |
|---|---|---|---|---|---|
| | | Healthy | Early Apoptotic | Late Apoptotic/ Necrotic | Necrotic |
| Untreated Control | | 89 | 4 | 4 | 3 |
| | 0.2 | 40 | 14 | 40 | 6 |
| | 0.2 | 60 | 8 | 28 | 4 |
| | 0.4 | 33 | 11 | 49 | 7 |

Treatment with each of the tested compounds results in the induction of apoptosis in human T-lymphoid cells. This effect is concentration-dependent.

Example 35

The Following Illustrate Representative Pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/mL |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

The invention has been described with reference to various specific and preferred embodiments and techniques. However, it should be understood that many variations and modifications may be made while remaining within the spirit and scope of the invention.

What is claimed is:

1. A compound of formula I:

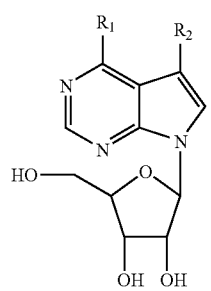

(I)

wherein:
$R_1$ is furanyl, thienyl, pyrrolyl, thiazoyl, imidazolyl, pyridyl, selenophenyl, or pyrazolyl; and
$R_2$ is hydrogen, heteroaryl, halo, or aryl that is optionally substituted with one or more groups selected from ($C_1$-$C_6$)alkyl, ($C_1$-$C_6$)alkoxy, ($C_1$-$C_6$)alkylthio, halo, amino, nitro, cyano, trifluoro, trifluoromethyl, or hydroxy; or a salt thereof.

2. The compound of claim 1, wherein $R_1$ is 5-membered heteroaryl, or hydroxyl-$(C_1$-$C_4)$alkyl, $R_2$ is hydrogen, or halo; or a salt thereof.

3. The compound of claim 1, wherein $R_2$ is hydrogen or halo, or a salt thereof.

4. The compound of claim 3, wherein $R_2$ is hydrogen.

5. The compound of claim 3, wherein $R_2$ is halo.

6. A method of inhibiting tumor/cancer growth in a subject comprising administering to the subject a therapeutically effective amount of the compound according to claim 1.

7. A method of inhibiting cell proliferation in tumor/cancer cells in a subject comprising administering to the subject a therapeutically effective amount of the compound according to claim 1.

8. A method of treating a cellular proliferation disease in a subject comprising administering to the subject a therapeutically effective amount of the compound according to claim 1.

9. A method of treating a neoplastic disease in a subject comprising administering to the subject a therapeutically effective amount of the compound according to claim 1.

10. A method of treating a tumor or cancer in a subject comprising administering to the subject a therapeutically effective amount of the compound according to claim 1.

11. A pharmaceutical composition comprising a therapeutically effective amount of the compound according to claim 1 and one or more pharmaceutically acceptable carriers.

* * * * *